(12) United States Patent
Palermo et al.

(10) Patent No.: US 7,867,249 B2
(45) Date of Patent: *Jan. 11, 2011

(54) CLIP APPLIER AND METHODS OF USE

(75) Inventors: Thomas J Palermo, San Jose, CA (US); William M Belef, San Jose, CA (US); Michael T Carley, San Jose, CA (US); Richard S Ginn, San Jose, CA (US); Ronald J Jabba, Redwood City, CA (US); Anthony Pantages, Los Altos, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 951 days.

This patent is subject to a terminal disclaimer.

(21) Appl. No.: 10/638,115

(22) Filed: Aug. 8, 2003

(65) Prior Publication Data
US 2004/0153123 A1    Aug. 5, 2004

Related U.S. Application Data

(63) Continuation-in-part of application No. 10/356,214, filed on Jan. 30, 2003.

(51) Int. Cl.
A61B 17/08    (2006.01)

(52) U.S. Cl. ..................................... 606/213
(58) Field of Classification Search ............ 606/139, 606/213, 151, 153, 140, 141, 142, 143, 144, 606/145, 146, 147, 148, 215, 216, 220, 221
See application file for complete search history.

(56) References Cited

U.S. PATENT DOCUMENTS 287,046 A    10/1883    Norton
(Continued)

FOREIGN PATENT DOCUMENTS

CA    2 339 060    2/2000
(Continued)

OTHER PUBLICATIONS

PCT Publication No. WO 00/07640, "Vascular Suction Cannula, Dialator and Surgical Stapler", Feb. 17, 2000.
(Continued)

Primary Examiner—Anhtuan T Nguyen
Assistant Examiner—Tuan V Nguyen
(74) Attorney, Agent, or Firm—Workman Nydegger

(57) ABSTRACT

An apparatus for delivering a closure element into an opening formed in a blood vessel or other body lumen and methods for manufacturing and using same. The apparatus is configured to retain the closure element such that the closure element is disposed substantially within the apparatus. The apparatus also can engage, and position the closure element substantially adjacent to, the blood vessel wall adjacent to the opening. During deployment of the closure element, the apparatus expands the closure element beyond a natural cross-section of the closure element such that the closure element, when deployed, is configured to engage a significant amount of the blood vessel wall and/or tissue. Engaging the blood vessel wall and/or tissue, the closure element is further configured to return to the natural cross-section, thereby drawing the engaged blood vessel wall and/or tissue substantially closed and/or sealed, such that hemostasis within the opening is enhanced.

26 Claims, 31 Drawing Sheets

U.S. PATENT DOCUMENTS

| | | |
|---|---|---|
| 438,400 A | 10/1890 | Brennen |
| 1,088,393 A | 2/1914 | Backus |
| 1,331,401 A | 2/1920 | Summers |
| 1,426,111 A | 8/1922 | Sacker |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | LeRoy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborn |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |

| | | | | | |
|---|---|---|---|---|---|
| 5,061,274 A | 10/1991 | Kensey | 5,366,458 A | 11/1994 | Korthoff et al. |
| 5,071,430 A | 12/1991 | de Salis et al. | 5,366,479 A | 11/1994 | McGarry et al. |
| 5,078,731 A | 1/1992 | Hayhurst | 5,376,101 A | 12/1994 | Green et al. |
| 5,092,941 A | 3/1992 | Miura | 5,383,896 A | 1/1995 | Gershony et al. |
| 5,100,418 A | 3/1992 | Yoon et al. | 5,383,905 A | 1/1995 | Golds et al. |
| 5,100,422 A | 3/1992 | Berguer et al. | RE34,866 E | 2/1995 | Kensey et al. |
| 5,108,420 A | 4/1992 | Marks | 5,391,173 A | 2/1995 | Wilk |
| 5,108,421 A | 4/1992 | Fowler | 5,392,978 A | 2/1995 | Velez |
| 5,114,032 A | 5/1992 | Laidlaw | 5,395,030 A | 3/1995 | Kuramoto et al. |
| 5,114,065 A | 5/1992 | Storace | 5,409,499 A | 4/1995 | Yi |
| 5,116,349 A | 5/1992 | Aranyi | 5,411,520 A | 5/1995 | Nash et al. |
| 5,122,122 A | 6/1992 | Allgood | 5,413,571 A | 5/1995 | Katsaros et al. |
| 5,122,156 A | 6/1992 | Granger et al. | 5,413,584 A | 5/1995 | Schulze |
| 5,131,379 A | 7/1992 | Sewell, Jr. | 5,416,584 A | 5/1995 | Kay |
| 5,147,381 A | 9/1992 | Heimerl et al. | 5,417,699 A | 5/1995 | Klein et al. |
| 5,156,609 A | 10/1992 | Nakao et al. | 5,419,777 A | 5/1995 | Hofling |
| 5,158,566 A | 10/1992 | Pianetti | 5,423,857 A | 6/1995 | Rosenman et al. |
| 5,160,339 A | 11/1992 | Chen et al. | 5,425,489 A | 6/1995 | Shichman et al. |
| 5,167,634 A | 12/1992 | Corrigan, Jr. et al. | 5,425,740 A | 6/1995 | Hutchinson, Jr. |
| 5,167,643 A | 12/1992 | Lynn | 5,431,639 A | 7/1995 | Shaw |
| 5,171,249 A | 12/1992 | Stefanchik et al. | 5,431,667 A | 7/1995 | Thompson et al. |
| 5,171,250 A | 12/1992 | Yoon | 5,433,721 A | 7/1995 | Hooven et al. |
| 5,171,251 A | 12/1992 | Bregen et al. | 5,437,631 A | 8/1995 | Janzen |
| 5,176,648 A | 1/1993 | Holmes et al. | 5,439,479 A | 8/1995 | Shichman et al. |
| 5,176,682 A | 1/1993 | Chow | 5,443,477 A | 8/1995 | Marin et al. |
| 5,192,288 A | 3/1993 | Thompson et al. | 5,443,481 A | 8/1995 | Lee |
| 5,192,300 A | 3/1993 | Fowler | 5,449,359 A | 9/1995 | Groiso |
| 5,192,301 A | 3/1993 | Kamiya et al. | 5,456,400 A | 10/1995 | Shichman et al. |
| 5,192,302 A | 3/1993 | Kensey et al. | 5,462,558 A | 10/1995 | Kolesa et al. |
| 5,192,602 A | 3/1993 | Spencer et al. | 5,462,561 A | 10/1995 | Voda |
| 5,203,787 A | 4/1993 | Noblitt et al. | 5,466,241 A | 11/1995 | Leroy et al. |
| 5,209,756 A | 5/1993 | Seedhom et al. | 5,470,010 A | 11/1995 | Rothfuss et al. |
| 5,217,024 A | 6/1993 | Dorsey et al. | 5,474,557 A | 12/1995 | Mai |
| 5,219,359 A | 6/1993 | McQuilkin et al. | 5,474,572 A | 12/1995 | Hayhurst |
| 5,222,971 A | 6/1993 | Willard et al. | 5,478,352 A | 12/1995 | Fowler |
| 5,222,974 A | 6/1993 | Kensey et al. | 5,478,353 A | 12/1995 | Yoon et al. |
| 5,226,908 A | 7/1993 | Yoon | 5,478,354 A | 12/1995 | Tovey et al. |
| 5,234,449 A | 8/1993 | Bruker et al. | 5,486,195 A | 1/1996 | Myers et al. |
| 5,236,435 A | 8/1993 | Sewell, Jr. | 5,497,933 A | 3/1996 | DeFonzo et al. |
| 5,236,445 A | 8/1993 | Hayhurst et al. | 5,501,698 A | 3/1996 | Roth et al. |
| 5,242,457 A | 9/1993 | Akopov et al. | 5,507,744 A | 4/1996 | Tay et al. |
| 5,242,459 A | 9/1993 | Buelna | 5,507,755 A | 4/1996 | Gresl et al. |
| 5,246,156 A | 9/1993 | Rothfuss et al. | 5,514,159 A | 5/1996 | Matula et al. |
| 5,246,443 A | 9/1993 | Mai | 5,521,184 A | 5/1996 | Zimmerman |
| 5,250,058 A | 10/1993 | Miller et al. | 5,522,840 A | 6/1996 | Krajicek |
| 5,254,105 A | 10/1993 | Haaga | 5,527,322 A | 6/1996 | Klein et al. |
| 5,258,015 A | 11/1993 | Li et al. | 5,536,251 A | 7/1996 | Evard et al. |
| 5,269,792 A | 12/1993 | Kovac et al. | 5,540,712 A | 7/1996 | Kleshinski et al. |
| 5,275,616 A | 1/1994 | Fowler | 5,540,716 A | 7/1996 | Hlavacek |
| 5,282,808 A | 2/1994 | Kovac et al. | 5,543,520 A | 8/1996 | Zimmerman |
| 5,282,827 A | 2/1994 | Kensey et al. | 5,544,802 A | 8/1996 | Crainich |
| 5,282,832 A | 2/1994 | Toso et al. | 5,547,474 A | 8/1996 | Kloeckl et al. |
| 5,289,963 A | 3/1994 | McGarry et al. | 5,560,532 A | 10/1996 | DeFonzo et al. |
| 5,290,243 A | 3/1994 | Chodorow et al. | 5,571,120 A | 11/1996 | Yoon |
| 5,290,310 A | 3/1994 | Makower et al. | 5,575,771 A | 11/1996 | Walinsky |
| 5,292,309 A | 3/1994 | Van Tassel et al. | 5,584,879 A | 12/1996 | Reimold et al. |
| 5,292,332 A | 3/1994 | Lee | 5,591,205 A | 1/1997 | Fowler |
| 5,304,184 A | 4/1994 | Hathaway et al. | 5,593,412 A | 1/1997 | Martinez |
| 5,304,204 A | 4/1994 | Bregen | 5,593,422 A | 1/1997 | Muijs Van der Moer et al. |
| 5,306,254 A | 4/1994 | Nash et al. | 5,593,425 A | 1/1997 | Bonutti et al. |
| 5,306,280 A | 4/1994 | Bregen et al. | 5,601,602 A | 2/1997 | Fowler |
| 5,318,542 A | 6/1994 | Hirsch et al. ............ 606/198 | 5,609,597 A | 3/1997 | Lehrer |
| 5,320,639 A | 6/1994 | Rudnick | 5,611,986 A | 3/1997 | Datta et al. |
| 5,330,442 A | 7/1994 | Green et al. | 5,613,974 A | 3/1997 | Andreas et al. |
| 5,330,445 A | 7/1994 | Haaga | 5,618,291 A | 4/1997 | Thompson et al. |
| 5,334,216 A | 8/1994 | Vidal et al. | 5,618,306 A | 4/1997 | Roth et al. |
| 5,334,217 A | 8/1994 | Das | 5,620,452 A | 4/1997 | Yoon |
| 5,335,680 A | 8/1994 | Moore | 5,620,461 A | 4/1997 | Muijs et al. |
| 5,340,360 A | 8/1994 | Stefanchik | 5,630,824 A | 5/1997 | Hart |
| 5,350,399 A | 9/1994 | Erlebacher et al. | 5,643,318 A | 7/1997 | Tsukernik et al. |
| 5,352,229 A | 10/1994 | Goble et al. | 5,645,553 A | 7/1997 | Kolesa et al. |
| 5,364,406 A | 11/1994 | Sewell, Jr. | 5,645,565 A | 7/1997 | Rudd et al. |
| 5,364,408 A | 11/1994 | Gordon | 5,645,566 A | 7/1997 | Brenneman et al. |

| | | | | | |
|---|---|---|---|---|---|
| 5,645,567 A | 7/1997 | Crainich | 5,871,501 A | 2/1999 | Leschinsky et al. |
| 5,649,959 A | 7/1997 | Hannam et al. | 5,871,525 A | 2/1999 | Edwards et al. |
| D383,539 S | 9/1997 | Croley | 5,873,876 A | 2/1999 | Christy |
| 5,669,917 A | 9/1997 | Sauer et al. | 5,879,366 A | 3/1999 | Shaw et al. |
| 5,674,231 A | 10/1997 | Green et al. | 5,893,592 A | 4/1999 | Schulze et al. |
| 5,676,689 A | 10/1997 | Kensey et al. | 5,897,487 A | 4/1999 | Ouchi |
| 5,676,974 A | 10/1997 | Valdes et al. ............ 424/542 | 5,902,310 A | 5/1999 | Foerster et al. |
| 5,681,334 A | 10/1997 | Evans et al. | 5,904,697 A | 5/1999 | Gifford, III et al. |
| 5,681,351 A | 10/1997 | Jamiolkowski et al. | 5,906,631 A | 5/1999 | Imran |
| 5,683,405 A | 11/1997 | Yacoublan et al. | 5,907,893 A | 6/1999 | Zadno-Azizi et al. |
| 5,690,674 A | 11/1997 | Diaz | 5,910,155 A | 6/1999 | Ratcliff et al. |
| 5,695,504 A | 12/1997 | Gifford, III et al. | 5,919,207 A | 7/1999 | Taheri |
| 5,695,505 A | 12/1997 | Yoon | 5,919,208 A | 7/1999 | Valenti |
| 5,695,524 A | 12/1997 | Kelley et al. | 5,922,009 A | 7/1999 | Epstein et al. |
| 5,700,273 A | 12/1997 | Buelna et al. | 5,935,147 A | 8/1999 | Kensey et al. |
| 5,709,708 A | 1/1998 | Thal | 5,938,667 A | 8/1999 | Peyser et al. |
| 5,716,375 A | 2/1998 | Fowler | 5,941,890 A | 8/1999 | Voegele et al. |
| 5,720,755 A | 2/1998 | Dakov | 5,947,999 A | 9/1999 | Groiso |
| 5,720,765 A | 2/1998 | Thal | 5,951,518 A | 9/1999 | Licata et al. |
| 5,725,498 A | 3/1998 | Janzen et al. | 5,951,576 A | 9/1999 | Wakabayashi |
| 5,725,552 A | 3/1998 | Kotula et al. | 5,951,589 A | 9/1999 | Epstein et al. |
| 5,725,554 A | 3/1998 | Simon et al. | 5,957,936 A | 9/1999 | Yoon et al. |
| 5,725,556 A | 3/1998 | Moser et al. | 5,957,938 A | 9/1999 | Zhu et al. |
| 5,728,109 A | 3/1998 | Schulze et al. | 5,964,782 A | 10/1999 | LaFontaine et al. |
| 5,728,110 A | 3/1998 | Vidal et al. | 5,976,159 A | 11/1999 | Bolduc et al. |
| 5,728,114 A | 3/1998 | Evans et al. | 5,976,161 A | 11/1999 | Kirsch et al. |
| 5,728,122 A | 3/1998 | Leschinsky et al. | 5,984,934 A | 11/1999 | Ashby et al. |
| 5,728,132 A | 3/1998 | Van Tassel et al. | 5,984,949 A | 11/1999 | Levin |
| 5,732,872 A | 3/1998 | Bolduc et al. | 5,993,468 A | 11/1999 | Rygaard |
| 5,735,873 A | 4/1998 | MacLean | 5,993,476 A | 11/1999 | Groiso |
| 5,735,875 A | 4/1998 | Bonutti et al. | 6,001,110 A | 12/1999 | Adams |
| 5,735,877 A | 4/1998 | Pagedas | 6,004,341 A | 12/1999 | Zhu et al. |
| 5,749,898 A | 5/1998 | Schulze et al. | 6,007,563 A | 12/1999 | Nash et al. |
| 5,752,966 A | 5/1998 | Chang | 6,013,084 A | 1/2000 | Ken et al. |
| 5,755,726 A | 5/1998 | Pratt et al. | 6,022,372 A | 2/2000 | Kontos |
| 5,755,778 A | 5/1998 | Kleshinski | 6,024,750 A | 2/2000 | Mastri |
| 5,766,217 A | 6/1998 | Christy | 6,024,758 A | 2/2000 | Thal |
| 5,766,246 A | 6/1998 | Mulhauser et al. | 6,030,364 A | 2/2000 | Durgin et al. |
| 5,769,862 A | 6/1998 | Kammerer et al. | 6,030,413 A | 2/2000 | Lazarus |
| 5,769,870 A | 6/1998 | Salahieh et al. | 6,033,427 A | 3/2000 | Lee |
| 5,776,150 A | 7/1998 | Nolan et al. | 6,036,703 A | 3/2000 | Evans et al. |
| 5,779,707 A | 7/1998 | Bertholet et al. | 6,036,720 A | 3/2000 | Abrams et al. |
| 5,782,844 A | 7/1998 | Yoon et al. | 6,045,570 A | 4/2000 | Epstein et al. |
| 5,782,860 A | 7/1998 | Epstein et al. | 6,048,358 A | 4/2000 | Barak |
| 5,782,861 A | 7/1998 | Cragg et al. | 6,056,768 A | 5/2000 | Cates et al. |
| 5,782,864 A | 7/1998 | Lizardi | 6,056,769 A | 5/2000 | Epstein et al. |
| 5,795,958 A | 8/1998 | Rao et al. | 6,056,770 A | 5/2000 | Epstein et al. |
| 5,797,928 A | 8/1998 | Kogasaka | 6,059,800 A | 5/2000 | Hart et al. |
| 5,797,931 A | 8/1998 | Bito et al. | 6,063,085 A | 5/2000 | Tay et al. |
| 5,797,933 A | 8/1998 | Snow et al. | 6,063,114 A | 5/2000 | Nash et al. |
| 5,797,958 A | 8/1998 | Yoon | 6,066,160 A | 5/2000 | Colvin et al. |
| 5,810,776 A | 9/1998 | Bacich et al. | 6,071,300 A | 6/2000 | Brenneman et al. |
| 5,810,846 A | 9/1998 | Virnich et al. | 6,074,409 A | 6/2000 | Goldfarb |
| 5,810,851 A | 9/1998 | Yoon | 6,077,281 A | 6/2000 | Das |
| 5,810,877 A | 9/1998 | Roth et al. | 6,077,291 A | 6/2000 | Das |
| 5,814,069 A | 9/1998 | Schulze et al. | 6,080,182 A | 6/2000 | Shaw |
| 5,817,113 A | 10/1998 | Gifford | 6,080,183 A | 6/2000 | Tsugita et al. |
| 5,820,631 A | 10/1998 | Nobles | 6,086,608 A | 7/2000 | Ek et al. |
| 5,827,298 A | 10/1998 | Hart et al. | 6,090,130 A | 7/2000 | Nash et al. |
| 5,830,125 A | 11/1998 | Scribner et al. | 6,092,561 A | 7/2000 | Schmid |
| 5,833,698 A | 11/1998 | Hinchliffe et al. | 6,099,553 A | 8/2000 | Hart et al. |
| 5,843,167 A | 12/1998 | Dwyer et al. | 6,102,271 A | 8/2000 | Longo et al. |
| 5,846,254 A | 12/1998 | Schulze et al. | 6,106,545 A | 8/2000 | Egan |
| 5,853,421 A | 12/1998 | Leschinsky et al. | 6,110,184 A | 8/2000 | Weadock |
| 5,853,422 A | 12/1998 | Huebsch et al. | 6,113,612 A | 9/2000 | Swanson et al. |
| 5,855,312 A | 1/1999 | Toledano | 6,117,125 A | 9/2000 | Rothbarth et al. |
| 5,858,082 A | 1/1999 | Cruz et al. | 6,117,148 A | 9/2000 | Ravo |
| 5,860,991 A | 1/1999 | Klein et al. | 6,120,524 A | 9/2000 | Taheri |
| 5,861,005 A | 1/1999 | Kontos | 6,126,675 A | 10/2000 | Shchervinsky et al. |
| 5,868,755 A | 2/1999 | Kanner et al. | 6,126,677 A | 10/2000 | Ganaja et al. |
| 5,868,763 A | 2/1999 | Spence et al. | 6,136,010 A | 10/2000 | Modesitt et al. |
| 5,871,474 A | 2/1999 | Hermann et al. | 6,143,017 A | 11/2000 | Thal |
| 5,871,490 A | 2/1999 | Schulze et al. | 6,149,660 A | 11/2000 | Laufer et al. |

| | | | |
|---|---|---|---|
| 6,149,667 A | 11/2000 | Hovland et al. | |
| 6,152,144 A | 11/2000 | Lesh et al. | |
| 6,152,934 A | 11/2000 | Harper et al. | |
| 6,152,936 A | 11/2000 | Christy et al. | |
| 6,152,937 A | 11/2000 | Peterson et al. | |
| 6,159,234 A | 12/2000 | Bonutti et al. | |
| 6,165,204 A | 12/2000 | Levinson et al. | |
| 6,174,324 B1 | 1/2001 | Egan et al. | |
| 6,193,734 B1 | 2/2001 | Bolduc et al. | |
| 6,197,042 B1 | 3/2001 | Ginn et al. | 606/213 |
| 6,200,329 B1 | 3/2001 | Fung et al. | |
| 6,203,565 B1 | 3/2001 | Bonutti et al. | |
| 6,206,913 B1 | 3/2001 | Yencho et al. | |
| 6,220,248 B1 | 4/2001 | Voegele et al. | |
| 6,221,102 B1 | 4/2001 | Baker et al. | |
| 6,231,592 B1 | 5/2001 | Bonutti et al. | |
| 6,248,124 B1 | 6/2001 | Pedros et al. | |
| 6,254,615 B1 | 7/2001 | Bolduc et al. | |
| 6,254,617 B1 | 7/2001 | Spence et al. | |
| 6,254,642 B1 | 7/2001 | Taylor | |
| 6,277,140 B2 | 8/2001 | Ginn et al. | |
| 6,280,460 B1 | 8/2001 | Bolduc et al. | |
| 6,287,322 B1 | 9/2001 | Zhu et al. | |
| 6,296,657 B1 | 10/2001 | Brucker | |
| 6,305,891 B1 | 10/2001 | Burlingame | |
| 6,319,258 B1 | 11/2001 | McAllen, III et al. | |
| 6,322,580 B1 | 11/2001 | Kanner | |
| 6,334,865 B1 | 1/2002 | Redmond et al. | |
| 6,348,064 B1 * | 2/2002 | Kanner | 606/219 |
| 6,358,258 B1 | 3/2002 | Arcia et al. | |
| D457,958 S | 5/2002 | Dycus | |
| 6,383,208 B1 | 5/2002 | Sancoff et al. | |
| 6,391,048 B1 | 5/2002 | Ginn et al. | 606/213 |
| 6,395,015 B1 | 5/2002 | Borst et al. | |
| 6,398,752 B1 | 6/2002 | Sweezer et al. | |
| 6,402,765 B1 | 6/2002 | Monassevitch et al. | 606/151 |
| 6,409,739 B1 | 6/2002 | Nobles et al. | |
| 6,419,669 B1 | 7/2002 | Frazier et al. | |
| 6,423,054 B1 | 7/2002 | Ouchi | |
| 6,428,472 B1 | 8/2002 | Haas | |
| 6,428,548 B1 * | 8/2002 | Durgin et al. | 606/142 |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,458,130 B1 | 10/2002 | Frazier et al. | |
| 6,461,364 B1 | 10/2002 | Ginn et al. | 606/142 |
| 6,482,224 B1 | 11/2002 | Michler et al. | |
| 6,488,692 B1 | 12/2002 | Spence et al. | |
| 6,500,115 B2 | 12/2002 | Krattiger et al. | |
| 6,506,210 B1 | 1/2003 | Kanner | |
| 6,517,569 B2 | 2/2003 | Mikus et al. | |
| 6,533,762 B2 | 3/2003 | Kanner et al. | |
| 6,533,812 B2 | 3/2003 | Swanson et al. | |
| 6,537,288 B2 | 3/2003 | Vargas et al. | |
| 6,547,806 B1 | 4/2003 | Ding | |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,582,452 B2 | 6/2003 | Coleman et al. | 606/213 |
| 6,582,482 B2 | 6/2003 | Gillman et al. | |
| 6,599,303 B1 | 7/2003 | Peterson et al. | |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,616,686 B2 | 9/2003 | Coleman et al. | |
| 6,623,509 B2 | 9/2003 | Ginn | |
| 6,623,510 B2 | 9/2003 | Carley et al. | 606/213 |
| 6,626,918 B1 | 9/2003 | Ginn et al. | |
| 6,632,238 B2 | 10/2003 | Ginn et al. | |
| 6,634,537 B2 | 10/2003 | Chen | |
| 6,645,205 B2 * | 11/2003 | Ginn | 606/41 |
| 6,652,538 B2 | 11/2003 | Kayan et al. | |
| 6,652,556 B1 | 11/2003 | VanTassel et al. | |
| 6,663,655 B2 | 12/2003 | Ginn et al. | |
| 6,665,906 B2 | 12/2003 | Li | |
| 6,669,714 B2 | 12/2003 | Coleman et al. | |
| 6,676,671 B2 | 1/2004 | Robertson et al. | |
| 6,676,685 B2 | 1/2004 | Pedros et al. | |
| 6,679,904 B2 | 1/2004 | Gleeson et al. | |
| 6,689,147 B1 | 2/2004 | Koster, Jr. | |
| 6,695,867 B2 | 2/2004 | Ginn et al. | 606/213 |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,719,777 B2 | 4/2004 | Ginn et al. | 606/213 |
| 6,726,704 B1 | 4/2004 | Loshakove et al. | 606/213 |
| 6,743,195 B2 | 6/2004 | Zucker | |
| 6,743,243 B1 | 6/2004 | Roy et al. | |
| 6,743,259 B2 | 6/2004 | Ginn | |
| 6,749,621 B2 * | 6/2004 | Pantages et al. | 606/213 |
| 6,749,622 B2 | 6/2004 | McGuckin et al. | |
| 6,755,842 B2 | 6/2004 | Kanner et al. | |
| 6,767,356 B2 | 7/2004 | Kanner et al. | |
| 6,780,197 B2 * | 8/2004 | Roe et al. | 606/213 |
| 6,837,906 B2 | 1/2005 | Ginn | |
| 6,846,319 B2 | 1/2005 | Ginn et al. | |
| 6,890,343 B2 | 5/2005 | Ginn et al. | |
| 6,896,687 B2 | 5/2005 | Dakov | |
| 6,896,692 B2 | 5/2005 | Ginn et al. | |
| 6,926,723 B1 | 8/2005 | Mulhauser et al. | |
| 6,926,731 B2 | 8/2005 | Coleman et al. | 606/213 |
| 6,942,674 B2 | 9/2005 | Belef et al. | |
| 6,942,691 B1 | 9/2005 | Chuter | |
| 6,964,668 B2 | 11/2005 | Modesitt et al. | |
| 6,969,397 B2 | 11/2005 | Ginn | |
| 6,989,003 B2 | 1/2006 | Wing et al. | |
| 6,989,016 B2 | 1/2006 | Tallarida et al. | |
| 7,001,398 B2 | 2/2006 | Carley et al. | |
| 7,001,400 B1 | 2/2006 | Modesitt et al. | |
| 7,008,435 B2 | 3/2006 | Cummins | |
| 7,008,439 B1 | 3/2006 | Janzen et al. | |
| 7,033,379 B2 | 4/2006 | Peterson | |
| 7,060,084 B1 | 6/2006 | Loshakove et al. | |
| 7,063,711 B1 | 6/2006 | Loshakove et al. | |
| 7,083,635 B2 | 8/2006 | Ginn | |
| 7,108,709 B2 | 9/2006 | Cummins | |
| 7,108,710 B2 | 9/2006 | Anderson | |
| 7,111,768 B2 | 9/2006 | Cummins et al. | |
| 7,112,225 B2 | 9/2006 | Ginn | |
| 7,144,411 B2 | 12/2006 | Ginn et al. | |
| 7,163,551 B2 | 1/2007 | Anthony et al. | |
| 7,169,158 B2 | 1/2007 | Sniffin et al. | |
| 7,169,164 B2 | 1/2007 | Borillo et al. | |
| 7,211,101 B2 | 5/2007 | Carley et al. | |
| 7,316,704 B2 | 1/2008 | Bagaoisan et al. | |
| 7,326,230 B2 | 2/2008 | Ravikumar | |
| 7,331,979 B2 | 2/2008 | Khosravi et al. | |
| 7,335,220 B2 | 2/2008 | Khosravi et al. | |
| D566,272 S | 4/2008 | Walberg et al. | |
| 7,361,183 B2 | 4/2008 | Ginn | |
| 7,361,185 B2 | 4/2008 | O'Malley et al. | |
| 7,393,363 B2 | 7/2008 | Ginn | |
| 7,396,359 B1 | 7/2008 | Derowe et al. | |
| 7,533,790 B1 | 5/2009 | Knodel et al. | |
| 7,597,706 B2 | 10/2009 | Kanner et al. | |
| D611,144 S | 3/2010 | Reynolds | |
| 2001/0007077 A1 | 7/2001 | Ginn et al. | |
| 2001/0031972 A1 | 10/2001 | Robertson et al. | |
| 2001/0046518 A1 | 11/2001 | Sawhney | |
| 2001/0047180 A1 | 11/2001 | Grudem et al. | 606/153 |
| 2002/0026208 A1 * | 2/2002 | Roe et al. | 606/190 |
| 2002/0026215 A1 | 2/2002 | Redmond et al. | |
| 2002/0038127 A1 | 3/2002 | Blatter et al. | |
| 2002/0042622 A1 | 4/2002 | Vargas et al. | |
| 2002/0049427 A1 | 4/2002 | Wiener et al. | |

| | | | | | | |
|---|---|---|---|---|---|---|
| 2002/0049472 A1 | 4/2002 | Coleman et al. | | 2006/0020270 A1 | 1/2006 | Jabba et al. |
| 2002/0058960 A1 | 5/2002 | Hudson et al. | | 2006/0034930 A1 | 2/2006 | Khosravi et al. |
| 2002/0072768 A1 | 6/2002 | Ginn | | 2006/0047313 A1 | 3/2006 | Khanna et al. |
| 2002/0077657 A1 | 6/2002 | Ginn et al. | | 2006/0100664 A1 | 5/2006 | Pai et al. |
| 2002/0082641 A1 | 6/2002 | Ginn et al. ............... 606/213 | | 2006/0135989 A1 | 6/2006 | Carley et al. |
| 2002/0099389 A1 | 7/2002 | Michler et al. | | 2006/0144479 A1 | 7/2006 | Carley et al. |
| 2002/0106409 A1 | 8/2002 | Sawhney et al. | | 2006/0167484 A1 | 7/2006 | Carley et al. |
| 2002/0107542 A1 | 8/2002 | Kanner et al. | | 2006/0190014 A1 | 8/2006 | Ginn et al. |
| 2002/0133193 A1 | 9/2002 | Ginn et al. | | 2006/0190038 A1 | 8/2006 | Carley et al. |
| 2002/0151921 A1 | 10/2002 | Kanner et al. | | 2006/0195123 A1 | 8/2006 | Ginn et al. |
| 2002/0188318 A1 | 12/2002 | Carleyt et al. ............... 606/213 | | 2006/0195124 A1 | 8/2006 | Ginn et al. |
| 2002/0193808 A1 | 12/2002 | Belef et al. | | 2006/0253037 A1 | 11/2006 | Ginn et al. |
| 2003/0004543 A1 | 1/2003 | Gleeson et al. | | 2006/0253072 A1 | 11/2006 | Pai et al. |
| 2003/0009180 A1 | 1/2003 | Hinchliffe et al. | | 2006/0265012 A1 | 11/2006 | Anderson |
| 2003/0009196 A1 | 1/2003 | Peterson | | 2006/0287674 A1 | 12/2006 | Ginn et al. |
| 2003/0032981 A1 | 2/2003 | Kanner et al. | | 2007/0010853 A1 | 1/2007 | Ginn et al. |
| 2003/0065358 A1 | 4/2003 | Frecker et al. | | 2007/0010854 A1 | 1/2007 | Cummins et al. |
| 2003/0078598 A1 | 4/2003 | Ginn et al. | | 2007/0021778 A1 | 1/2007 | Carly |
| 2003/0083679 A1 | 5/2003 | Grudem et al. | | 2007/0049967 A1 | 3/2007 | Sibbitt, Jr. et al. |
| 2003/0093096 A1 | 5/2003 | McGuckin et al. | | 2007/0049968 A1 | 3/2007 | Sibbitt, Jr. et al. |
| 2003/0097140 A1 | 5/2003 | Kanner | | 2007/0060895 A1 | 3/2007 | Sibbitt, Jr. et al. |
| 2003/0109890 A1 | 6/2003 | Kanner et al. | | 2007/0060950 A1 | 3/2007 | Khosravi et al. |
| 2003/0125766 A1 | 7/2003 | Ding | | 2007/0123817 A1 | 5/2007 | Khosravi et al. |
| 2003/0158577 A1 | 8/2003 | Pantages et al. | | 2007/0203506 A1 | 8/2007 | Sibbitt, Jr. et al. |
| 2003/0158578 A1 | 8/2003 | Pantages et al. | | 2007/0250080 A1 | 10/2007 | Jones et al. |
| 2003/0195504 A1 | 10/2003 | Tallarida et al. | | 2008/0004636 A1 | 1/2008 | Walberg |
| 2003/0195561 A1 | 10/2003 | Carley et al. | | 2008/0009794 A1 | 1/2008 | Bagaoisan et al. |
| 2004/0009205 A1 | 1/2004 | Sawhney | | 2008/0065151 A1 | 3/2008 | Ginn |
| 2004/0009289 A1 | 1/2004 | Carley et al. | | 2008/0065152 A1 | 3/2008 | Carley |
| 2004/0010285 A1 | 1/2004 | Carley et al. ............... 606/213 | | 2008/0086075 A1 | 4/2008 | Isik et al. |
| 2004/0039414 A1 | 2/2004 | Carley et al. ............... 606/213 | | 2008/0221616 A1 | 9/2008 | Ginn et al. |
| 2004/0073236 A1 | 4/2004 | Carley et al. | | 2008/0312686 A1 | 12/2008 | Ellingwood |
| 2004/0073255 A1 | 4/2004 | Ginn et al. | | 2008/0319475 A1 | 12/2008 | Clark |
| 2004/0082906 A1 | 4/2004 | Tallarida et al. | | 2009/0157101 A1 | 6/2009 | Reyes et al. |
| 2004/0087985 A1 | 5/2004 | Loshakove et al. | | 2009/0157102 A1 | 6/2009 | Reynolds et al. |
| 2004/0092964 A1 | 5/2004 | Modesitt et al. | | 2009/0157103 A1 | 6/2009 | Walberg et al. |
| 2004/0092968 A1 | 5/2004 | Caro et al. | | 2009/0254119 A1 | 10/2009 | Sibbitt, Jr. et al. |
| 2004/0093027 A1 | 5/2004 | Fabisiak et al. | | 2010/0130965 A1 | 5/2010 | Sibbitt, Jr. |
| 2004/0097978 A1 | 5/2004 | Modesitt et al. | | | | |
| 2004/0127940 A1 | 7/2004 | Ginn et al. | | FOREIGN PATENT DOCUMENTS | | |
| 2004/0143290 A1 | 7/2004 | Brightbill | | DE | 197 11 288 | 1/1998 |
| 2004/0153122 A1 | 8/2004 | Palermo | | DE | 297 23 736 U 1 | 4/1999 |
| 2004/0158127 A1 | 8/2004 | Okada | | DE | 19859952 | 2/2000 |
| 2004/0158287 A1 | 8/2004 | Cragg et al. | | EP | 0 386 361 | 9/1990 |
| 2004/0167511 A1 | 8/2004 | Buehlmann et al. | | EP | 0 534 696 | 3/1993 |
| 2004/0167570 A1 | 8/2004 | Pantages | | EP | 0 756 851 | 2/1997 |
| 2004/0191277 A1 | 9/2004 | Sawhney et al. | | EP | 0 774 237 | 5/1997 |
| 2004/0215232 A1 | 10/2004 | Belhe et al. | | EP | 0 858 776 | 8/1998 |
| 2004/0254591 A1 | 12/2004 | Kanner et al. | | EP | 0 941 697 | 9/1999 |
| 2004/0267193 A1 | 12/2004 | Bagaoisan et al. | | FR | 2 443 238 | 7/1980 |
| 2004/0267308 A1 | 12/2004 | Bagaoisan et al. | | FR | 2 715 290 | 7/1995 |
| 2004/0267312 A1 | 12/2004 | Kanner et al. | | FR | 2 722 975 | 2/1996 |
| 2005/0059982 A1 | 3/2005 | Zung et al. | | FR | 2 768 324 | 3/1999 |
| 2005/0075665 A1 | 4/2005 | Brenzel et al. | | GB | 1 358 466 | 7/1974 |
| 2005/0085851 A1 | 4/2005 | Fiehler et al. | | GB | 2 075 144 | 11/1981 |
| 2005/0085854 A1 | 4/2005 | Ginn | | IE | S 2000/0722 | 10/2001 |
| 2005/0085855 A1 | 4/2005 | Forsberg | | IE | S 2000/0724 | 10/2001 |
| 2005/0090859 A1 | 4/2005 | Ravlkumar | | IE | S 2001/0547 | 7/2002 |
| 2005/0119695 A1 | 6/2005 | Carley et al. | | IE | S 2001/0815 | 7/2002 |
| 2005/0121042 A1 | 6/2005 | Belhe et al. | | IE | S 2001/0748 | 8/2002 |
| 2005/0149117 A1 | 7/2005 | Khosravi et al. | | IE | S 2001/0749 | 8/2002 |
| 2005/0165357 A1 | 7/2005 | McGuckin et al. | | IE | S 2002/0452 | 12/2002 |
| 2005/0177189 A1 | 8/2005 | Ginn et al. | | IE | S 2002/0664 | 2/2003 |
| 2005/0216057 A1 | 9/2005 | Coleman et al. | | IE | S 2002/0665 | 2/2003 |
| 2005/0222614 A1 | 10/2005 | Ginn et al. | | IE | S 2002/0451 | 7/2003 |
| 2005/0234508 A1 | 10/2005 | Cummins et al. | | IE | S 2002/0552 | 7/2003 |
| 2005/0245876 A1 | 11/2005 | Khosravi et al. | | IE | S 2005/0342 | 11/2003 |
| 2005/0267528 A1 | 12/2005 | Ginn et al. | | IE | S 2003/0424 | 12/2003 |
| 2005/0267530 A1 | 12/2005 | Cummins et al. | | IE | S 2003/0490 | 1/2004 |
| 2005/0273136 A1 | 12/2005 | Belef et al. | | IE | S 2004/0368 | 11/2005 |
| 2005/0273137 A1 | 12/2005 | Ginn | | JP | 58-181006 | 12/1983 |
| 2005/0274768 A1 | 12/2005 | Cummins et al. | | JP | 12 74750 | 11/1989 |
| 2005/0283188 A1 | 12/2005 | Loshakove et al. | | | | |

| | | |
|---|---|---|
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/94748 | 11/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 | 3/2008 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

PCT Publication No. WO 00/56227, entitled "Advanced Closure Device", Sep. 28, 2000.
PCT Publication No. WO 00/56223 entitled "Vascular Closure Device", Sep. 28, 2000.
PCT Publication No. WO 99/62408 entitled "Vascular Port Device", Dec. 9, 1999.
PCT Publication No. WO 98/24374, "Vascular Wound Closure System", Yong Zhu, et al., Jun. 11, 1998.
PCT Publication No. WO 97/20505, "Vascular Wound Closure Device", Yong Zhu, et al., Jun. 12, 1997.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Database WPI; Section PQ, Week 200120; Derwent Publications Ltd., London GB; AN 2001-203165; XP002199926 & ZA 200 100 528 A (Anthony T), Feb. 28, 2001 abstract.
Stretch Comb by Scunci, retrieved via internet at www.scunci.com/productdetail by Examiner on Oct. 9, 2007, publication date unavailable.
2002/0072768, Office Action, Mail Date Aug. 27, 2004.
2002/0072768, Office Action, Mail Date Feb. 23, 2005.
2002/0072768, Office Action, Mail Date Apr. 11, 2005.
2002/0072768, Office Action, Mail Date Jul. 27, 2005.
2002/0072768, Office Action, Mail Date Mar. 6, 2006.
2002/0072768, Office Action, Mail Date May 24, 2006.
2002/0072768, Office Action, Mail Date Oct. 26, 2006.
2002/0072768, Office Action, Mail Date Apr. 19, 2007.
2002/0133193, Office Action, Mail Date Nov. 4, 2004.
2002/0133193, Office Action, Mail Date May 4, 2005.
2002/0133193, Office Action, Mail Date Oct. 18, 2005.
2002/0133193, Notice of Allowance, Mail Date Apr. 18, 2007.
2002/0133193, Notice of Allowance, Mail Date Sep. 27, 2007.
2003/0078598, Office Action, Mail Date Feb. 9, 2005.
2003/0078598, Office Action, Mail Date May 26, 2005.
2003/0078598, Office Action, Mail Date Oct. 4, 2005.
2003/0078598, Notice of Allowance, Mail Date May 10, 2006.
2003/0078598, Notice of Allowance, Mail Date Jul. 2, 2007.
2003/0195561, Office Action, Mail Date Jun. 10, 2004.
2003/0195561, Notice of Allowance, Mail Date Sep. 21, 2004.
2003/0195561, Office Action, Mail Date Jan. 3, 2006.
2003/0195561, Issue Notification, Mail Date Feb. 15, 2006.
2003/0195561, Office Action, Mail Date May 16, 2006.
2003/0195561, Notice of Allowance, Mail Date Dec. 28, 2006.
2003/0195561, Notice of Allowance, Mail Date Jul. 10, 2007.
2003/0195561, Notice of Allowance, Mail Date Aug. 2, 2007.
2004/0153122, Office Action, Mail Date Nov. 30, 2005.
2004/0153122, Office Action, Mail Date Aug. 23, 2006.
2004/0153122, Office Action, Mail Date Feb. 13, 2007.
2004/0153122, Office Action, Mail Date Sep. 12, 2007.
2004/0073255, Office Action, Mail Date Sep. 15, 2006.
2004/0073255, Office Action, Mail Date Apr. 18, 2007.
2004/0073236, Office Action, Mail Date Sep. 19, 2006.
2004/0073236, Office Action, Mail Date May 2, 2007.

2004/0009289, Office Action, Mail Date Jun. 30, 2006.
2004/0009289, Office Action, Mail Date Oct. 20, 2006.
2004/0009289, Office Action, Mail Date May 29, 2007.
2004/0167570, Office Action, Mail Date Oct. 30, 2006.
2004/0167570, Office Action, Mail Date Apr. 17, 2007.
2004/0167570, Office Action, Mail Date Aug. 31, 2007.
2005/0274768, Office Action, Mail Date Oct. 19, 2006.
2005/0274768, Office Action, Mail Date Aug. 10, 2007.
2005/0216057, Office Action, Mail Date Feb. 6, 2007.
2005/0216057, Office Action, Mail Date May 30, 2007.
2005/0234508, Office Action, Mail Date Aug. 13, 2007.
2006/0135989, Office Action, Mail Date Nov. 30, 2006.
2006/0135989, Office Action, Mail Date Sep. 5, 2007.
2006/0195124, Office Action, Mail Date Jun. 6, 2007.
2006/0195123, Office Action, Mail Date May 14, 2007.
6,197,042, Notice of Allowance, Mail Date Nov. 6, 2000.
6,197,042, Issue Notification, Mail Date Feb. 15, 2001.
6,277,140, Office Action, Mail Date Mar. 26, 2001.
6,277,140, Notice of Allowance, Mail Date Jun. 4, 2001.
6,277,140, Issue Notification, Mail Date Aug. 6, 2001.
6,391,048, Notice of Allowance, Mail Date Mar. 26, 2001.
6,391,048, Office Action, Mail Date Sep. 5, 2001.
6,391,048, Notice of Allowance, Mail Date Feb. 11, 2002.
6,391,048, Issue Notification, Mail Date May 3, 2002.
6,461,364, Notice of Allowance, Mail Date May 6, 2002.
6,461,364, Issue Notification, Mail Date Sep. 19, 2002.
6,582,452, Notice of Allowance, Mail Date Jan. 31, 2003.
6,582,452, Issue Notification, Mail Date Jun. 5, 2003.
6,616,686, Office Action, Mail Date Dec. 17, 2002.
6,616,686, Notice of Allowance, Mail Date Apr. 21, 2003.
6,616,686, Issue Notification, Mail Date Aug. 21, 2003.
6,623,510, Notice of Allowance, Mail Date Apr. 11, 2003.
6,623,510, Office Action, Mail Date Jun. 9, 2003.
6,623,510, Issue Notification, Mail Date Sep. 4, 2003.
6,632,238, Office Action, Mail Date Feb. 26, 2003.
6,632,238, Notice of Allowance, Mail Date Jun. 16, 2003.
6,632,238, Issue Notification, Mail Date Sep. 25, 2003.
6,669,714, Office Action, Mail Date Mar. 4, 2003.
6,669,714, Notice of Allowance, Mail Date Jul. 28, 2003.
6,669,714, Issue Notification, Mail Date Dec. 11, 2003.
6,695,867, Notice of Allowance, Mail Date Sep. 29, 2003.
6,695,867, Issue Notification, Mail Date Feb. 5, 2004.
6,719,777, Office Action, Mail Date Feb. 20, 1987.
6,719,777, Notice of Allowance, Mail Date Jul. 24, 1987.
6,719,777, Issue Notification, Mail Date Mar. 25, 2004.
6,749,621, Notice of Allowance, Mail Date Feb. 9, 2004.
6,749,621, Office Action, Mail Date Apr. 13, 2004.
6,749,621, Issue Notification, Mail Date May 27, 2004.
6,780,197, Office Action, Mail Date Sep. 11, 2003.
6,780,197, Office Action, Mail Date Feb. 9, 2004.
6,780,197, Notice of Allowance, Mail Date Mar. 17, 2004.
6,780,197, Issue Notification, Mail Date Aug. 5, 2004.
6,926,731, Office Action, Mail Date Nov. 16, 2004.
6,926,731, Notice of Allowance, Mail Date Apr. 6, 2005.
6,926,731, Issue Notification, Mail Date Jul. 20, 2005.
6,942,674, Office Action, Mail Date Sep. 29, 2004.
6,942,674, Notice of Allowance, Mail Date May 13, 2005.
6,942,674, Issue Notification, Mail Date Aug. 24, 2005.
7,001,398, Office Action, Mail Date Mar. 22, 2005.
7,001,398, Notice of Allowance, Mail Date Jul. 6, 2005.
7,001,398, Notice of Allowance, Mail Date Oct. 5, 2005.
7,001,398, Issue Notification, Mail Date Feb. 21, 2006.
7,008,435, Office Action, Mail Date Apr. 20, 2005.
7,008,435, Office Action, Mail Date Aug. 10, 2005.
7,008,435, Notice of Allowance, Mail Date Oct. 18, 2005.
7,008,435, Issue Notification, Mail Date Feb. 15, 2006.
7,108,709, Office Action, Mail Date Jul. 27, 2004.
7,108,709, Office Action, Mail Date Dec. 17, 2004.
7,108,709, Notice of Allowance, Mail Date Mar. 9, 2005.
7,108,709, Office Action, Mail Date Aug. 11, 2006.
7,108,709, Issue Notification, Mail Date Aug. 30, 2006.
7,111,768, Office Action, Mail Date Feb. 23, 2006.
7,111,768, Notice of Allowance, Mail Date May 31, 2006.
7,111,768, Issue Notification, Mail Date Sep. 6, 2006.
7,163,551, Office Action, Mail Date Jan. 10, 2006.
7,163,551, Notice of Allowance, Mail Date Sep. 20, 2006.
7,163,551, Issue Notification, Mail Date Dec. 27, 2006.
7,211,101, Office Action, Mail Date Aug. 10, 2005.
7,211,101, Office Action, Mail Date Dec. 19, 2005.
7,211,101, Office Action, Mail Date Apr. 21, 2006.
7,211,101, Notice of Allowance, Mail Date Dec. 27, 2006.
7,211,101, Issue Notification, Mail Date Apr. 11, 2007.
U.S. Appl. No. 10/541,083, Office Action, Mail Date Oct. 16, 2007.
"Hand tool for forming telephone connections—comprises pliers with reciprocably driven ram crimping clip around conductors against anvil", Derwent-ACC-No. 1978-B8090A.
U.S. Appl. No 10/006,400, filed Apr. 2, 2008, Office Action.
U.S. Appl. No. 10/147,774, filed Feb. 4, 2008, Notice of Allowance.
U.S. Appl. No. 10/264,306, filed May 26, 2005, Office Action.
U.S. Appl. No. 10/264,306, filed Feb. 4, 2008, Notice of Allowance.
U.S. Appl. No. 10/264,306, filed Jun. 27, 2008, Office Action.
U.S. Appl. No. 10/356,214, filed Mar. 6, 2008, Office Action.
U.S. Appl. No. 10/435,104, filed Apr. 4, 2008, Notice of Allowance.
U.S. Appl. No. 10/517,004, filed Jan. 30, 2008, Office Action.
U.S. Appl. No. 10/541,083, filed May 5, 2008, Office Action.
U.S. Appl. No. 10/667,144, filed May 12, 2008, Office Action.
U.S. Appl. No. 10/682,459, filed Apr. 2, 2008, Office Action.
U.S. Appl. No. 10/786,444, filed Apr. 24, 2008, Office Action.
U.S. Appl. No. 10/787,073, filed Feb. 22, 2008, Office Action.
U.S. Appl. No. 11/113,549, filed Apr. 16, 2008, Office Action.
U.S. Appl. No. 11/152,562, filed May 13, 2008, Office Action.
U.S. Appl. No. 11/344,891, filed Apr. 29, 2008, Office Action.
U.S. Appl. No. 11/406,203, filed May 23, 2008, Notice of Allowance.
U.S. Appl. No. 11/411,925, filed Feb. 5, 2008, Office Action.
U.S. Appl. No. 60/696,069, filed Jul. 1, 2005, Pantages et al.
U.S. Appl. No. 60/946,026, filed Jun. 25, 2007, Ellingwood.
McCarthy, et al., "Tension (Stay) Suture Bridge", J. of International College of Surgeons, 34(5), pp. 613-614 (Nov. 1960). cited by other.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials And Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov.

1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

McCarthy, et al., "Tension (Stay) Suture Bridge", J. of International College of Surgeons, 34(5), pp. 613-614 (Nov. 1960).

U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice of Allowance.
U.S. Appl. No. 09/680,837, Mail Date Sep. 11, 2003, Issue Notification.
U.S. Appl. No. 10/006,400, Mail Date Jul. 9, 2009, Notice of Allowance.
U.S. Appl. No. 10/027,681, Mail Date Jul. 8, 2009, Office Action.
U.S. Appl. No. 10/356,214, Mail Date Apr. 29, 2009, Office Action.
U.S. Appl. No. 10/517,004, Mail Date Jun. 26, 2009, Notice of Allowance.
U.S. Appl. No. 10/541,083, Mail Date Apr. 16, 2009, Notice of Allowance.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/669,313, Mail Date Nov. 15, 2006, Issue Notification.
U.S. Appl. No. 10/682,459, Mail Date Jun. 10, 2009, Office Action.
U.S. Appl. No. 10/786,444, Mail Date Jun. 18, 2009, Office Action.
U.S. Appl. No. 10/908,721, Mail Date Jun. 23, 2009, Office Action.
U.S. Appl. No. 11/048,503, Mail Date Jun. 26, 2009, Office Action.
U.S. Appl. No. 11152,562, Mail Date Jul. 6, 2009, Office Action.
U.S. Appl. No. 11/396,141, Mail Date May 22, 2009, Office Action.
U.S. Appl. No. 11/396,731, Mail Date May 22, 2009, Office Action.
U.S. Appl. No. 11/532,325, Mail Date Feb. 23, 2009, Office Action.
U.S. Appl. No. 11/532,325, Mail Date Jun. 17, 2009, Office Action.
U.S. Appl. No. 29/296,370, Mail Date Apr. 1, 2009, Notice of Allowance.
U.S. Appl. No. 60/693,531, filed Jun. 24, 2005, Carly.

Marshall A.C., Lock J.E., Structural and Compliant Anatomy of the Patent Foramen Ovale in Patients Undergoing Transcatheter Closure, Am Heart J 2000 Aug; 140(2); pp. 303-307.

Taber's Cyclopedic Medical Dictionary, 18th Ed. 1997, pp. 747 and 1420.

U.S. Appl. No. 10/006,400, Mail Date Jan. 13, 2010, Notice of Allowance.
U.S. Appl. No. 10/147,774, Mail Date Oct. 26, 2009, Office Action.
U.S. Appl. No. 10/264,306, Mail Date Aug. 13, 2009, Office Action.
U.S. Appl. No. 10/356,214, Mail Date Jan. 13, 2010, Notice of Allowance.
U.S. Appl. No. 10/435,104, Mail Date Jan. 20, 2010, Notice of Allowance.
U.S. Appl. No. 10/517,004, Mail Date Jan. 11, 2010, Notice of Allowance.
U.S. Appl. No. 10/541,083, Mail Date Feb. 5, 2010, Notice of Allowance.
U.S. Appl. No. 10/616,832, Mail Date Jan. 11, 2010, Notice of Allowance.
U.S. Appl. No. 10/541,083, Mail Date Sep. 30, 2009, Notice of Allowance.
U.S. Appl. No. 10/616,832, Mail Date Jul. 21, 2009, Office Action.
U.S. Appl. No. 10/667,144, Mail Date Nov. 23, 2009, Office Action.
U.S. Appl. No. 10/682,459, Mail Date Dec. 23, 2009, Office Action.
U.S. Appl. No. 10/786,444, Mail Date Jan. 14, 2010, Office Action.

U.S. Appl. No. 10/787,073, Mail Date Aug. 13, 2009, Office Action.
U.S. Appl. No. 10/787,073, Mail Date Feb. 17, 2010, Notice of Allowance.
U.S. Appl. No. 11/048,503, Mail Date Jan. 11, 2010, Notice of Allowance.
U.S. Appl. No. 11/113,549, Mail Date Jul. 21, 2009, Office Action.
U.S. Appl. No. 11/198,811, Mail Date Sep. 22, 2009, Office Action.
U.S. Appl. No. 11/344,891, Mail Date Oct. 7, 2009, Office Action.
U.S. Appl. No. 11/396,141, Mail Date Aug. 26, 2009, Office Action.
U.S. Appl. No. 11/406,203, Mail Date Sep. 16, 2009, Office Action.
U.S. Appl. No. 11/411,925, Mail Date Sep. 10, 2009, Office Action.
U.S. Appl. No. 11/427,297, Mail Date Sep. 15, 2009, Office Action.
U.S. Appl. No. 11/455,993, Mail Date Feb. 17, 2009, Office Action.
U.S. Appl. No. 11/455,993, Mail Date Dec. 16, 2009, Office Action.
U.S. Appl. No. 11/461,323, Mail Date Jul. 27, 2009, Office Action.
U.S. Appl. No. 11/532,325, Mail Date Jan. 5, 2010, Office Action.
U.S. Appl. No. 11/675,462, Mail Date Dec. 10, 2009, Office Action.
U.S. Appl. No. 11/744,089, Mail Date Aug. 14, 2009, Office Action.
U.S. Appl. No. 11/958,295, Mail Date Aug. 27, 2009, Office Action.
U.S. Appl. No. 11/959,334, Mail Date Aug. 19, 2009, Office Action.
U.S. Appl. No. 11/959,334, Mail Date Jan. 12, 2010, Notice of Allowance.
U.S. Appl. No. 12/106,937, Mail Date Nov. 18, 2009, Office Action.
U.S. Appl. No. 12/106,928, Mail Date Oct. 5, 2009, Office Action.
U.S. Appl. No. 12/403,256, Mail Date Dec. 16, 2009, Restriction Requirement.
U.S. Appl. No. 29/296,370, Mail Date Feb. 10, 2010, Issue Notification.
U.S. Appl. No. 60/711,279, filed Aug. 24, 2005, Sibbitt Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 61/097,072, filed Sep. 15, 2008, Sibbitt, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, Mail Date on Apr. 27, 2010, Notice of Allowance.
U.S. Appl. No. 10/264,306, Mail Date Jan. 27, 2010, Office Action.
U.S. Appl. No. 10/356,214, Mail Date May 13, 2010, Notice of Allowance.
U.S. Appl. No. 10/517,004, Mail Date Apr. 23, 2010, Notice of Allowance.
U.S. Appl. No. 10/541,083, Mail Date May 10, 2010, Notice of Allowance.
U.S. Appl. No. 10/616,832, Mail Date May 12, 2010, Notice of Allowance.
U.S. Appl. No. 10/682,459, Mail Date Apr. 28, 2010, Office Action.
U.S. Appl. No. 10/908,721, Mail Date Feb. 2, 2010, Office Action.
U.S. Appl. No. 11/048,503, Mail Date Apr. 26, 2010, Notice of Allowance.
U.S. Appl. No. 11/152,562, Mail Date Mar. 31, 2010, Office Action.
U.S. Appl. No. 11/316,775, Mail Date Apr. 16, 2008, Office Action.
U.S. Appl. No. 11/316,775, Mail Date Aug. 6, 2008, Office Action.
U.S. Appl. No. 11/344,891, Mail Date May 7, 2010, Office Action.
U.S. Appl. No. 11/390,586, Mail Date Jun. 24, 2009, Office Action.
U.S. Appl. No. 11/396,141, Mail Date May 4, 2010, Office Action.
U.S. Appl. No. 11/406,203, Mail Date Jun. 18, 2010, Notice of Allowance.
U.S. Appl. No. 11/508,656, Mail Date Dec. 9, 2009, Office Action.
U.S. Appl. No. 11/508,656, Mail Date Mar. 25, 2010, Office Action.
U.S. Appl. No. 11/508,662, Mail Date Dec. 28, 2009, Office Action.
U.S. Appl. No. 11/508,662, Mail Date Apr. 14, 2010, Office Action.
U.S. Appl. No. 11/508,715, Mail Date Jan. 6, 2010, Office Action.
U.S. Appl. No. 11/508,715, Mail Date Apr. 26, 2010, Office Action.
U.S. Appl. No. 11/532,576, Mail Date Mar. 1, 2010, Office Action.
U.S. Appl. No. 11/532,576, Mail Date Apr. 23, 2010, Office Action.
U.S. Appl. No. 11/674,930, Mail Date Jan. 8, 2009, Office Action.
U.S. Appl. No. 11/674,930, Mail Date Jun. 4, 2009, Office Action.
U.S. Appl. No. 11/674,930, Mail Date Jan. 8, 2010, Office Action.
U.S. Appl. No. 11/958,295, Mail Date May 25, 2010, Office Action.
U.S. Appl. No. 11/959,334, Mail Date Apr. 14, 2010, Notice of Allowance.
U.S. Appl. No. 12/106,928, Mail Date May 10, 2010, Office Action.
U.S. Appl. No. 12/113,851, Mail Date Apr. 27, 2010, Office Action.
U.S. Appl. No. 12/402,398, Mail Date Mar. 9, 2010, Office Action.
U.S. Appl. No. 12/402,398, Mail Date May 20, 2010, Office Action.
U.S. Appl. No. 12/403,256, Mail Date Mar. 30, 2010, Office Action.
U.S. Appl. No. 11/198,811, Mail Date Jun. 29, 2010, Notice of Allowance.
U.S. Appl. No. 11/767,818, Mail Date Dec. 24, 2009, Restriction Requirement.
U.S. Appl. No. 11/678,818, Mail Date Mar. 22, 2010, Office Action.
U.S. Appl. No. 10/435,104, Mail Date Jul. 23, 2009, Notice of Allowance.
U.S. Appl. No. 10/669,313, Mail Date Oct. 31, 2005, Office Action.
U.S. Appl. No. 11/113,549, Mail Date Jul. 6, 2010, Office Action.
U.S. Appl. No. 11/959,334, Mail Date Jul. 23, 2010, Notice of Allowance.
U.S. Appl. No. 12/403,277, Mail Date Jul. 8, 2010, Office Action.
U.S. Appl. No. 10/147,774, Mail Date Jun. 8, 2010, Office Action.
U.S. Appl. No. 10/264,306, Mail Date Jun. 15, 2010, Office Action.
U.S. Appl. No. 10/435,104 Mail Date Jun. 2, 2010, Office Action.
U.S. Appl. No. 10/667,144 Mail Date Jun. 22, 2010, Office Action.
U.S. Appl. No. 11/390,586, Mail Date Jul. 6, 2010, Office Action.
U.S. Appl. No. 11/396,731, Mail Date Jun. 29, 2010, Office Action.
U.S. Appl. No. 11/852,190, Mail Date Jun. 24, 2010, Office Action.
U.S. Appl. No. 12/113,851, Mail Date Jun. 24, 2010, Office Action.

* cited by examiner

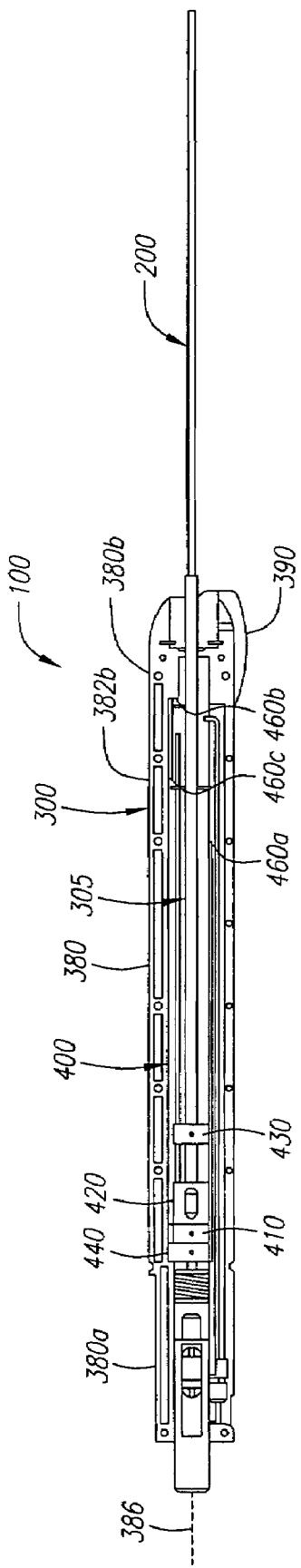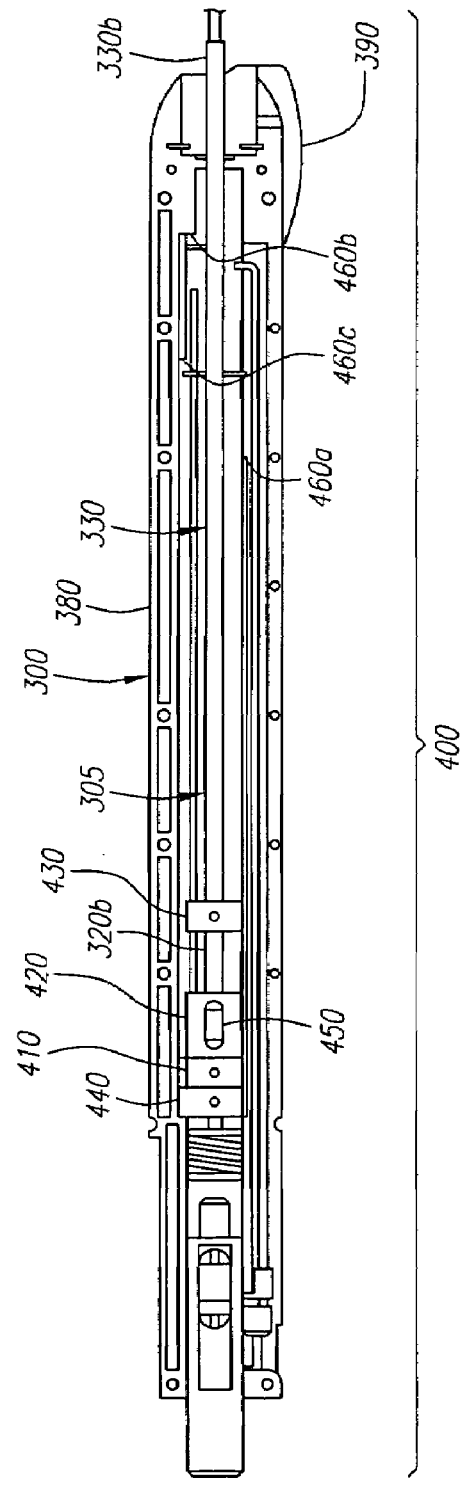
FIG. 4A
FIG. 4B

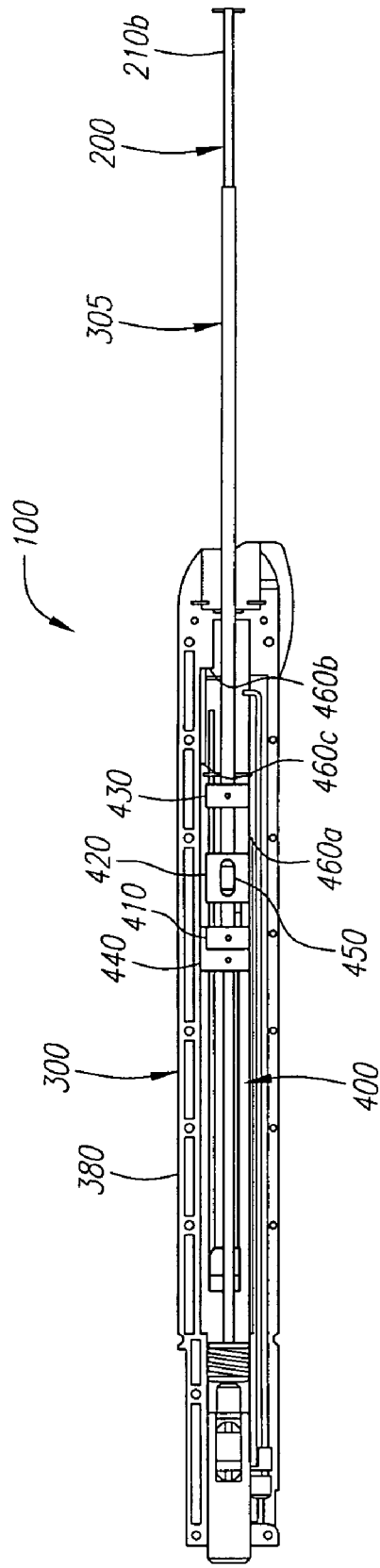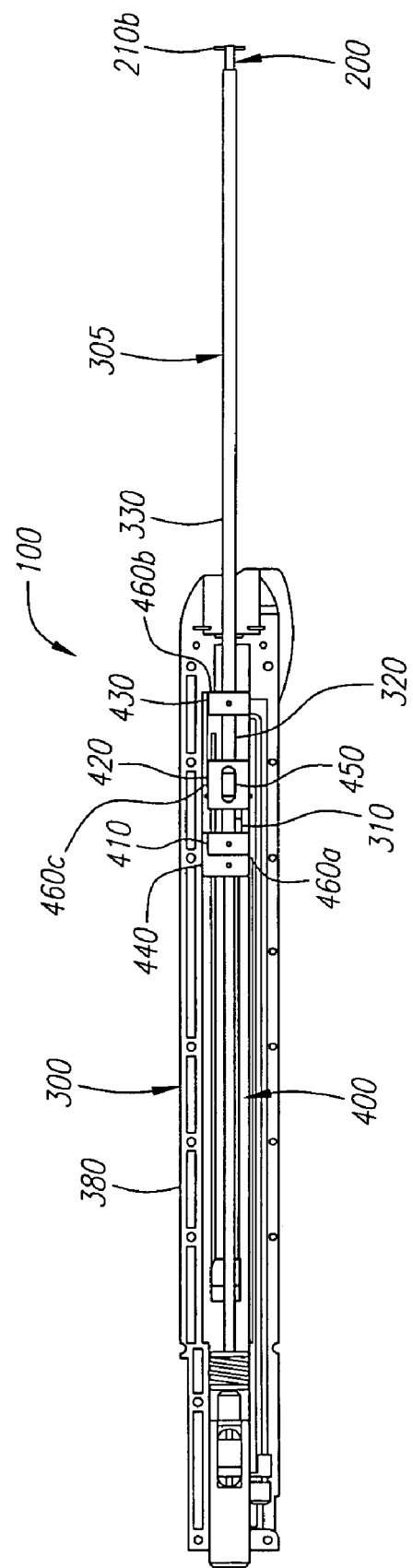
FIG. 5A
FIG. 5B

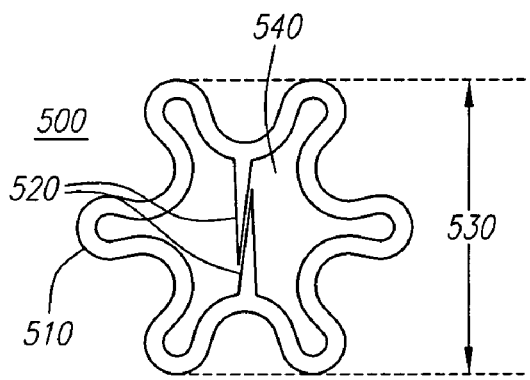
FIG. 6A
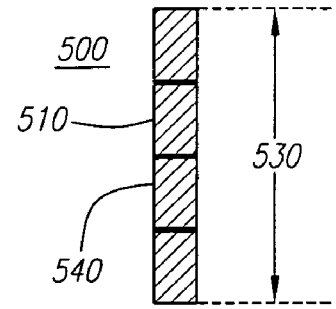
FIG. 6B
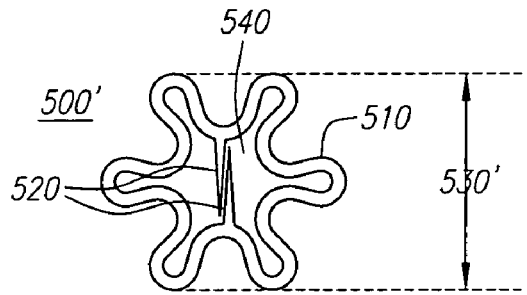
FIG. 6C
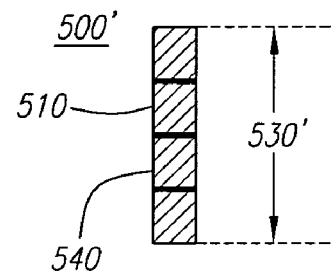
FIG. 6D
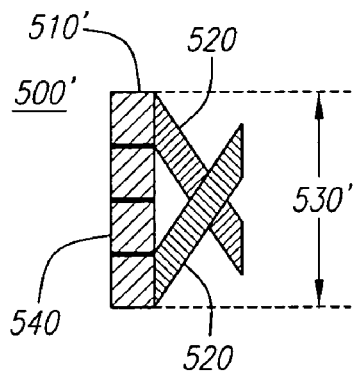
FIG. 6E
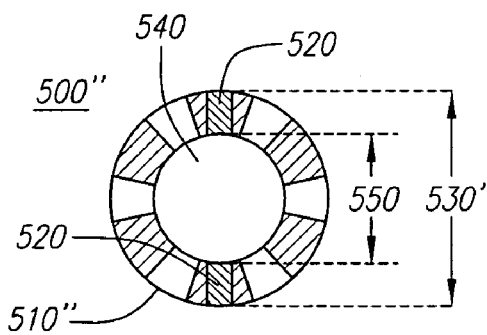
FIG. 6F
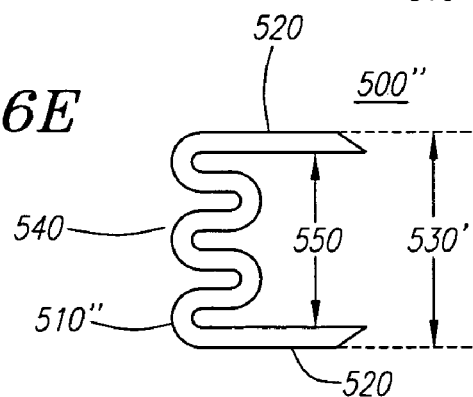

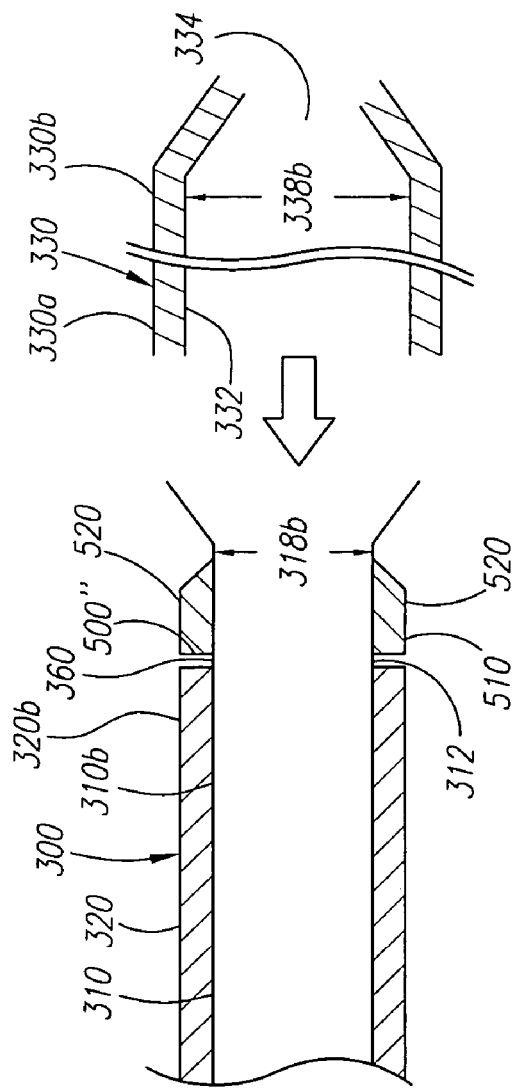
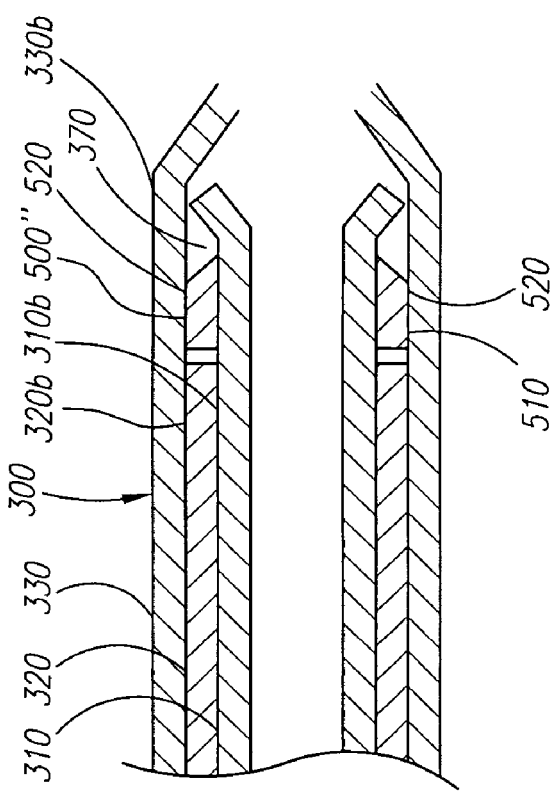
FIG. 7C
FIG. 7D

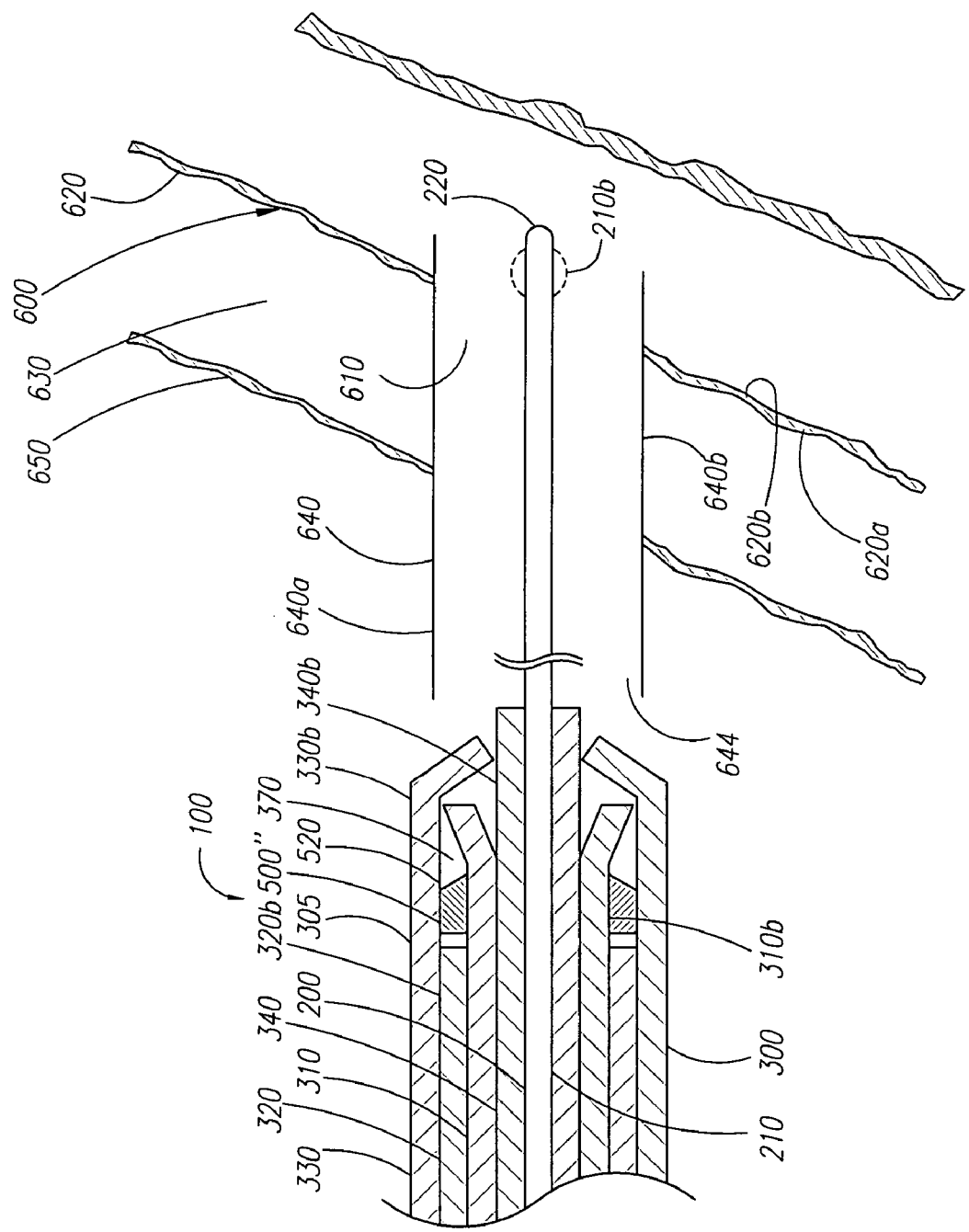

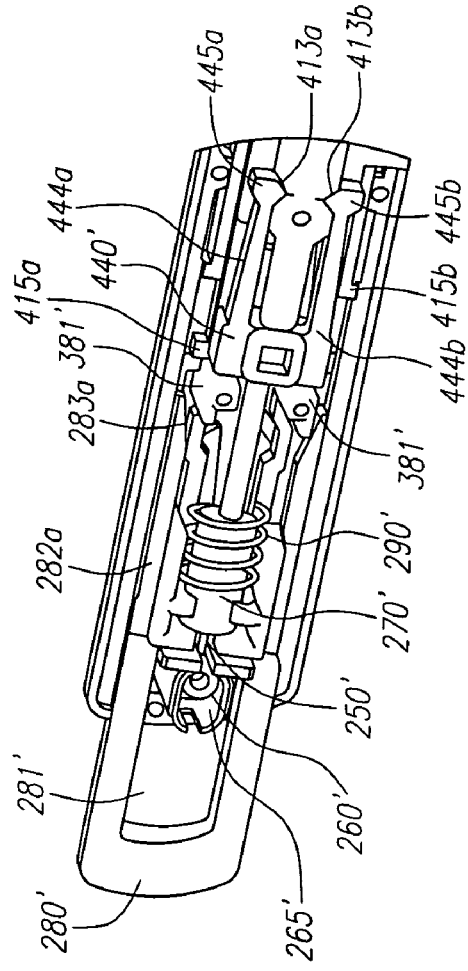
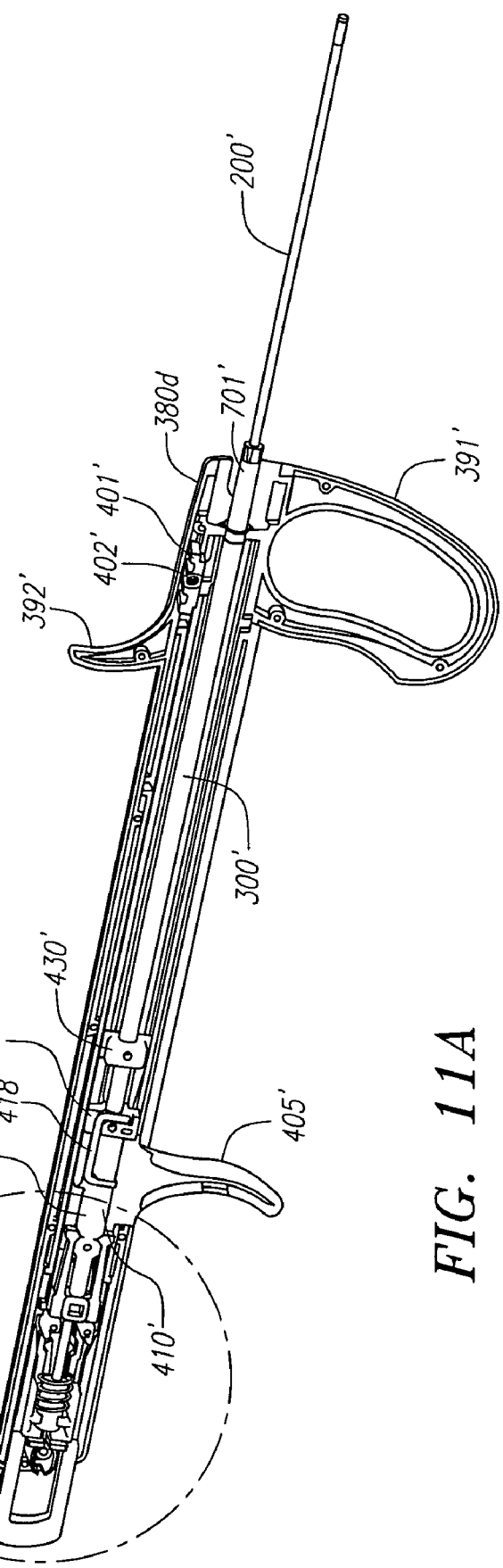
FIG. 11B
FIG. 11A

CLIP APPLIER AND METHODS OF USE

CROSS-REFERENCE OF RELATED APPLICATION

This application is a continuation-in-part of U.S. patent application Ser. No. 10/356,214, filed Jan. 30, 2003 which is incorporated herein by reference.

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle then is removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, apparatus and methods for delivering a device for closing a vascular puncture site or other opening through tissue would be useful.

SUMMARY OF THE INVENTION

The present invention is directed toward an apparatus and method for delivering a closure element through tissue and into an opening formed in, or adjacent to, a wall of a blood vessel or other body lumen of any size.

The apparatus is configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus preferably is configured to substantially uniformly expand the closure element beyond a natural cross-section of the closure element such that the closure element, when deployed, is configured to engage significant amount of the blood vessel wall 620 and/or tissue 630. Engaging the blood vessel wall and/or tissue, the closure element is further configured to return to the natural cross-section. Thereby, the engaged blood vessel wall and/or tissue are drawn substantially closed and/or sealed, such that, for example, hemostasis within the opening is enhanced.

Other aspects and features of the present invention will become apparent from consideration of the following description taken in conjunction with the accompanying drawings.

BRIEF DESCRIPTION OF THE DRAWINGS

FIG. 4A illustrates a cross-sectional side view of one embodiment of a triggering system for the carrier assembly of FIG. 3A.

FIG. 4B illustrates a first detailed cross-sectional side view of the triggering system of FIG. 4A.

FIG. 5A illustrates the carrier control system of FIGS. 4A-D as the carrier assembly of FIG. 3A moves distally from an initial predetermined position.

FIG. 5B illustrates the carrier control system of FIGS. 4A-D as the carrier assembly of FIG. 3A reaches a first predetermined position.

FIG. 6A illustrates a top view of one embodiment of a closure element in a natural, planar configuration and with a natural cross-section for use with the apparatus of FIG. 1.

FIG. 6B illustrates a side view of the closure element of FIG. 6A.

FIG. 6C illustrates a top view of the closure element of FIGS. 6A-B after a natural cross-section of the closure element has been reduced.

FIG. 6D illustrates a side view of the reduced closure element of FIG. 6C.

FIG. 6E illustrates a side view of the reduced closure element of FIGS. 6C-D as the reduced closure element transitions from the natural, planar configuration to a tubular configuration.

FIG. 6F illustrates a top view of the closure element of FIGS. 6C-D upon completing the transition from the natural, planar configuration to a substantially tubular configuration.

FIG. 6G illustrates a side view of the closure element of FIG. 6F.

FIG. 7C illustrates the closure element of FIGS. 6A-G as the cover member of FIG. 3D receives the carrier member of FIG. 3B.

FIG. 7D illustrates the closure element of FIGS. 6A-G being retained substantially within the carrier assembly of FIG. 3A when the carrier member of FIG. 3B is disposed substantially within the cover member of FIG. 3D.

FIG. 8C illustrates a locator assembly of the apparatus of FIG. 8B being advanced distally into the blood vessel.

FIG. 11A illustrates the assembled carrier assembly and triggering assembly of the alternative embodiment of the apparatus shown in FIG. 10A.

FIG. 11B illustrates a close-up view of the proximal end of the apparatus shown in FIG. 11A.

Figure 1:
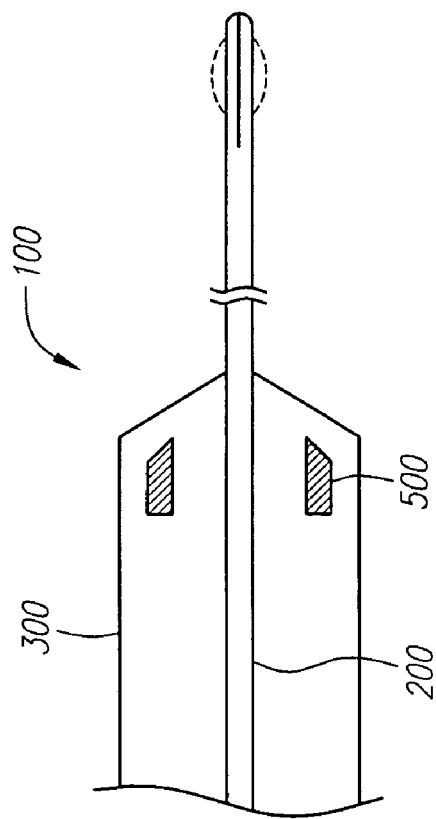
FIG. 1 provides a general illustration of an apparatus for closing openings formed in blood vessel walls in accordance with the present invention.

It should be noted that the figures are not drawn to scale and that elements of similar structures or functions are generally represented by like reference numerals for illustrative purposes throughout the figures. It also should be noted that the figures are only intended to facilitate the description of the preferred embodiments of the present invention. The figures do not describe every aspect of the present invention and do not limit the scope of the invention.

DETAILED DESCRIPTION OF THE PREFERRED EMBODIMENTS

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved, according to one embodiment of the present invention, by employing an apparatus 100 as shown in FIG. 1.

As will be discussed in more detail below, the apparatus 100 can deliver a closure element 500 (shown in FIGS. 6A-B)

through tissue 630 (shown in FIG. 8A) and into an opening 610 (shown in FIG. 8A) formed in and/or adjacent to a wall 620 (shown in FIG. 8A) of a blood vessel 600 (shown in FIG. 8A) or other body lumen. The closure element (or clip) 500 preferably has a generally annular-shape body 510 (shown in FIGS. 6A-B) defining a channel 540 and one or more barbs and/or tines 520 (shown in FIGS. 6A-B) for receiving and engaging the blood vessel wall 620 and/or the tissue 630 around the opening 610. Although the closure element 500 has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 6A-B. The natural cross-section 530 of the closure element 500 can be reduced to form a reduced closure element 500' that has a natural, planar configuration with opposing tines 520 and a reduced cross-section 530' as shown in FIGS. 6C-D. By rotating the opposing tines 520 axially as shown in FIG. 6E, the reduced closure element 500' can be further deformed to form a substantially tubular closure element 500" (shown in FIG. 6F) having the reduced cross-section 530' as well as being in a substantially tubular configuration with the tines 520 in an axial configuration.

Being configured to draw the blood vessel wall 620 and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof. As desired, the closure element 500 can include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. No. 6,197,042, in co-pending applications Ser. Nos. 09/546,998, 09/610,238, and 10/081,726. The disclosures of these references and any others cited therein are expressly incorporated herein by reference.

The apparatus 100 is configured to receive and retain the closure element 500 such that the closure element 500 is disposed substantially within the apparatus 100. Thereby, if the apparatus 100 is introduced via an introducer sheath 640 (shown in FIG. 8A), for example, the closure element 500 can be disposed within, and delivered by way of, a lumen 644 (shown in FIG. 8A) of the introducer sheath 640. The apparatus 100 also is configured to engage the blood vessel wall 620 adjacent to the opening 610. Being disposed substantially within the apparatus 100, the closure element 500 can deeply penetrate, without inadvertently contacting, tissue 630 adjacent to the opening 610 such that the apparatus 100 can position the closure element 500 substantially adjacent to an outer surface 620a (shown in FIG. 8A) of the blood vessel wall 620 adjacent to the opening 610.

When properly positioned, the apparatus 100 can be activated to distally deploy the closure element 500. Although preferably configured to substantially uniformly expand the closure element 500 beyond the natural cross-section 530 of the closure element 500 during deployment, the apparatus 100, as desired, can deploy the closure element 500 without expanding the closure element 500. The closure element 500, when deployed, is configured to engage significant amount of the blood vessel wall 620 and/or tissue 630 adjacent to the opening 610. Engaging the blood vessel wall 620 and/or tissue 630, the closure element 500 is further configured to return to the natural cross-section 530. Thus, the engaged blood vessel wall 620 and/or tissue 630 are drawn substantially closed and/or sealed, such that, for example, hemostasis within the opening 610 is enhanced.

The apparatus 100 can be provided as via one or more integrated components and/or discrete components. As shown in FIG. 1, for example, the apparatus 100 can comprise a locator (or obturator) assembly 200 and a carrier assembly 300. For purposes of illustration, the locator assembly 200 and the carrier assembly 300 are shown in FIG. 1 as comprising substantially separate assemblies. As desired, however, the locator assembly 200 and the carrier assembly 300 each can be provided, in whole or in part, as one or more integrated assemblies.

Figure 2A:
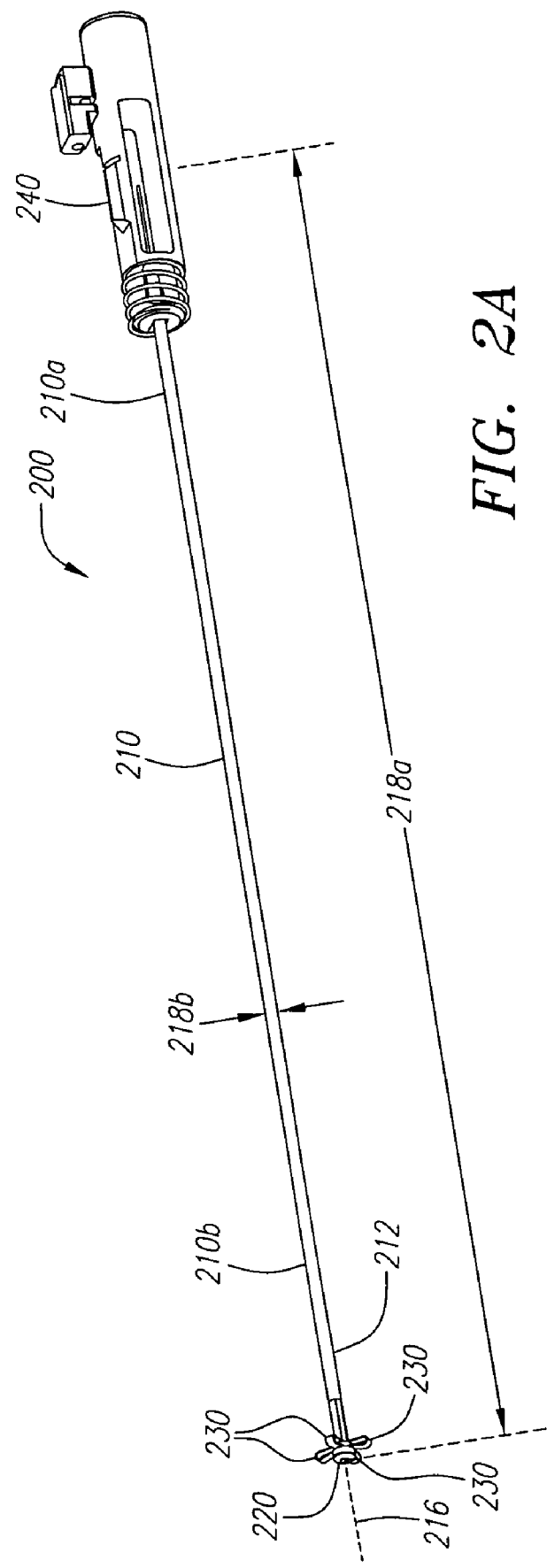
FIG. 2A illustrates one embodiment of a locator assembly for the apparatus of FIG. 1.

Being configured to extend into the opening 610, the locator assembly 200 can selectably engage the inner surface 620b of the blood vessel wall 620 adjacent to the opening 610. Thereby, the locator assembly 200 is configured to draw the blood vessel wall 620 taut and can maintain the proper position of the apparatus 100 as the blood vessel 600 pulsates. The locator assembly 200 can be provided in the manner disclosed in co-pending applications Ser. Nos. 09/732,835 and 10/081,723, the disclosure of which is expressly incorporated herein by reference, and preferably includes a flexible or semi-rigid tubular body 210, such as an elongate rail, with a longitudinal axis 216. As illustrated in FIG. 2A, the tubular body 210 has a proximal end region 210a and a distal end region 210b and includes a predetermined length 218a and a predetermined outer cross-section 218b, both of which can be of any suitable dimension. The distal end region 210b of the locator assembly 200 preferably includes a substantially rounded, soft, and/or flexible distal end or tip 220 to facilitate atraumatic advancement and/or retraction of the distal end region 210b into the blood vessel 600. As desired, a pigtail (not shown) may be provided on the distal end 220 to further aid atraumatic advancement of the distal end region 210b.

The distal end region 210b of the locator assembly 200 further is selectably controllable between an unexpanded state and an expanded state. In the unexpanded state, the distal end region 210b has an unexpanded size; whereas, the distal end region 210b in the expanded state has an expanded size, which is greater than the unexpanded size of the distal end region 210b in the unexpanded state. The distal end region 210b is configured to expand from the unexpanded size to the expanded size and/or to contract from the expanded size to the unexpanded size, and the expansion and contraction of the distal end region 210b preferably is substantially uniform about the longitudinal axis 216. For example, one or more expansion elements 230 can be provided on the distal end region 210b and can be configured to expand substantially transversely with respect to a longitudinal axis 216 of the locator assembly 200. Preferably being substantially equally distributed about an outer periphery 212 of the distal end region 210b, the expansion elements 230 may include radiopaque markers (not shown) or may be wholly or partially formed from a radiopaque material to facilitate observation of the expansion elements 230 and/or the distal end region 210b using fluoroscopy or other imaging systems.

Figure 2B:
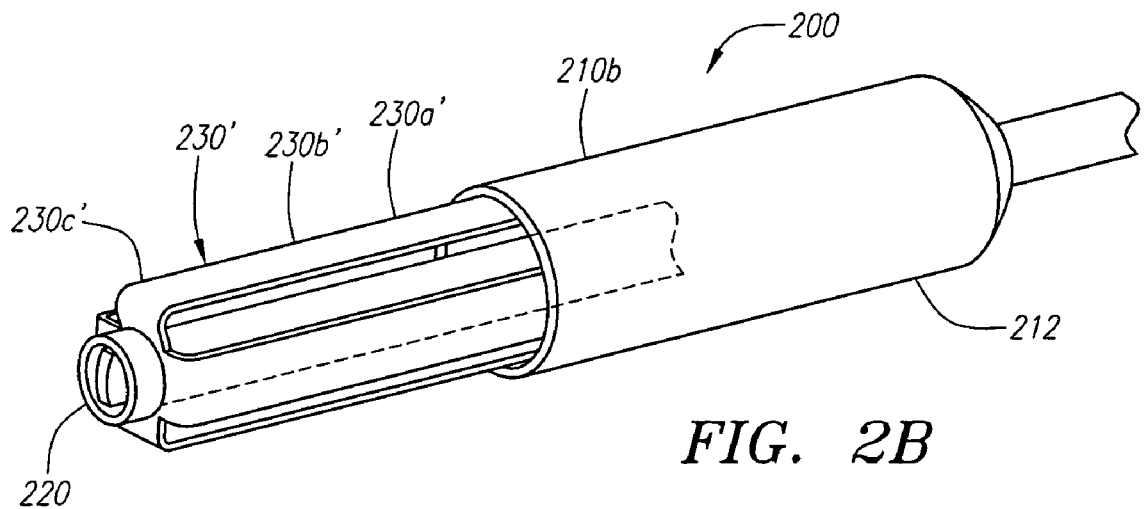
FIG. 2B illustrates one embodiment of a distal end region of the locator assembly of FIG. 2A when the distal end region is in an unexpanded state.
Figure 2C:
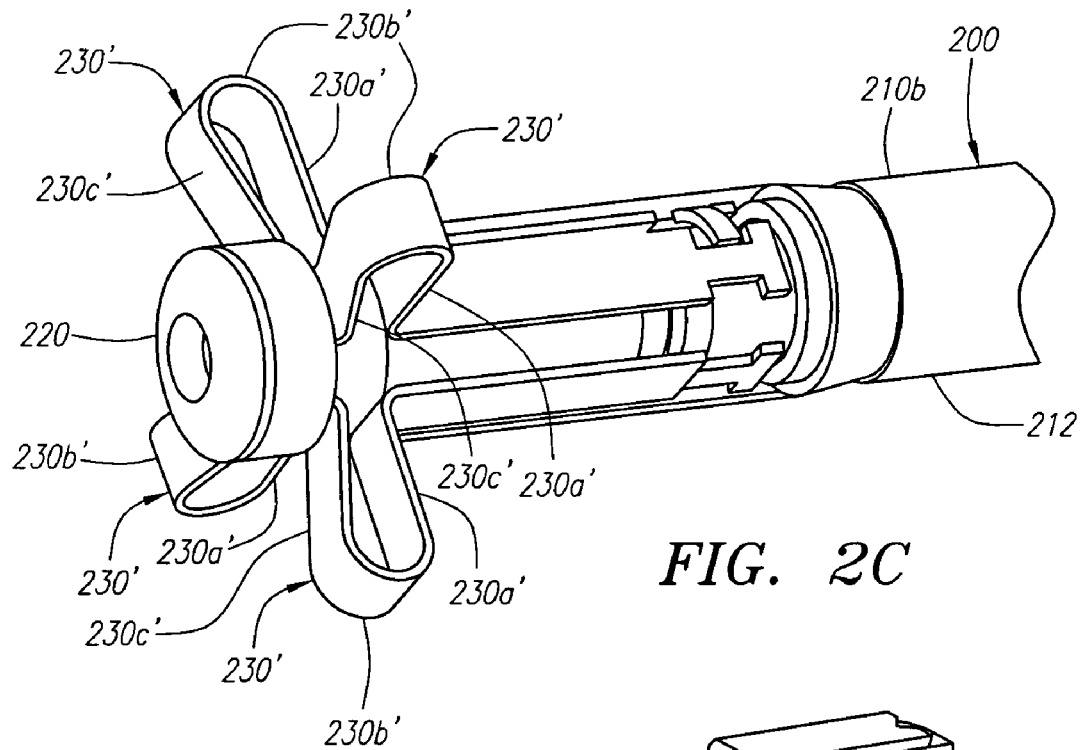
FIG. 2C illustrates the distal end region of the locator assembly of FIG. 2B when the distal end region is in an expanded state.

At least one, and preferably all, of the expansion elements 230 can comprise a substantially flexible member 230' with a substantially fixed end region 230a', an intermediate region 230b', and a movable end region 230c' as shown in FIGS. 2B-C. For each substantially flexible member 230', the fixed end region 230a' is fixedly coupled with the distal end region 210b; whereas, the movable end region 230c' is movably coupled with the distal end region 210b and configured to be axially movable relative to the fixed end region 230a'. When each movable end region 230c' is axially moved toward the relevant fixed end region 230a', the intermediate regions 230b' buckle and/or expand transversely outwardly, thereby transitioning the distal end region 210b of the locator assembly 200 from the unexpanded state to the expanded state. In contrast, the distal end region 210b transitions from the expanded state to the unexpanded state as each of the movable end regions 230c' are axially moved away from the relevant fixed end region 230a'. Although the expansion elements 230 are shown as comprising the flexible members 230' in FIGS. 2B-C for purposes of illustration, it is understood that the expansion elements 230 can comprise any type of expansion elements and are not limited to the illustrated embodiments.

Figure 2D:
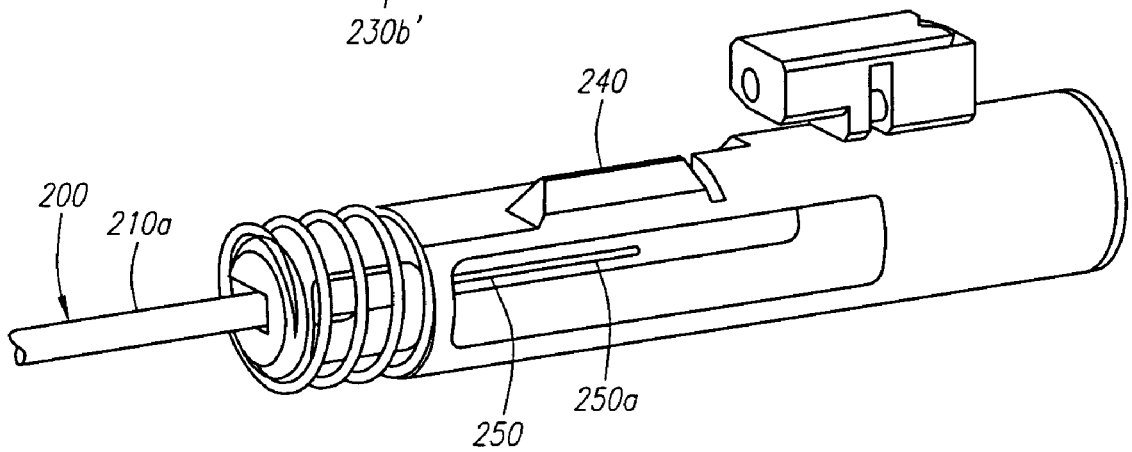
FIG. 2D illustrates one embodiment of a proximal end region of the locator assembly of FIG. 2A.

Turning to FIG. 2D, the locator assembly 200 also can include a locator control system 240 that is coupled with the proximal end region 210a of the locator assembly 200 and that is configured to selectively control the distal end region 210b of the locator assembly 200 between the unexpanded and expanded states. The locator control system 240 can selectively control the distal end region 210b between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210a and the distal end region 210b. The control member 250 has a proximal end region 250a that is coupled with the locator control system 240, preferably via a control block 260 (shown in FIG. 4D), and a distal end region (not shown) that is coupled with the distal end region 210b of the locator assembly 200, the expansion elements 230, and/or the movable end regions 230c' of the substantially flexible members 230'. The locator control system 240 can selectively transition the distal end region 210b, the expansion elements 230, and/or the substantially flexible members 230' between the unexpanded and expanded states by moving the control member 250 axially relative to the tubular body 210.

The locator control system 240 preferably includes a locator release system 490 for maintaining the unexpanded state and/or the expanded state of the distal end region 210b, the expansion elements 230, and/or the substantially flexible members 230'. Preferably being configured to maintain the expanded state of the distal end region 210b, the locator release system 490 can comprise any type of locking system and can be engaged, for instance, by activating the switching system. For example, once the substantially flexible members 230' have entered the expanded state, the locator release system 490 can secure the control member 250 to prevent axial movement relative to the tubular body 210, thereby maintaining the substantially flexible members 230' in the expanded state.

In the manner described in more detail below, the locator control system 240 also can be configured to disengage the locator release system 490, such that the distal end region 210b, the expansion elements 230, and/or the substantially flexible members 230' can transition between the unexpanded and expanded states. The locator release system 490 can be disengaged, for example, by activating an emergency release system (not shown). As desired, the locator control system 240 can further include a biasing system (not shown), such as one or more springs, to bias the distal end region 210b, the expansion elements 230, and/or the substantially flexible members 230' to enter and/or maintain the unexpanded state when the locator release system 490 is disengaged.

Returning to FIG. 1, the carrier assembly 300 is coupled with, and slidable relative to, the locator assembly 200. The carrier assembly 300 is configured to receive and retain the closure element 500 (shown in FIGS. 6A-B), which preferably is disposed substantially within the carrier assembly 300. When the locator assembly 200 engages the inner surface 620b (shown in FIG. 8A) of the blood vessel wall 620 (shown in FIG. 8A), the carrier assembly 300 is further configured to position the closure element 500 substantially adjacent to the opening 610 (shown in FIG. 8A) and to deploy the closure element 500. Upon being deployed, the closure element 500 can maintain the reduced cross-section 530' (shown in FIGS. 6C-D) but preferably can temporarily and substantially uniformly expand beyond the natural cross-section 530 (shown in FIGS. 6A-B) of the closure element 500. In either case, the closure element 500, when deployed, can engage significant amount of the blood vessel wall 620 and/or tissue 630 adjacent to the opening 610. Thereafter, the closure element 500 is configured to return to the natural cross-section 530, preferably substantially uniformly, such that the blood vessel wall 620 and/or tissue 630 is drawn substantially closed and/or sealed.

Figure 3A:
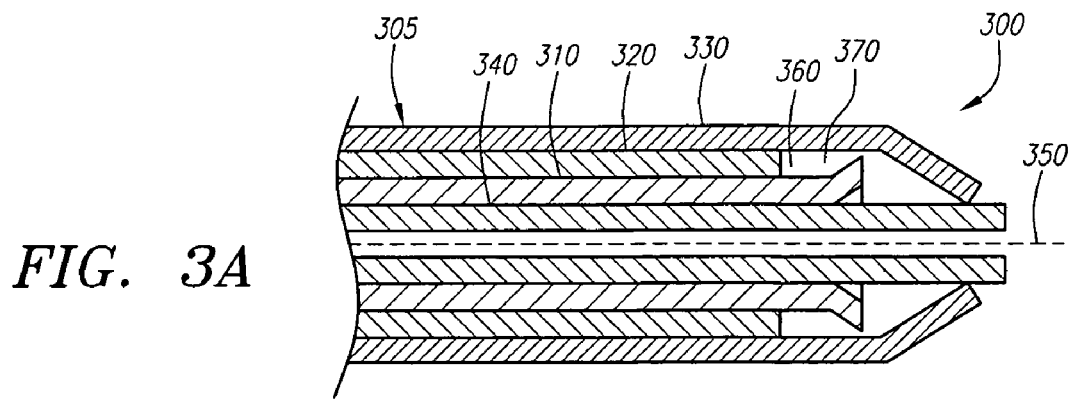
FIG. 3A illustrates one embodiment of a carrier assembly for the apparatus of FIG. 1.

Turning to FIGS. 3A-D, the carrier assembly 300 can include a tube set 305, comprising a carrier member 310, a pusher member 320, and a cover member 330. The carrier member 310, the pusher member 320, and the cover member 330 can be provided as a plurality of nested, telescoping members with a common longitudinal axis 350 as illustrated in FIG. 3A. The carrier member 310 is configured to receive and support the closure element 500. While being disposed on the carrier member 310, the closure element 500 preferably is deformed from the natural, planar configuration to form the substantially tubular closure element 500" (shown in FIGS. 6F-G) as will be discussed in more detail below. Being disposed substantially about, and supported by, an outer periphery 312b of the carrier member 310, the substantially tubular closure element 500" can be substantially in axial alignment with the carrier member 310 with the tines 520 pointed substantially distally.

Figure 3B:
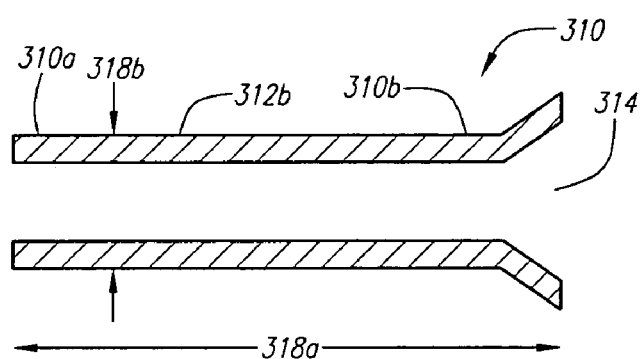
FIG. 3B illustrates one embodiment of a carrier member for the carrier assembly of FIG. 3A.

Preferably being formed as a substantially rigid, semi-rigid, or flexible tubular member, the carrier member 310 has a proximal end region 310a and a distal end region 310b and includes a predetermined length 318a and a predetermined cross-section 318b, both of which can be of any suitable dimension. The carrier member 310 also can define a lumen 314 that extends substantially between the proximal end region 310a and the distal end region 310b and that is configured to slidably receive at least a portion of the tubular body 210 of the locator assembly 200. Although the cross-section 318b of the carrier member 310 generally is substantially uniform, the distal end region 310b of the carrier member 310 preferably has a cross-section that increases distally, as illustrated in FIGS. 3A-B, for substantially uniformly expanding the substantially tubular closure element 500" beyond the natural cross-section 530 of the closure element 500 when the substantially tubular closure element 500" is deployed. To deploy the closure element 500 without expanding the closure element 500, the distal end region 310b can be formed with a cross-section (not shown) that is substantially uniform. Although shown and described as having the cross-section that increases distally for expanding the substantially tubular closure element 500", it will be understood that the distal end region 310b of the carrier member 310 can be provided with the-substantially-uniform cross-section and that the substantially tubular closure element 500" can be deployed without being expanded.

Being configured to distally deploy the substantially tubular closure element 500", the pusher member 320 has a proximal end region 320a and a distal end region 320b and is coupled with, and slidable relative to, the carrier member 310. The pusher member 320 includes a predetermined length 328a and a predetermined cross-section 328b, both of which can be of any suitable dimension and can be configured to slidably receive the carrier member 310 such that the distal end region 320b of the pusher member 320 is offset proximally from the distal end region 310b of the carrier member 310. As desired, the predetermined length 328a of the pusher member 320 can be greater than or substantially equal to the predetermined length 318a of the carrier member 310. The predetermined length 328a of the pusher member 320 however preferably is less than the predetermined length 318a of the carrier member 310 such that the carrier member 310 and the pusher member 320 at least partially define a space 360 distal to the distal end region 320b of the pusher member 320 and along the periphery 312b of the carrier member 310.

Figure 3C:
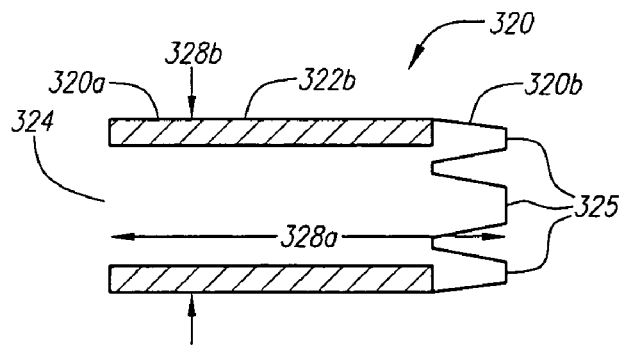
FIG. 3C illustrates one embodiment of a pusher member for the carrier assembly of FIG. 3A.

Being formed from a substantially rigid, semi-rigid, or flexible material, the pusher member 320 preferably is substantially tubular and can define a lumen 324 that extends substantially between the proximal end region 320a and the distal end region 320b and that is configured to slidably receive at least a portion of the carrier member 310. The cross-section 328b of the pusher member 320 preferably is substantially uniform, and the distal end region 320b of the pusher member 320 can comprise one or more longitudinal extensions 325, which extend distally from the pusher member 320 and along the periphery 312b of the carrier member 310 as shown in FIG. 3C. The longitudinal extensions 325 preferably are biased such that the longitudinal extensions 325 extend generally in parallel with common longitudinal axis 350. The longitudinal extensions 325 are sufficiently flexible to expand radially, and yet sufficiently rigid to inhibit buckling, as the distal end region 320b is directed distally along the carrier member 310 and engage the distally-increasing cross-section of the distal end region 310b of the carrier member 310 to deploy the substantially tubular closure element 500".

The cover member 330 is configured to retain the substantially tubular closure element 500" substantially within the carrier assembly 300 prior to deployment. Being coupled with, and slidable relative to, the pusher member 320, the cover member 330 has a proximal end region 330a and a distal end region 330b and includes a predetermined length 338a and a predetermined cross-section 338b, both of which can be of any suitable dimension. Preferably being formed as a substantially rigid, semi-rigid, or flexible tubular member, the cover member 330 has an inner periphery 332a and an outer periphery 332b and can define a lumen 334. The lumen 334 extends substantially between the proximal and distal end regions 330a, 330b of the cover member 330 and can be configured to slidably receive at least a portion of the pusher member 320. When the cover member 330 is properly positioned within the carrier assembly 300, the distal end region 330b is configured to extend over the space 360, thereby defining an annular cavity 370 for receiving and retaining the substantially tubular closure element 500".

Figure 3D:
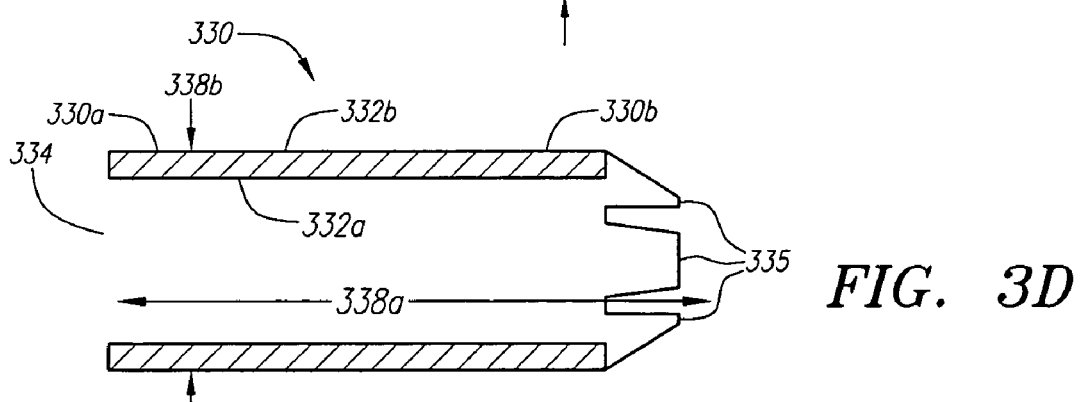
FIG. 3D illustrates one embodiment of a cover member for the carrier assembly of FIG. 3A.

The cross-section 338b of the cover member 330 preferably is substantially uniform, and the distal end region 330b of the cover member 330 preferably comprises one or more longitudinal extensions 335, which extend distally from the cover member 330 and along an outer periphery 322b of the pusher member 320 as shown in FIG. 3D. Although the longitudinal extensions 335 can extend generally in parallel with common longitudinal axis 350, the longitudinal extensions 335 preferably are biased such that the plurality of longitudinal extensions 335 extend substantially radially inwardly as illustrated in FIGS. 3A and 3D. Thereby, the longitudinal extensions 335 can at least partially close the lumen 334 substantially adjacent to the distal end region 330b of the cover member 330. To permit the substantially tubular closure element 500" to be deployed from the annular cavity 370, the longitudinal extensions 335 preferably are sufficiently flexible to expand radially to permit the distal end region 310b of the carrier member 310 to move distally past the cover member 330 to open the annular cavity 370 such that the distal end region 330b no longer extends over the space 360.

If the carrier assembly 300 is assembled as the plurality of nested, telescoping members as shown in FIG. 3A, the carrier member 310 is at least partially disposed within, and slidable relative to, the lumen 324 of the pusher member 320. The pusher member 320, in turn, is at least partially disposed within, and slidable relative to, the lumen 334 of the cover member 330. To couple the carrier assembly 300 with the locator assembly 200, the tubular body 210 of the locator assembly 200 is at least partially disposed within, and slidable relative to, the lumen 314 of the carrier member 310. The longitudinal axis 216 of the locator assembly 200 preferably is substantially in axial alignment with the common longitudinal axis 350 of the carrier member 310, the pusher member 320, and the cover member 330.

Figure 3E:
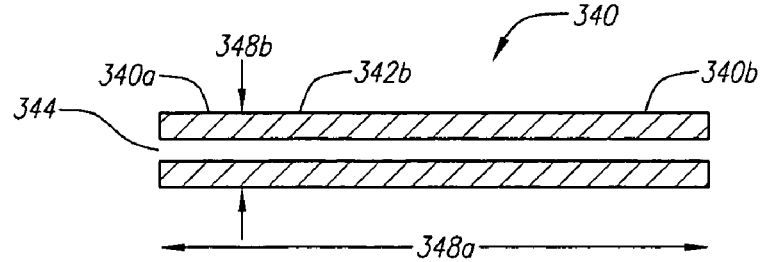
FIG. 3E illustrates one embodiment of a support member for the carrier assembly of FIG. 3A.

It will be appreciated that the tube set 305 preferably also includes a support member 340 as shown in FIGS. 3A and 3E. The support member 340 is configured to slidably receive the tubular body 210 of the locator assembly 200 and to provide radial support for the distal end region 210b of the tubular body 210 when the locator assembly 200 is coupled with the carrier assembly 300. The carrier assembly 300 can advantageously include the support member 340, for example, if the tubular body 210 is not sufficiently rigid or under other circumstances in which support for the tubular body 210 might be desirable. It also will be appreciated that the support member 340 also can be configured to inhibit the plurality of longitudinal extensions 335, which extend from the distal end region 330b of the cover member 330, from expanding prematurely when the closure element 500 is deployed.

Preferably being formed as a substantially rigid, semi-rigid, or flexible tubular member, the support member 340 includes a proximal end region 340a and a distal end region 340b. Having an outer periphery 342b, the support member 340 can define a lumen 344 that extends substantially between the proximal end region 340a and the distal end region 340b and that is configured to slidably receive and support at least a portion of the tubular body 210 of the locator assembly 200. The support member 340, in turn, can be at least partially slidably disposed within the lumen 314 of the carrier member 310 such that the tubular body 210 of the locator assembly 200 is coupled with, and slidable relative to, the carrier member 310 in the manner described in more detail above. The support member 340 has a predetermined length 348a and a predetermined cross-section 348b, both of which can be of any suitable dimension, and the cross-section 348b preferably is substantially uniform. Although shown and described as being substantially separate for purposes of illustration, it will be appreciated that the carrier member 310, the pusher member 320, the cover member,330, and/or the support member 340 can be provided, in whole or in part, as one or more integrated assemblies.

The carrier assembly 300 also can include a housing 380 as illustrated in FIG. 4A. Preferably being formed as an elongate member with a longitudinal axis 386, the housing 380 has an outer periphery 382b and includes a proximal end region 380a and a distal end region 380b. Thereby, when the apparatus 100 is properly assembled, the tubular body 210 of the locator assembly 200 at least partially disposed within, and slidable relative to, the tube set 305 such that the distal end region 210b of the tubular body 210 extends beyond the distal end regions 310b, 320b, 330b, and/or 340b. The tubular body 210, the carrier member 310, the pusher member 320, the cover member 330, and, if provided, the support member 340 are at least partially disposed within, and slidable relative to, the housing 380, and the respective distal end regions 210b, 310b, 320b, 330b, and 340b extend from the distal end region 380b of the housing 380 such that the common longitudinal axis 350 (shown in FIG. 3A) of the tube set 305 is substantially axially aligned with the longitudinal axis 386 of the housing 380. Being configured to slidably retain the respective proximal end regions 210a, 310a, 320a, 330a, and 340a, the housing 380 supports the tube set 305 and can have one or more handles 390 to facilitate use of the apparatus 100. The handles 390 extend substantially radially from the outer periphery 382b of the housing 380 and can be provided in the manner known in the art.

When the apparatus 100 is properly assembled, the tubular body 210 of the locator assembly 200 is at least partially disposed within, and slidable relative to, the tube set 305 of the carrier assembly 300 such that the distal end region 210b of the tubular body 210 extends beyond the distal end regions 310b, 320b, 330b, and/or 340b. Further, the proximal end region 210a of the tubular body 210 and the proximal end regions 310a, 320a, 330a, and/or 340a of the tube set 305 are at least partially disposed within, and slidable relative to, the housing 380. The switching system of the locator assembly 200 and a switching system 450 of the triggering system 400 preferably are accessible external to the housing 380 as shown in FIG. 4A.

Figure 4C:
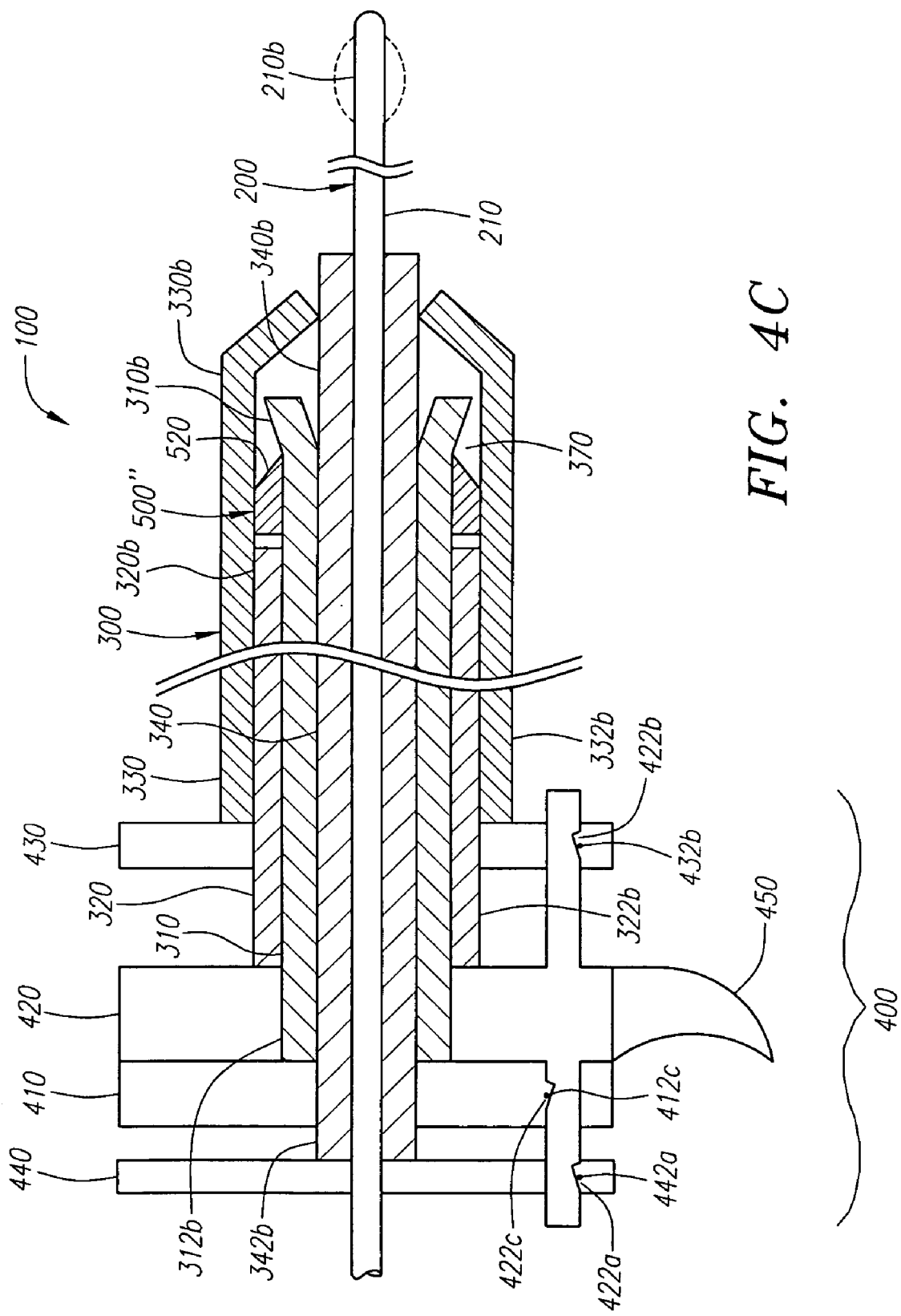
FIG. 4C illustrates a detailed view of the triggering system of FIG. 4B.
Figure 4D:
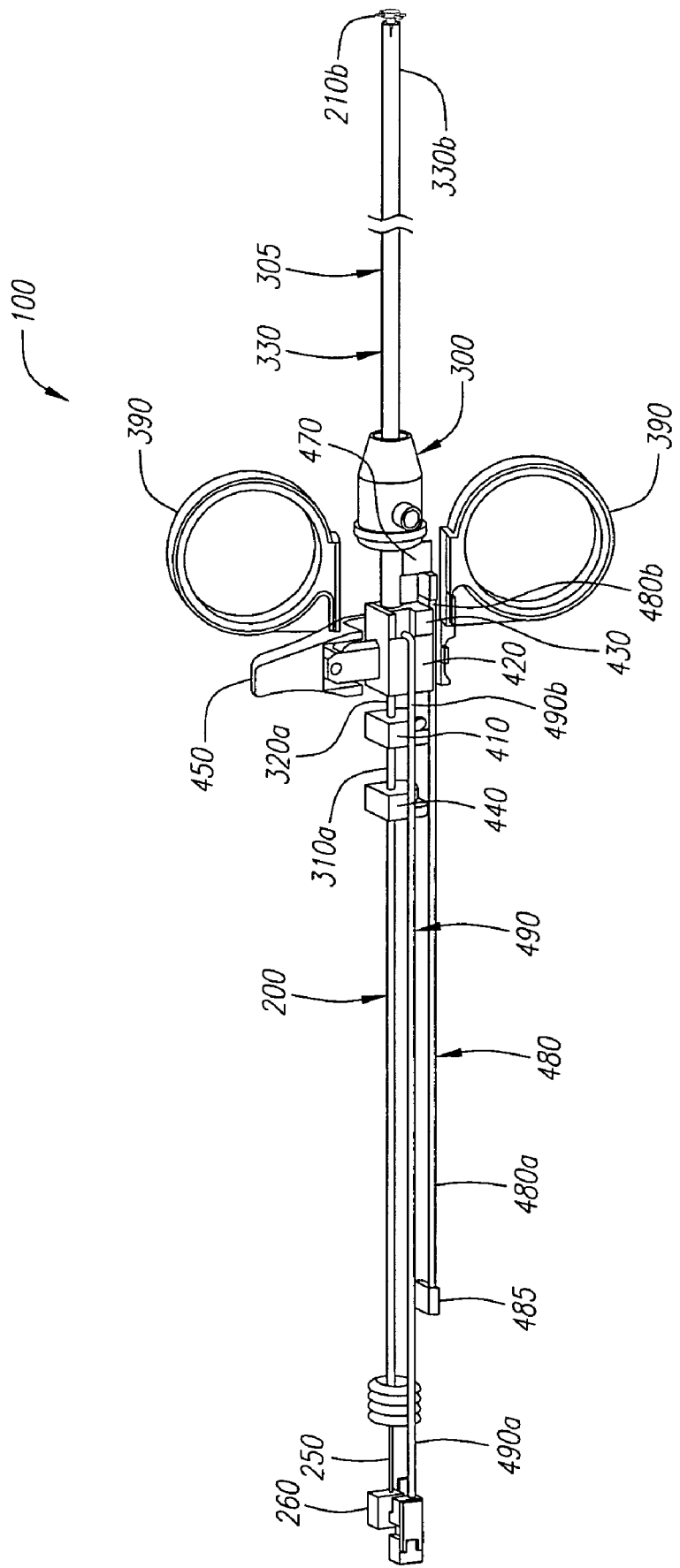
FIG. 4D illustrates a second detailed cross-sectional side view of the triggering system of FIG. 4A.

Turning to FIGS. 4B-D, a triggering system 400 can be disposed substantially within the housing 380. The triggering system 400 is configured to control the relative axial movement and/or positioning of the respective distal end regions 310b, 320b, 330b, and 340b of the tube set 305 and/or the distal end region 210b of the locator assembly 200. Being coupled with the proximal end regions 210a, 310a, 320a, 330a, and/or 340a, the triggering system 400 can control the relative axial movement of the distal end regions 210b, 310b, 320b, 330b, and/or 340b in any manner, such as by being activated by the switching system 450. As desired, the triggering system 400 can induce axial motion, such as distal motion, with respect to one or more of the distal end regions 210b, 310b, 320b, 330b, and/or 340b. One or more of the distal end regions 210b, 310b, 320b, 330b, and/or 340b can be axially moved. Axial motion of one or more of the carrier member 310, the pusher member 320, the cover member 330, and the support member 340 and/or the tubular body 210 can be attained, for example, by applying an axial force to the switching system 450. To facilitate monitoring of the positioning of the carrier assembly 300 and/or the substantially tubular closure element 500", one or more of the distal end regions 210b, 310b, 320b, 330b, and/or 340b may include radiopaque markers (not shown) or may be wholly or partially formed from a radiopaque material.

The triggering system 400 is configured to overcome internal resistance such that the relative axial movement and/or positioning of the respective distal end regions 310b, 320b, 330b, and 340b of the tube set 305 and/or the distal end region 210b of the locator assembly 200 are controlled in accordance with a predetermined manner when the triggering system 400 is activated. Thereby, movement and/or positioning of the distal end regions 310b, 320b, 330b, 340b, and/or 210b is initiated when at least a predetermined quantity of force is applied to the switching system 450. Stated somewhat differently, a force that is less than the predetermined quantity generally is insufficient to activate the triggering system 400; whereas, when the force increases to a level that is greater than or substantially equal to the predetermined quantity, the triggering system 400 is configured to activate, moving and/or positioning the distal end regions 310b, 320b, 330b, 340b, and/or 210b in accordance with the predetermined manner. The triggering system 400, once activated, preferably continues to move and/or position the distal end regions 310b, 320b, 330b, 340b, and/or 210b in accordance with the predetermined manner until the closure element 500 is deployed.

The triggering system 400, for example, can comprise one or more sets of cooperating detents for coupling the axial motion of the distal end regions 310b, 320b, 330b, and 340b in accordance with a predetermined manner when the triggering system 400 is activated. The term "detents" refers to any combination of mating elements, such as blocks, tabs, pockets, slots, ramps, locking pins, cantilevered members, support pins, and the like, that may be selectively or automatically engaged and/or disengaged to couple or decouple the carrier member 310, the pusher member 320, the cover member 330, and the support member 340 relative to one another. It will be appreciated that the cooperating detents as illustrated and described below are merely exemplary and not exhaustive. For example, the cooperating detents can include a first set of cooperating blocks and pockets for releasable coupling the support member 340, the carrier member 310, the pusher member 320, and the cover member 330. When the carrier assembly 300 reaches a first predetermined distal position, the support member 340 can be decoupled from the carrier member 310, the pusher member 320, and the cover member 330 and preferably is substantially inhibited from further axial movement. Thereby, the carrier member 310, the pusher member 320, and the cover member 330 may continue to be directed distally as the support member 340 remains substantially stationary.

As shown in FIGS. 4B-C, the cooperating detents can comprise a carrier block 410, a pusher block 420, a cover block 430, and a support block 440, which can be configured to couple and decouple in accordance with the predetermined manner. For example, the carrier block 410 is disposed on the proximal end region 310a of the carrier member 310 and includes a carrier pin 412c that extends from the carrier block 410; whereas, the proximal end region 330a of the cover member 330 and the proximal end region 340a the support member 340 are respectively coupled with the cover block 430 and the support block 440. A cover pin 432b extends from the cover block 430, and the support block 440 has a support pin 442a, which extends from the support block 440. The support pin 442a, the cover pin 432b, and the carrier pin 412c each preferably are formed from a substantially rigid material, such as an alloy of nickel-titanium.

The pusher block 420 is disposed on the proximal end region 320a of the pusher member 320 and forms a support slot 422a, a cover slot 422b, and a carrier slot 422b. The support slot 422a is configured to receive and releasable engage the support pin 442a by which the support member 340 can be coupled with, and decoupled from, the pusher member 320. The cover member 330 can be coupled with, and decoupled from, the pusher member 320 via the cover slot 422b, which is configured to receive and releasable engage the cover pin 432b. The carrier slot 422c is configured to receive and releasable engage the carrier pin 412c such that the carrier member 310 can be coupled with, and decoupled from, the pusher member 320. The carrier block 410, the pusher block 420, the cover block 430, and the support block 440 preferably are respectively disposed substantially on the outer peripheries 312b, 322b, 332b, and 342b and can be configured to couple and decouple in accordance with the predetermined manner.

The triggering system 400 also includes one or more stops for engaging the pusher block 420, the cover block 430, and/or the support block 440, respectively. As illustrated in FIG. 4B, a support stop 460a, a cover stop 460b, and a carrier stop 460c each are formed in the housing 380 and are configured to receive, and substantially inhibit further movement of, the support block 440, the cover block 430, and the carrier block 410, respectively, in accordance with the predetermined manner. For example, when an axial force is applied to the tube set 305 via the switching system 450, the cover block 430 moves distally within the housing 380, and the cover block 430 approaches the cover stop 460b. Upon being received by the cover stop 460b, the cover block 430 is substantially locked in place, substantially preventing any further motion by the cover block 430.

Resisting the axial force, the cover pin 412b provides a static load while the axial force is less than the predetermined quantity of force. As the axial force increases to a level that is greater than or substantially equal to the predetermined quantity, the cover pin 412b can be displaced from the cover slot 422b, decoupling the cover member 330 from the carrier member 310, the pusher member 320, and the support member 340. Creating the internal resistance to be overcome by the triggering system 400, the static forces provided by the pins 412a, 412b, and 412c is approximately proportional to a composition and cross-section of the respective pins 412a, 412b, and 412c and/or a depth and a slope of the respective slots 422a, 422b, and 422c. As desired, the pins 412a, 412b, and 412c can be configured to provide static loads that are differing and/or substantially uniform.

Turning to FIG. 4D, the triggering system 400 can further have a tube release system 470 for inhibiting inadvertent advancement of the tube set 305. The tube release system 470 is coupled with a tube release member 480, such as a rod, wire, or other elongate member. The tube release member 480 has a proximal end region 480a that is disposed substantially between the pusher block 420 and the housing 380 (shown in FIG. 4A) and a distal end region 480b that is coupled with the tube release system 470. Preferably, a tab 485 is coupled with the proximal end region 480a of the tube release member 480, and a pin (not shown) extends from the pusher block 420 and is disposed substantially between the tab 485 and a groove (not shown) formed in the housing 380. The tube release system 470 is configured to release the tube set 305 when the tube release member 480 is moved proximally, freeing the pusher block 420.

A locator release system 490 for permitting the distal end region 210b, the expansion elements 230, and/or the substantially flexible members 230' of the locator assembly 200 to transition from the expanded state to the unexpanded state can be included with the triggering system 400. The locator release system 490 can comprise a rod, wire, or other elongate member and has a proximal end region 490a and a distal end region 490b. The proximal end region 490a of the locator release system 490 can be coupled with, and configured to activate, the locator control system 240 (shown in FIG. 2D), and the distal end region 490b extends beyond the pusher block 420. Thereby, when the pusher block 420 is advanced during deployment of the closure element 500, the control block 260 is disengaged such that the distal end region 210b, the expansion elements 230, and/or the substantially flexible members 230' of the locator assembly 200 to transition from the expanded state to the unexpanded state.

Figure 5C:
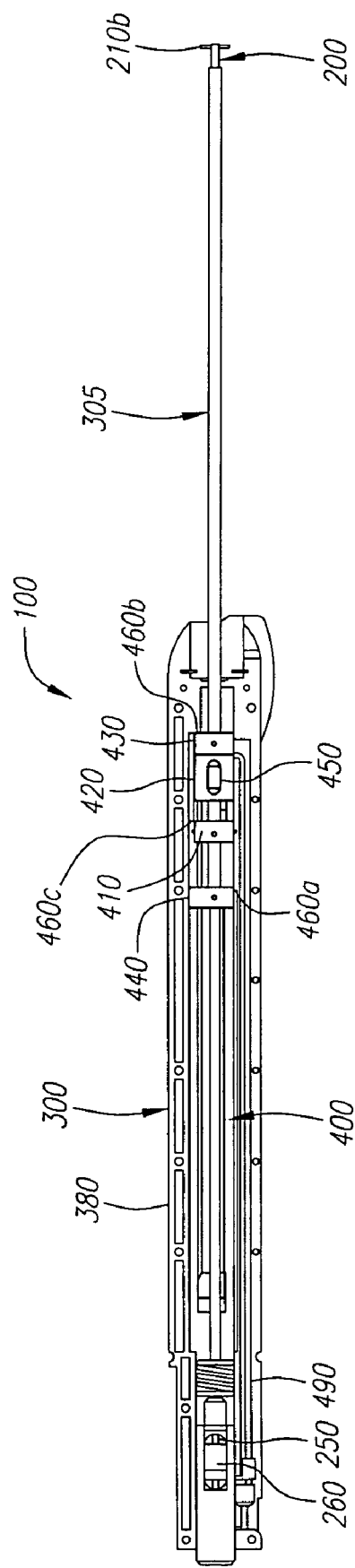
FIG. 5C illustrates the carrier control system of FIGS. 4A-D as the carrier assembly of FIG. 3A reaches a second predetermined position.

The operation of the triggering system 400 in accordance with one predetermined manner is illustrated in FIGS. 5A-C with the closure element 500 (shown in FIGS. 6A-B) disposed substantially within the apparatus 100. As shown in FIG. 5A, the distal end region 210b of the locator assembly 200 has been positioned as desired and has transitioned from the unexpanded state to the expanded state. While the locator control system 240 (shown in FIG. 2D) maintains the distal end region 210b in the expanded state, a distally-directed axial force is applied to the triggering system 400 via the switching system 450. Once the tube release member 480 (shown in FIG. 4D) has been moved proximally to free the pusher block 420, the tube set 305 is substantially freely slidable within the housing 380 and responds to the axial force by sliding distally from an initial predetermined position to a first predetermined position.

In the initial predetermined position, the carrier member 310, the pusher member 320, the cover member 330, and the support member 340 are coupled via the slots 422c, 422b, and 422a (shown in FIG. 4C) and the pins 412c, 422b, and 442a (shown in FIG. 4C). Stated somewhat differently, the support pin 442a, the cover pin 432b, and the carrier pin 412c are respectively disposed within, and engaged by, the support slot 422a, the cover slot 422b, and the carrier slot 422c such that the carrier block 410, the pusher block 420, the cover block 430, and the support block 440 are coupled as illustrated in FIG. 4C. Therefore, the carrier member 310, the pusher member 320, the cover member 330, and the support member 340 each slide distally from the initial predetermined position to the first predetermined position in response to the axial force.

FIG. 5B illustrates the positions of the carrier member 310, the pusher member 320, the cover member 330, and the support member 340 upon reaching the first predetermined position. In the first predetermined position, the support block 440 and the cover block 430 respectively engage the support stop 460a and the cover stop 460b. Thereby, the support stop 460a receives, and substantially inhibits further movement of, the support block 440 and, therefore, the support member 340; whereas, the cover stop 460b receives, and substantially inhibits further movement of, the cover block 430 and, therefore, the cover member 330. Although the support block 440 and the cover block 430 preferably engage the support stop 460a and the cover stop 460b in the first predetermined position, it will be appreciated that the support block 440 can engage the support stop 460a and the cover block 430 can engage the cover stop 460b in different predetermined positions. In other words, the predetermined manner can comprise any number of predetermined positions, each predetermined position being associated with any number of the blocks 410, 420, 430, and 440 engaging any number of relevant stops 460a, 460b, and 460c.

To continue distally from the first predetermined position, the carrier member 310 and the pusher member 320 can be decoupled from the cover member 330 and the support member 340 by disengaging the support pin 442a and the cover pin 432b from the support slot 422a and the cover slot 422b, respectively. In the manner described in more detail above with reference to FIGS. 4B-C, the support pin 442a and the cover pin 432b each resist the axial force. While the axial force is less than the combined static force provided by the support pin 442a and the cover pin 432b, the carrier member 310 and the pusher member 320 remain coupled with the cover member 330 and the support member 340. As the axial force increases to a level that is greater than or substantially equal to the combined static force, the support pin 442a and the cover pin 432b are respectively displaced from the support slot 422a and the cover slot 422b, decoupling the carrier member 310 and the pusher member 320 from the cover member 330 and the support member 340. Thereby, the cover member 330 and the support member 340 preferably are inhibited from further distal movement and remain substantially stationary; whereas, the carrier member 310 and the pusher member 320 proceed distally toward a second predetermined position. The pusher member 320 and the carrier member 310 continue distally until the second predetermined position is reached as shown in FIG. 5C. In the second predetermined position, the carrier block 410 engages the carrier stop 460c. Thereby, the carrier stop 460c receives, and substantially inhibits further movement of, the carrier block 410 and, therefore, the carrier member 310. To continue distally from the second predetermined position, the pusher member 320 can be decoupled from the carrier member 310 by disengaging the carrier pin 412c from the carrier slot 422b. In the manner described in more detail above with reference to FIGS. 4B-C, the carrier pin 412c resists the axial force. While the axial force is less than the static force provided by the carrier pin 412c, the pusher member 320 remains coupled with the carrier member 310.

As the axial force increases to a level that is greater than or substantially equal to the static force, the carrier pin 412c is displaced from the carrier slot 422c, decoupling the pusher member 320 from the carrier member 310. Thereby, the carrier member 310 preferably is inhibited from further distal movement and remains substantially stationary; whereas, the pusher member 320 proceed distally to deploy the closure element 500 and to activate the locator release system 490 (shown in FIG. 2D) such that the distal end region 210b, the expansion elements 230, and/or the substantially flexible members 230' of the locator assembly 200 transition from the expanded state to the unexpanded state. Preferably, the axial force that is applied to overcome the static force associated with the first predetermined position is sufficient to overcome the static forces associated with the subsequent predetermined positions, to deploy the closure element 500, and to activate the locator release system 490 such that the triggering system 400 operates in one substantially-continuous motion.

It will be appreciated that the triggering system 400 can include an energy storing element (not shown), which can be disposed substantially between the housing 380 and the blocks 410, 420, 430, and 440 and which is configured to store potential energy for moving the tube set 305 from the initial predetermined position through the other predetermined positions, deploying the closure element 500, and/or activating the locator release system 490. The energy storing element is configured store the potential energy when the tube set 305 is in the initial predetermined position and to release the potential energy, when activated, such that the tube set 305 travels through the predetermined positions at a substantially constant and continuous rate. For example, the energy storing element can comprise one or more springs (not shown). Each of the springs can be in a compressed state when the tube set 305 is in the initial predetermined position and released from the compressed state when the switching system 450 of the triggering system 400 is activated.

Figure 7A:
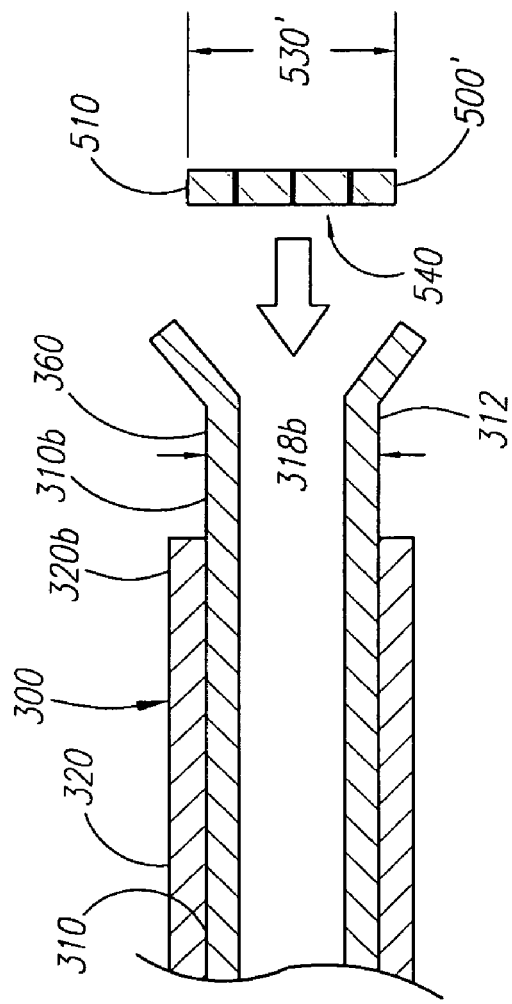
FIG. 7A illustrates the closure element of FIGS. 6A-G prior to being disposed upon the carrier member of FIG. 3B.
Figure 7B:
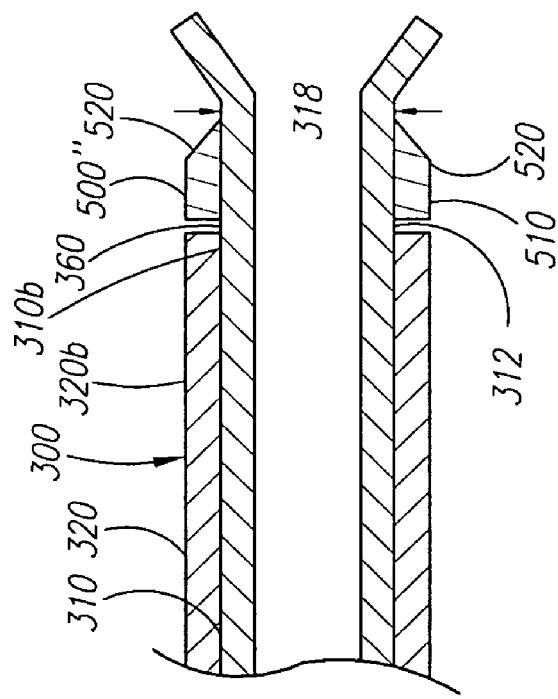
FIG. 7B illustrates the closure element of FIGS. 6A-G upon being disposed upon the carrier member of FIG. 3B.

In use, the closure element 500 is disposed within the carrier assembly 300. As shown in FIGS. 7A-B, for example, the reduced closure element 500' can be slidably received over the distally-increasing cross-section 318b of the distal end region 310b of the carrier member 310 and disposed about the periphery 312 of the carrier member 310 adjacent to the space 360. Since the reduced cross-section 530' of the reduced closure element 500' is less than the cross-section 318b of the distally-increasing cross-section 318b, the reduced closure element 500' must be temporarily radially deformed to be received over the distal end region 310b. Also, as the reduced closure element 500' is received over the distal end region 310b, the opposing tines 520 of the reduced closure element 500' engage the distal end region 310b. The reduced closure element 500' thereby forms the substantially tubular closure element 500" in the manner described in more detail above with reference to FIGS. 6E-G.

After being received over the distal end region 310b, the substantially tubular closure element 500" is disposed about the space 360, and the tines 520 are directed substantially distally as shown in FIG. 7B. As desired, one or more of the tines 520 can be disposed proximally of the distally-increasing cross-section 318b of the distal end region 310b, as illustrated in FIG. 7B, and/or can be at least partially disposed upon, and contact, the distally-increasing cross-section 318b of the distal end region 310b. To improve the engagement between the closure element 500 (shown in FIGS. 6A-B) and the blood vessel wall 620 and/or tissue 630 (collectively shown in FIG. 8A), the substantially tubular closure element 500" preferably is disposed on the carrier member 310 such that the tines 520 define a first plane that is substantially perpendicular to a second plane defined by the switching system 450 and/or the handles 390 (collectively shown in FIG. 5A).

Once disposed about the space 360, the substantially tubular closure element 500" can be retained on the outer periphery 312b of the carrier member 310 when distal end region 310b of the carrier member 310 and the distal end region 320b of the pusher member 320 are slidably received within the lumen 334 of the cover member 330 as illustrated in FIGS. 7C-D. When the cover member 330 is properly positioned within the carrier assembly 300, the distal end region 330b of the cover member 330 extends over the space 360 and defines the annular cavity 370 for retaining the substantially tubular closure element 500". As such, the substantially tubular closure element 500" is disposed substantially between the outer periphery 312b of the carrier member 310 and the inner periphery 332a of the cover member 330 such that the substantially tubular closure element 500" maintains the substantially tubular configuration with the tines 520 being directed substantially distally. As desired, the tube set 305 may radially compress the substantially tubular closure element 500" such that the substantially tubular closure element 500" enters and maintains a compressed tubular configuration. The body 510 of the substantially tubular closure element 500" can be disposed distally of the distal end region 320b of the pusher member 320, as illustrated in FIGS. 7C-D, or can engage the distal end region 320b, as desired.

Figure 8A:
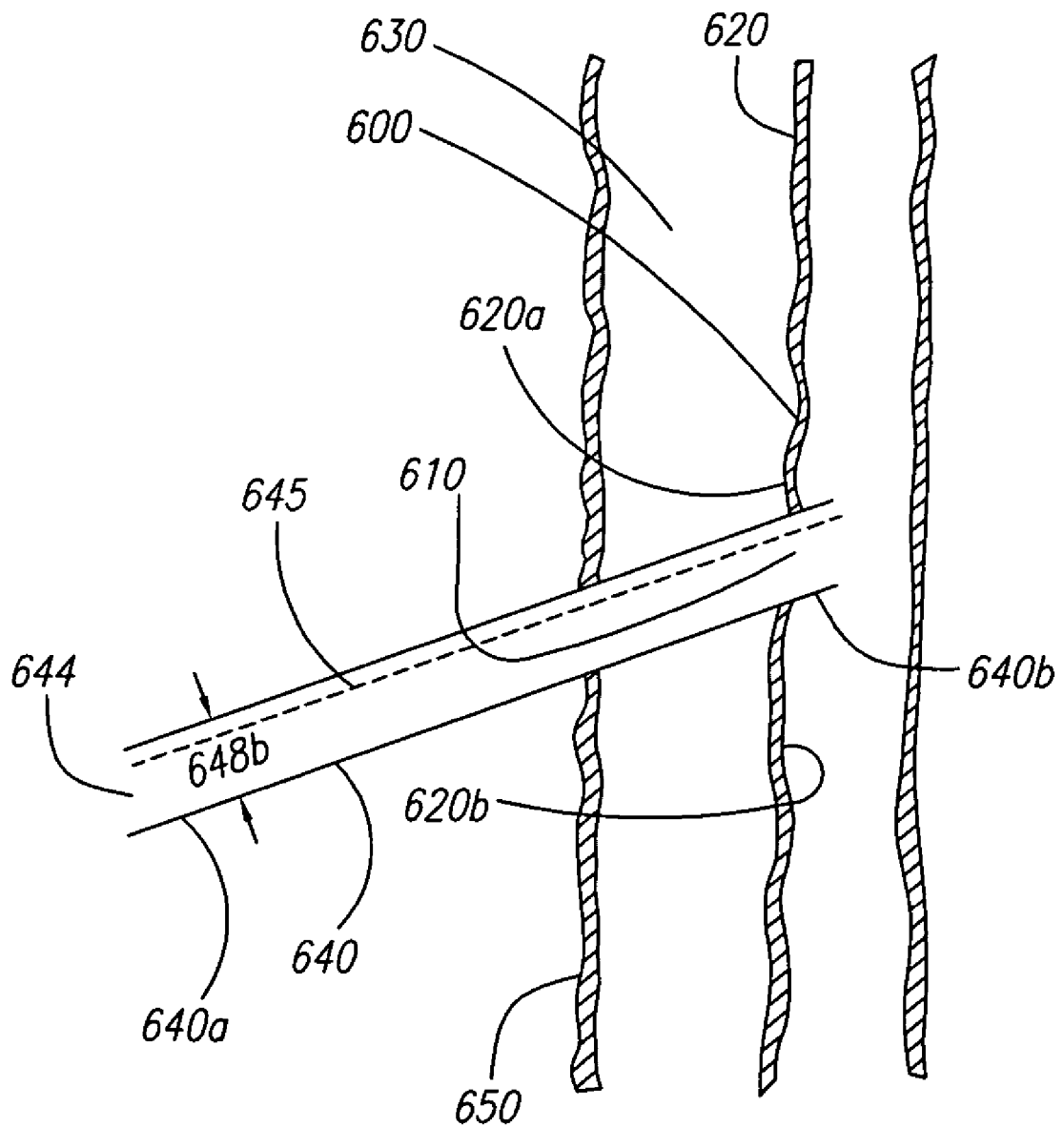
FIG. 8A illustrates a sheath that is positioned through tissue and into an opening formed in a wall of a blood vessel.

Turning to FIG. 8A, a sheath 640 may be inserted or otherwise positioned through skin 650 and tissue 630 and within the blood vessel 600 or other body lumen via the opening 610. Comprising a substantially flexible or semi-rigid tubular member, the sheath 640 has a proximal end region 640a and a distal end region 640b and includes a predetermined length and a predetermined cross-section, both of which can be of any suitable dimension. The sheath 640 also forms a lumen 644 that extends along a longitudinal axis of the sheath 640 and substantially between the proximal and distal end regions 640a, 640b. The lumen 644 can have any suitable internal cross-section 648b and is suitable for receiving one or more devices (not shown), such as a catheter, a guide wire, or the like. The lumen 644 is configured to slidably receive the tubular body 210 of the locator assembly 200 (shown in FIG. 4A) and/or the tube set 305 of the carrier assembly 300 (shown in FIG. 4A).

Since the internal cross-section 648b of the sheath 640 typically is less than or substantially equal to the predetermined cross-section 338b of the cover member 330, the sheath 640 may be configured to radially expand, such as by stretching, to receive the tube set 305. Alternatively, or in addition, the sheath 640 can be advantageously configured to split as the tube set 305 is received by, and advances within, the lumen 644 of the sheath 640, thereby permitting the apparatus 100 to access the blood vessel wall 620. To facilitate the splitting, the sheath 640 can include one or more splits 645, such as longitudinal splits, each split being provided in the manner known in the art. Each split 645 is configured to split the sheath 640 in accordance with a predetermined pattern, such as in a spiral pattern. It will be appreciated that, when the internal cross-section 648b of the sheath 640 is greater than the predetermined cross-section 338b of the cover member 330, it may not be necessary for the sheath 640 to be configured to radially expand and/or split.

The sheath 640 may be advanced over a guide wire or other rail (not shown) that was previously positioned through the opening 610 and into the blood vessel 600 using conventional procedures. Preferably, the blood vessel 600 is a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, or the like, may be inserted through the sheath 640 and advanced to a preselected location within the patient's body. For example, the devices may be used to perform a therapeutic or diagnostic procedure, such as angioplasty, atherectomy, stent implantation, and the like, within the patent's vasculature.

Figure 8B:
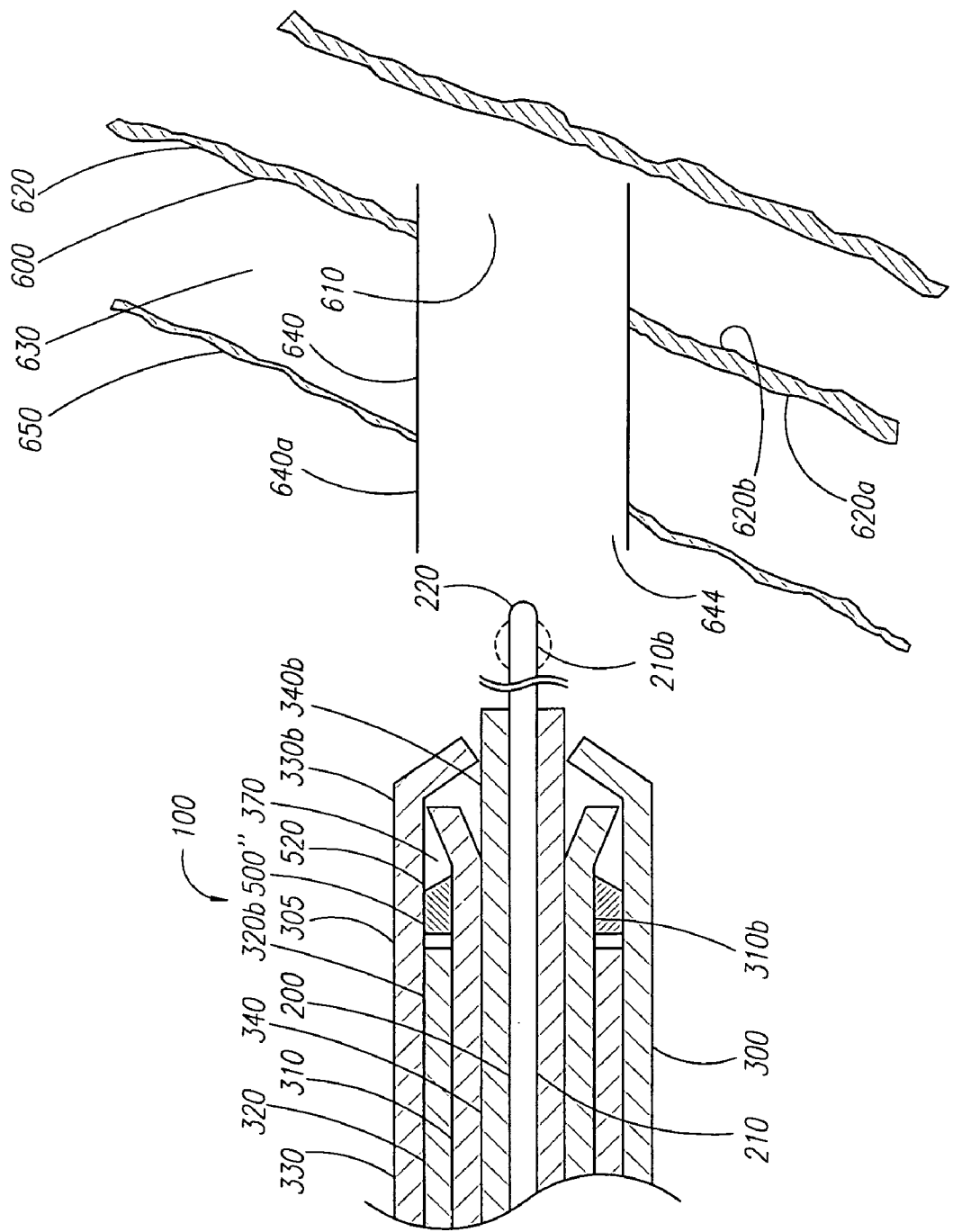
FIG. 8B illustrates the apparatus of FIG. 1 as prepared to be received by the sheath of FIG. 8A.
Figure 8D:
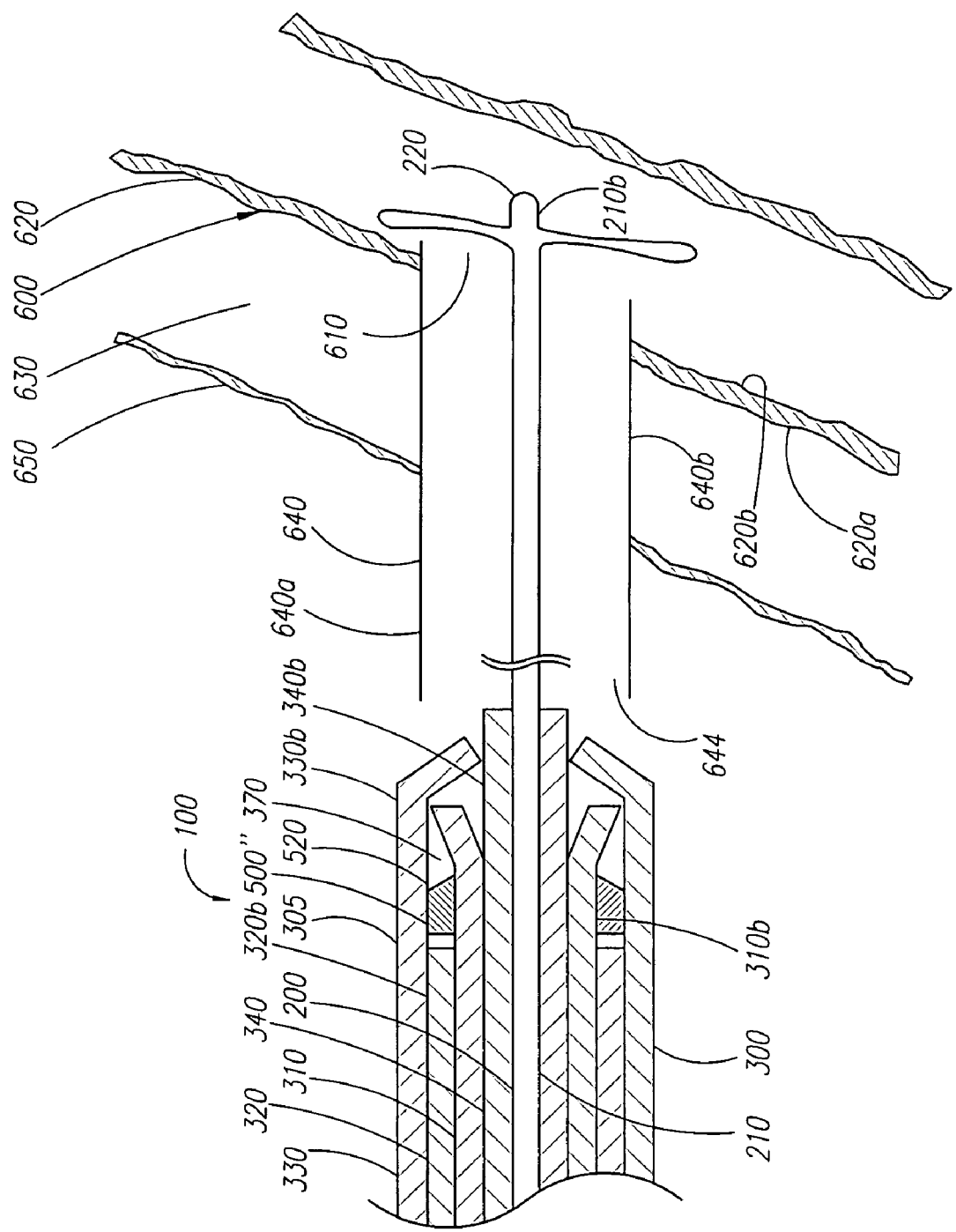
FIG. 8D illustrates a distal end region of the locator assembly of FIG. 8C extending into the blood vessel and being transitioned into an expanded state.

After the procedure is completed, the devices are removed from the sheath 640, and the apparatus 100 is prepared to be received by the lumen 644 of the sheath 640 as shown in FIG. 8B. Being in the unexpanded state, the distal end region 210b of the tubular body 210 of the locator assembly 200 is slidably received by the lumen 644 and atraumatically advanced distally into the blood vessel 600 as illustrated in FIGS. 8B-C. Once the distal end region 210b of the tubular body 210 extends into the blood vessel 600, the distal end region 210b can transition from the unexpanded state to the expanded state as shown in FIG. 8D by activating the switching system of the locator assembly 200.

Figure 8E:
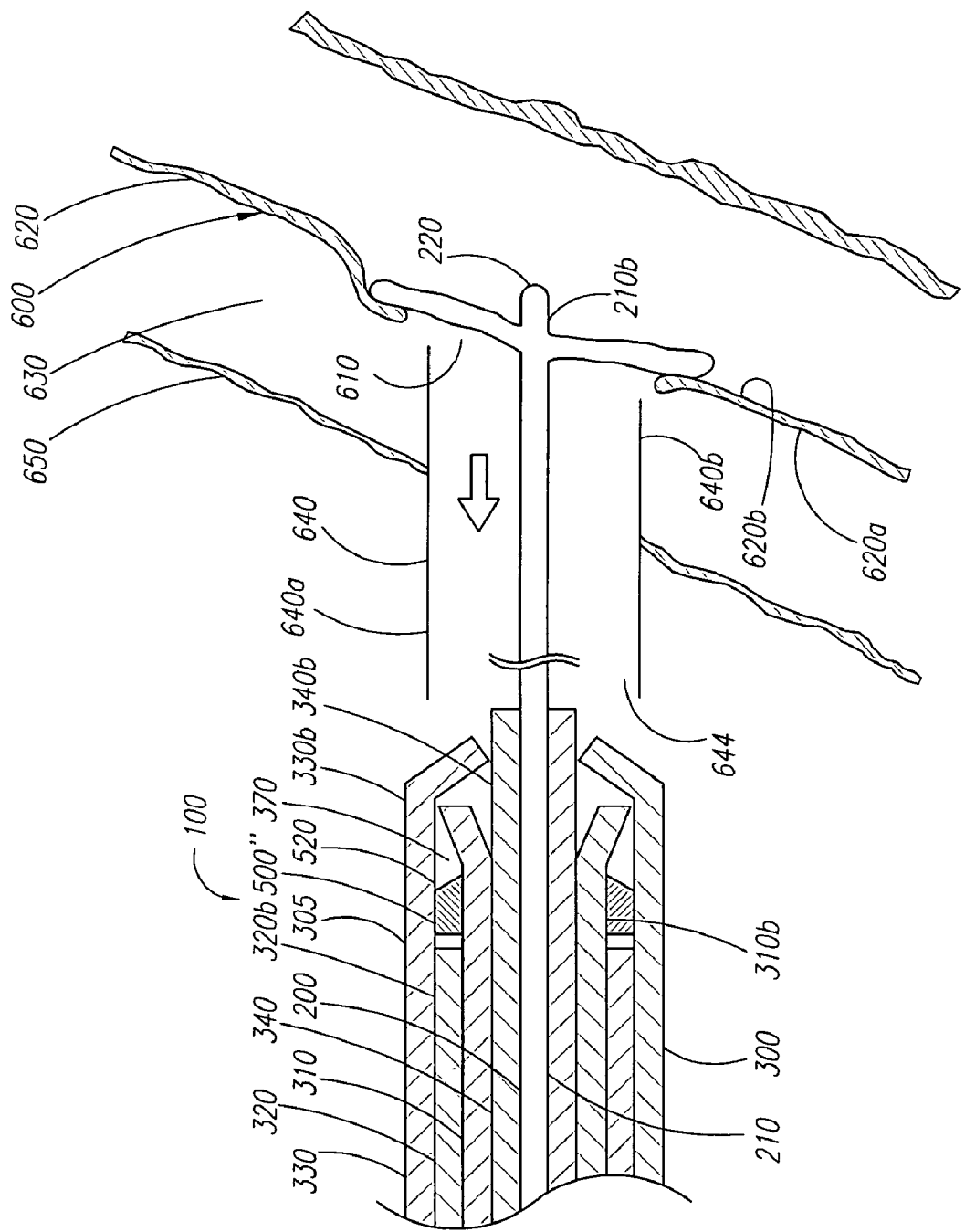
FIG. 8E illustrates the distal end region of FIG. 8D being retracted proximally to engage an inner surface of the blood vessel wall.

Turning to FIG. 8E, the apparatus 100 and the sheath 640 then are retracted proximally until the distal end region 210b is substantially adjacent to an inner surface 620b of the blood vessel wall 620. The distal end region 210b thereby draws the blood vessel wall 620 taut and maintains the proper position of the apparatus 100 as the blood vessel 600 pulsates. Since the expanded cross-section of the distal end region 210b is greater than or substantially equal to the cross-section of the opening 610 and/or the cross-section of the lumen 644, the distal end region 210b remains in the blood vessel 600 and engages the inner surface 620b of the blood vessel wall 620. The distal end region 210b can frictionally engage the inner surface 620b of the blood vessel wall 620, thereby securing the apparatus 100 to the blood vessel 600. The sheath 640 is retracted proximally such that the distal end region 640b of the sheath 640 is substantially withdrawn from the blood vessel 600, as shown in Fig. E, permitting the apparatus 100 to access the blood vessel wall 620.

As the apparatus 100 is being retracted, the apparatus 100 preferably also is axially rotated such that the first plane defined by the tines 520 of the substantially tubular closure element 500" is substantially parallel with a third plane defined by the blood vessel 600. Thereby, the engagement between the substantially tubular closure element 500" and the blood vessel wall 620 and/or tissue 630 can be improved because the tines 520 are configured to engage the blood vessel wall 620 and/or tissue 630 at opposite sides of the opening 610. If the substantially tubular closure element 500" is disposed on the carrier member 310 such that the first plane defined by the tines 520 is substantially perpendicular to the second plane defined by the switching system 450 and/or the handles 390 (collectively shown in FIG. 5A), for example, the apparatus 100 can be positioned such that the second plane defined by the switching system 450 and/or the handles 390 is substantially perpendicular to the third plane defined by the blood vessel 600.

Figure 8F:
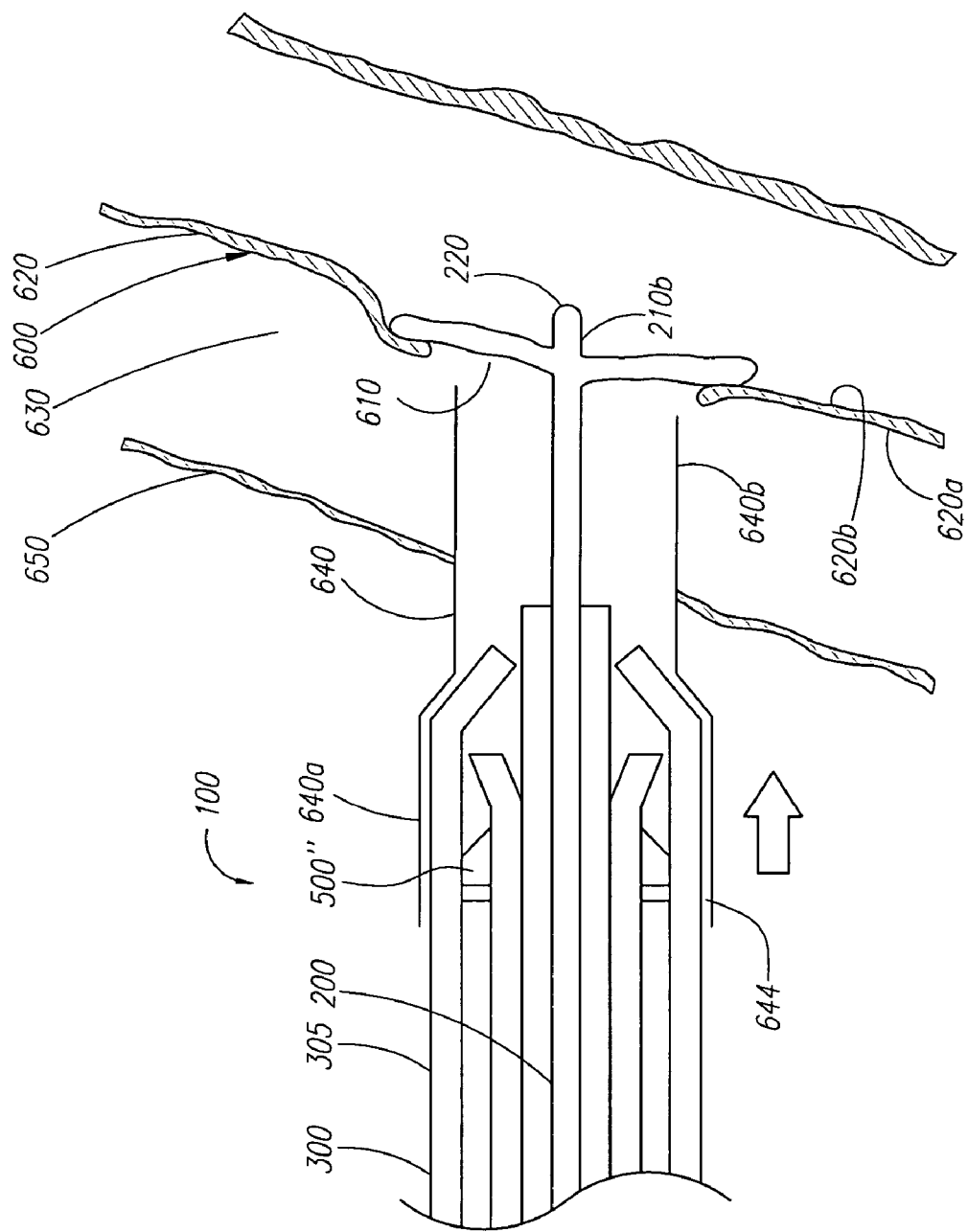
FIG. 8F illustrates a carrier assembly of the apparatus of FIG. 8B being advanced distally into the sheath of FIG. 8A once the distal end region of FIG. 8D has engaged the inner surface of the blood vessel wall.
Figure 8G:
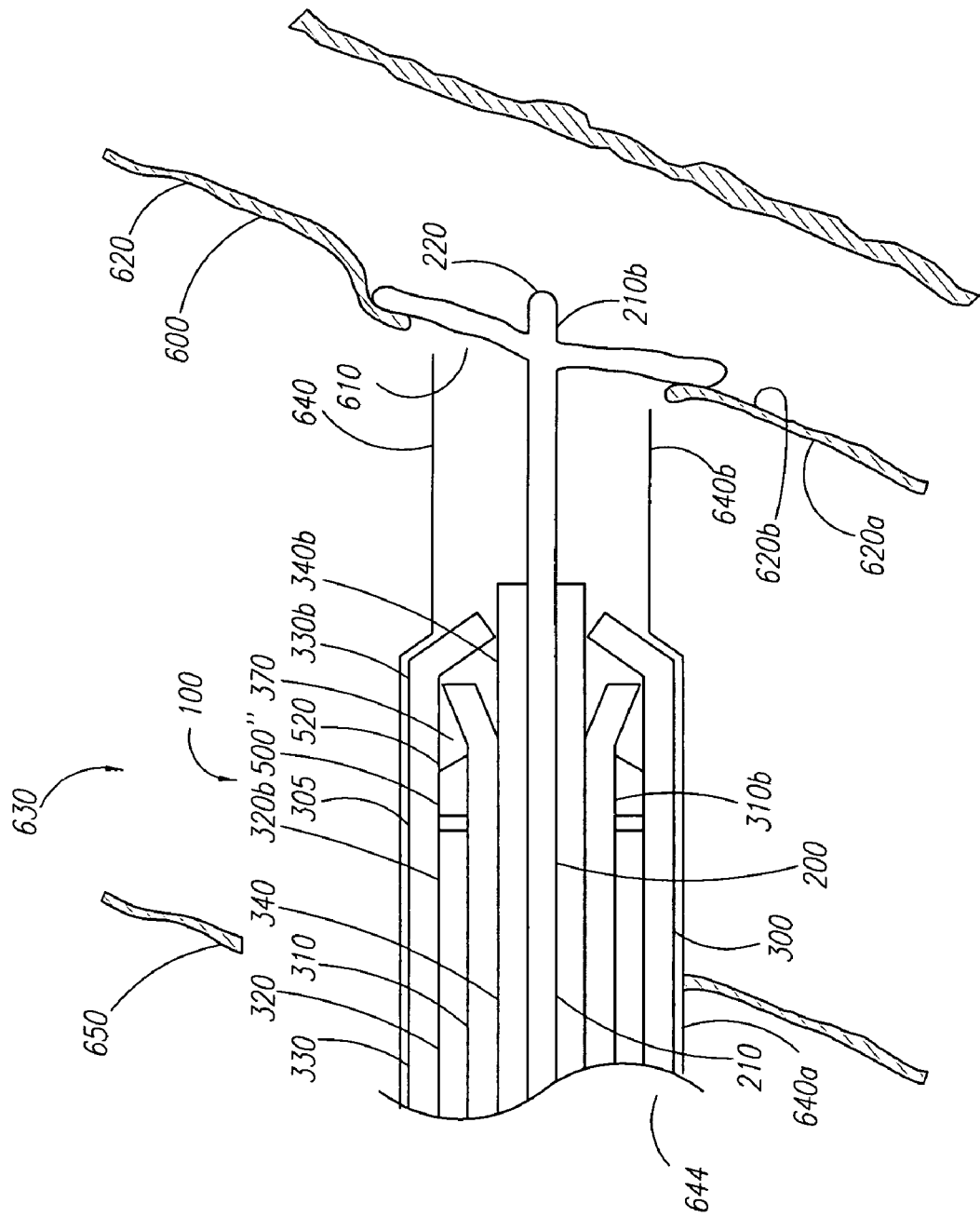
FIG. 8G illustrates relative positions of a tube set of the carrier assembly of FIG. 8F upon reaching a first predetermined position.

Once the distal end region 210b of the locator assembly 200 engages the inner surface 620b of the blood vessel wall 620, the tube release system 470 (shown in FIG. 4D) is activated to release the tube set 305, which can be advanced distally and received within the lumen 644 of the sheath 640 as illustrated in FIG. 8F. In the manner described in more detail above with reference to FIG. 8A, the sheath 640 can radially expand and/or split in accordance with the predetermined pattern as the tube set 305 advances because the internal cross-section 648b of the sheath 640 is less than or substantially equal to the predetermined cross-section 338b of the cover member 330. Being coupled, the carrier member 310, the pusher member 320, the cover member 330, and the support member 340 each advance distally and approach the first predetermined position as illustrated in FIG. 8G.

Upon reaching the first predetermined position, the tube set 305 is disposed substantially adjacent to the outer surface 620a of the blood vessel wall 620 adjacent to the opening 610 such that the blood vessel wall 620 adjacent to the opening 610 is disposed substantially between the expanded distal region 210b of the locator assembly 200 and the tube set 305. The cover member 330 and the support member 340 each decouple from the carrier member 310 and the pusher member 320 in the manner described in more detail above with reference to FIGS. 5A-C when the tube set 305 is in the first predetermined position. Thereby, the cover member 330 and the support member 340 preferably are inhibited from further axial movement and remain substantially stationary as the carrier member 310 and the pusher member 320 each remain coupled and axially slidable.

Figure 8H:
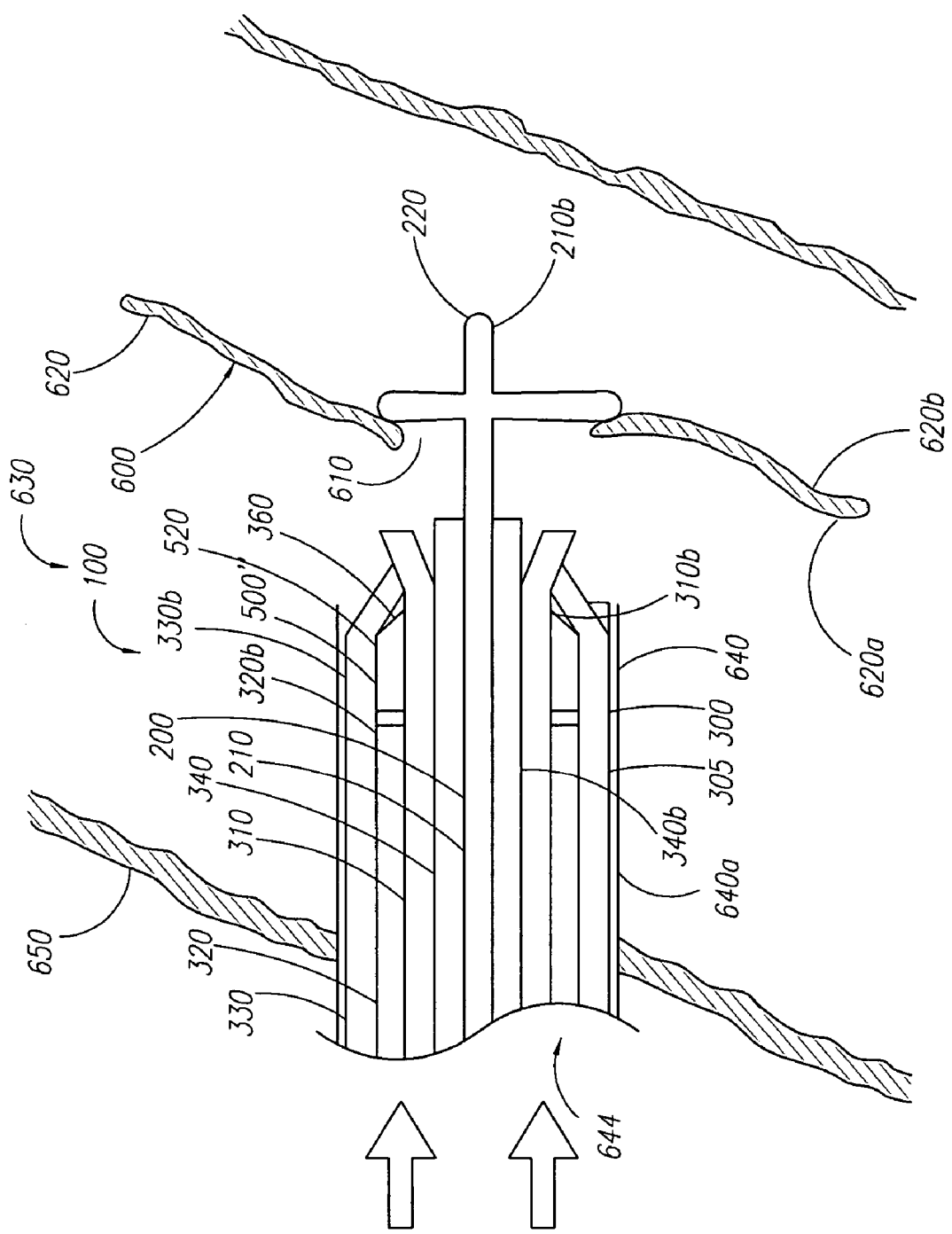
FIG. 8H illustrates the relative positions of the tube set of FIG. 8G upon reaching a second predetermined position.

As shown in FIG. 8H, the cover member 330 and the support member 340 remaining substantially stationary while the carrier member 310 and the pusher member 320 continue distally and approach the second predetermined position. As the carrier member 310 and the pusher member 320 distally advance toward the second predetermined position, the annular cavity 370 moves distally relative to the substantially-stationary cover member 330 such that the distal end region 330b of the cover member 330 no longer encloses the annular cavity 370. Thereby, the substantially tubular closure element 500" is not completely enclosed by the annular cavity 370 formed by the distal end regions 310b, 320b, and 330b of the carrier member 310, the pusher member 320, and the cover member 330.

Although not completely enclosed by the annular cavity 370, the substantially tubular closure element 500" is advantageously retained on the outer periphery 312b of the carrier member 310 by the distal end region 330b of the cover member 330 as illustrated in FIG. 8H. For example, by retaining the substantially tubular closure element 500" between the distal end region 330b of the cover member 330 and the distal end region 310b the carrier member 310, the apparatus 100 is configured to provide better tissue penetration. The timing between the deployment of the substantially tubular closure element 500" by the tube set 305 and the retraction and transition to the unexpanded state by the locator assembly 200 likewise is facilitated because the substantially tubular closure element 500" is retained between the distal end region 330b and the distal end region 310b. Further, the carrier member 310 and the cover member 330 operate to maintain the substantially tubular closure element 500" in the tubular configuration.

Figure 8I:
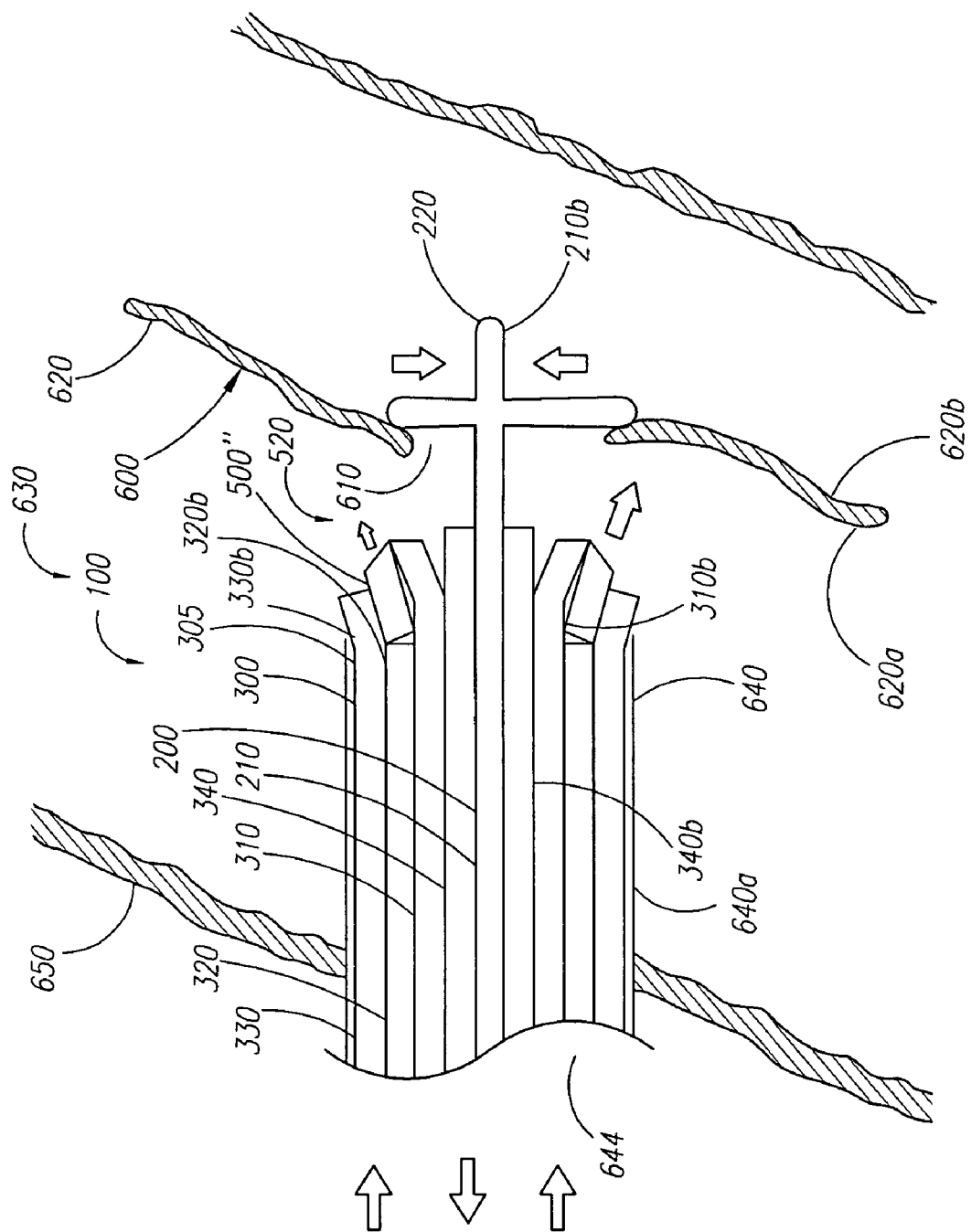
FIG. 8I illustrates a position of a pusher member of the tube set of FIG. 8H moving distally from the second predetermined position and beginning to distally deploy a closure element.

When the tube set 305 is in the second predetermined position, the carrier member 310 decouples from the pusher member 320 in the manner described in more detail above with reference to FIGS. 5A-C. Therefore, the carrier member 310, the cover member 330, and the support member 340 preferably are inhibited from further axial movement and remain substantially stationary; whereas, the pusher member 320 remains axially slidable. As the pusher member 320 continues distally, the distal end region 320b of the pusher member 320 engages the substantially tubular closure element 500" and displaces the substantially tubular closure element 500" from the space 360 as shown in FIG. 8I. Since the space 360 is substantially radially exposed, the pusher member 320 directs the substantially tubular closure element 500" over the distally-increasing cross-section of the distal end region 310b of the substantially-stationary carrier member 310 such that the cross-section 530' (shown in FIGS. 6F-G) of the substantially tubular closure element 500" begins to radially expand, preferably in a substantially uniform manner. As the substantially tubular closure element 500" traverses the distally-increasing cross-section of the distal end region 310b, the cross-section 530' of the substantially tubular closure element 500" radially expands beyond natural cross-section 530 (shown in FIGS. 6A-B) of the closure element 500.

Figure 8J:
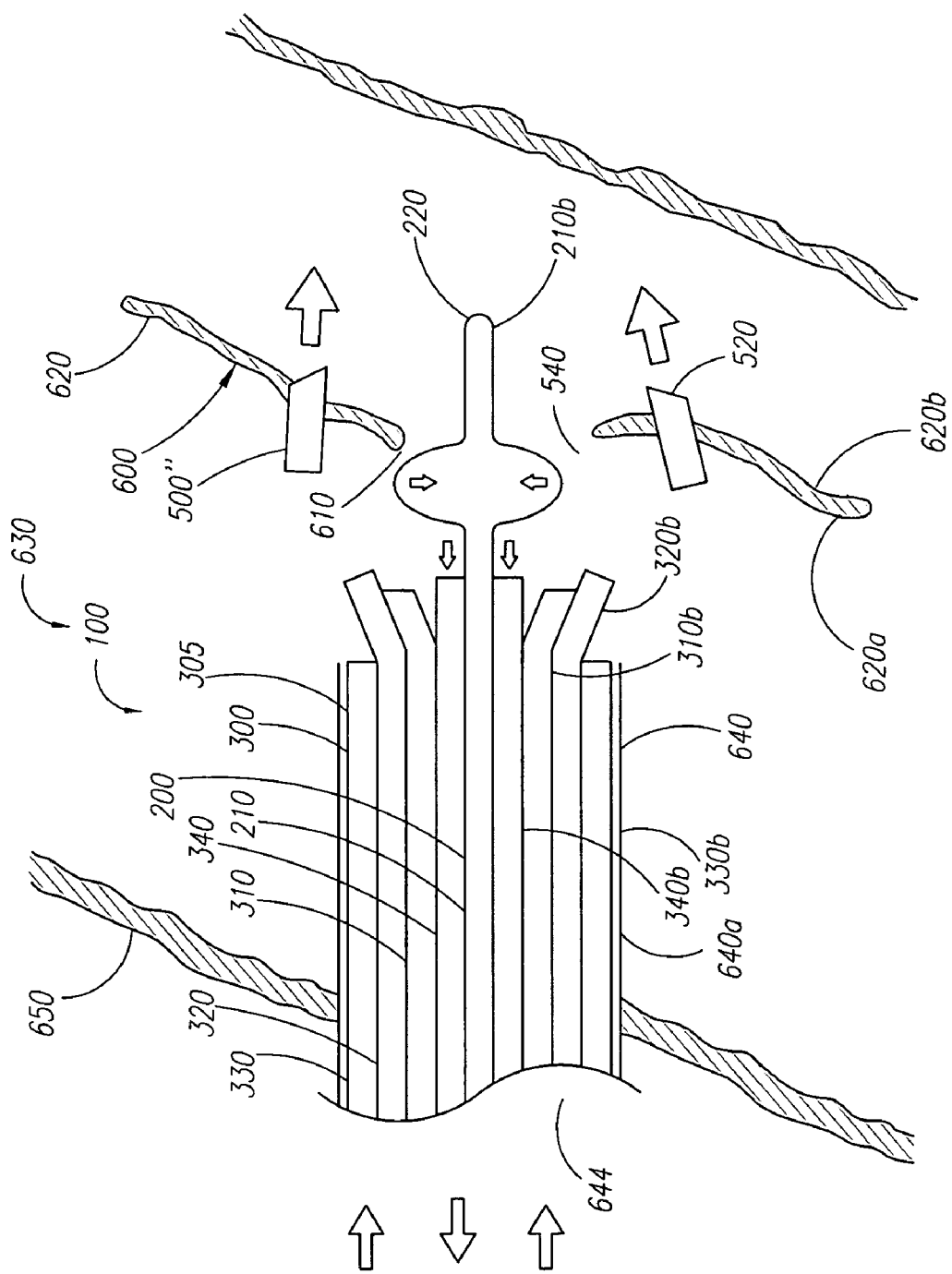
FIG. 8J illustrates the closure element of FIG. 8I upon being deployed and engaging tissue adjacent to the opening in the blood vessel wall.

Upon being directed over the distally-increasing cross-section of the distal end region 310b by the pusher member 320, the substantially tubular closure element 500" is distally deployed as illustrated in FIG. 8J. When the substantially tubular closure element 500" is deployed, the tines 520 can pierce and otherwise engage significant amount of the blood vessel wall 620 and/or tissue 630 adjacent to the opening 610. For example, the tines 520 can engage significant amount of the blood vessel wall 620 and/or tissue 630 because the cross-section 530' of the substantially tubular closure element 500" is expanded beyond natural cross-section 530 of the closure element 500 during deployment.

The distal end region 210b of the locator assembly 200 also begins to retract proximally and the locator release system 490 (shown in FIG. 4D) can be activated to transition from the expanded state to the unexpanded state as the substantially tubular closure element 500" is deployed as shown in FIG. 8J. Preferably, the distal end region 210b of the locator assembly 200 retracts proximally and transitions from the expanded state to the unexpanded state substantially simultaneously with the deployment of the substantially tubular closure element 500". As desired, the distal end region 210b may be configured to draw the blood vessel wall 620 and/or tissue 630 adjacent to the opening 610 proximally and into the channel 540 defined by the substantially tubular closure element 500". The tines 520 of the substantially tubular closure element 500" thereby can pierce and otherwise engage the drawn blood vessel wall 620 and/or tissue 630. Since the cross-section 530' of the substantially tubular closure element 500" is expanded beyond natural cross-section 530 of the closure element 500, a significant amount of the blood vessel wall 620 and/or tissue 630 can be drawn into the channel 540 and engaged by the tines 520.

Figure 8K:
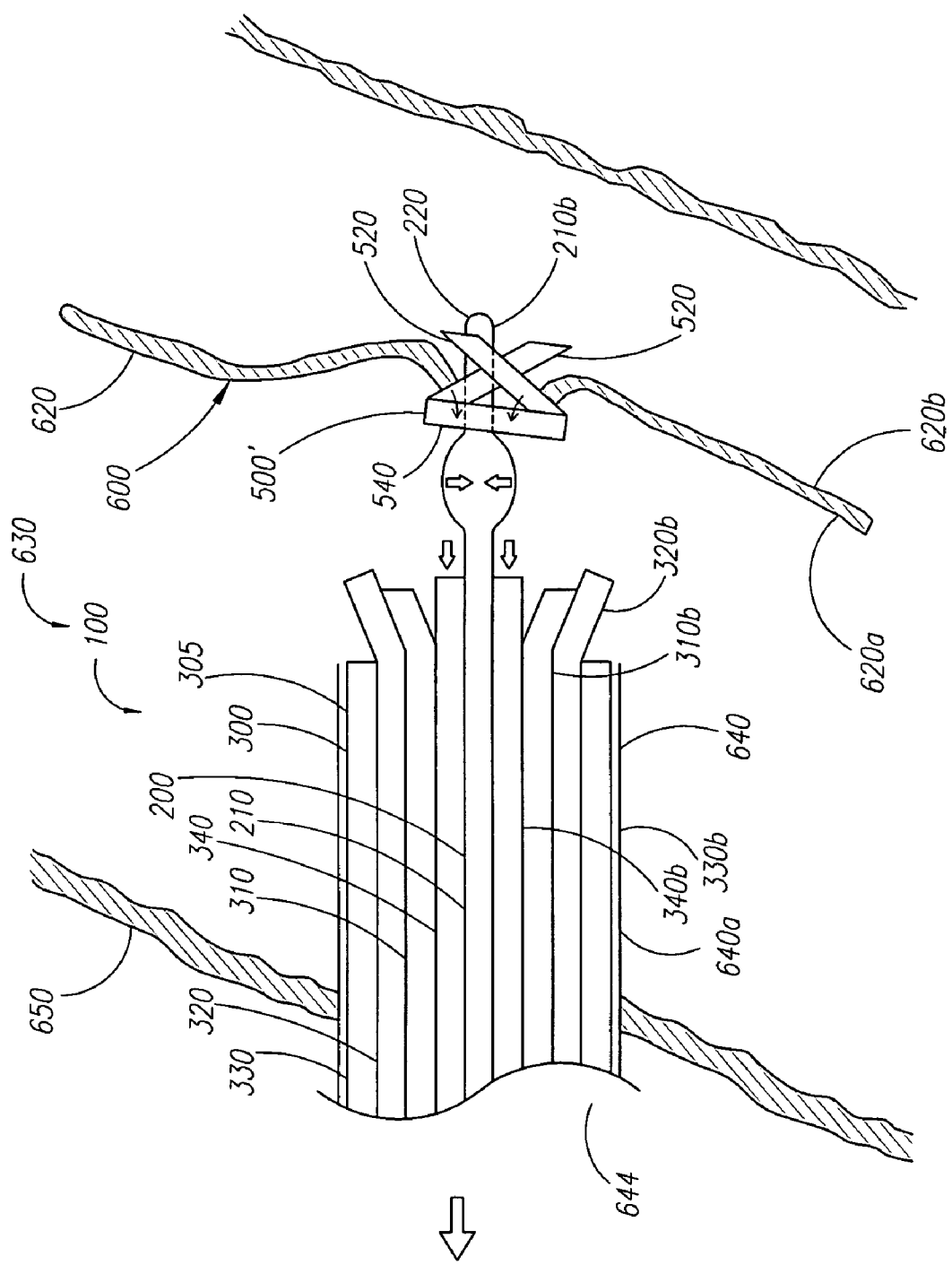
FIG. 8K illustrates the closure element of FIG. 8J transitioning from the substantially tubular configuration to the natural, planar configuration while engaging the engaged tissue.
Figure 8L:
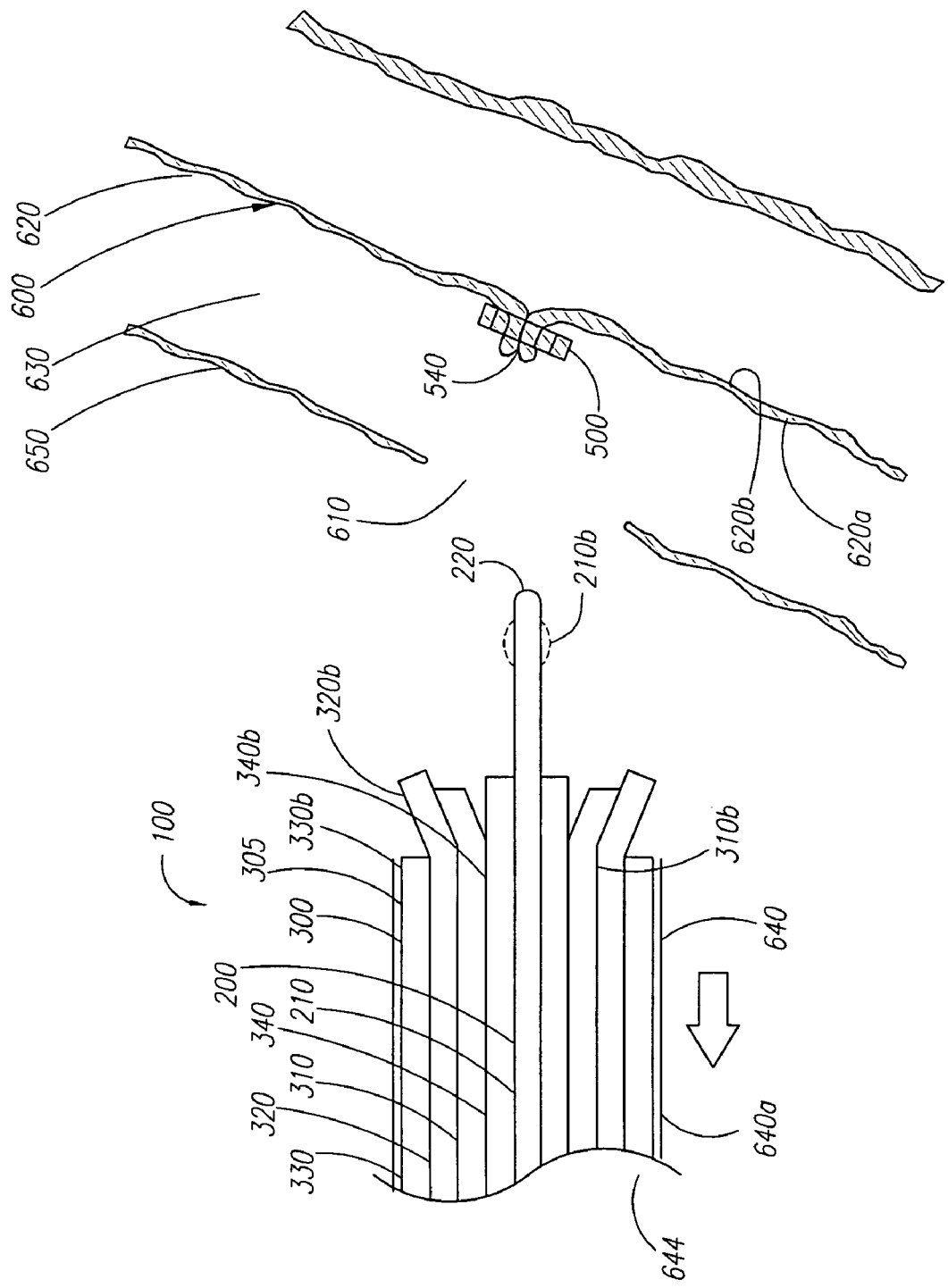
FIG. 8L illustrates the closure element of FIG. 8K drawing the engaged tissue substantially closed and/or sealed

Turning to FIG. 8K, the substantially tubular closure element 500", once deployed, begins to transition from the tubular configuration, returning to the natural, planar configuration with opposing tines 520 and a natural cross-section 530 of the closure element 500. Preferably, the substantially tubular closure element 500" substantially uniformly transitions from the tubular configuration to the natural, planar configuration. Rotating axially inwardly to form the opposing tines 520 of the closure element 500, the tines 520 draw the tissue 630 into the channel 540 as the substantially tubular closure element 500" forms the closure element 500. Also, the tissue 630 is drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500 as illustrated in FIG. 8L.

It will be appreciated that the closure element 500" may be constructed of other materials, that it may comprise alternative shapes, and that it may adopt alternative methods of operation such that the closure element 500" achieves closure of openings in blood vessel walls or other body tissue. In an additional non-limiting example, the closure element 500" is constructed of materials that use a magnetic force to couple a pair of securing elements in order to close an opening in the lumen wall or tissue. In this alternative embodiment, the closure element 500" may be of a unitary or multi-component construction having a first securing element positionable at a first position adjacent the opening, and a second securing element positionable at a second position adjacent the opening. The first and second securing elements are provided having a magnetic force biasing the first and second securing elements together, thereby closing the opening, or they are provided having a magnetic force biasing both the first and second securing elements toward a third securing element positioned in a manner to cause closure of the opening. The magnetic closure element 500" may be provided without tines 520, provided the magnetic force coupling the closure elements is sufficient to close the opening. Alternatively, the closure element 500" may be provided with a combination of the magnetic securing elements and tines 520 to provide a combination of coupling forces. Those skilled in the art will recognize that other and further materials, methods, and combinations may be utilized to construct the closure element 500" to achieve the objectives described and implied herein.

Figure 9:
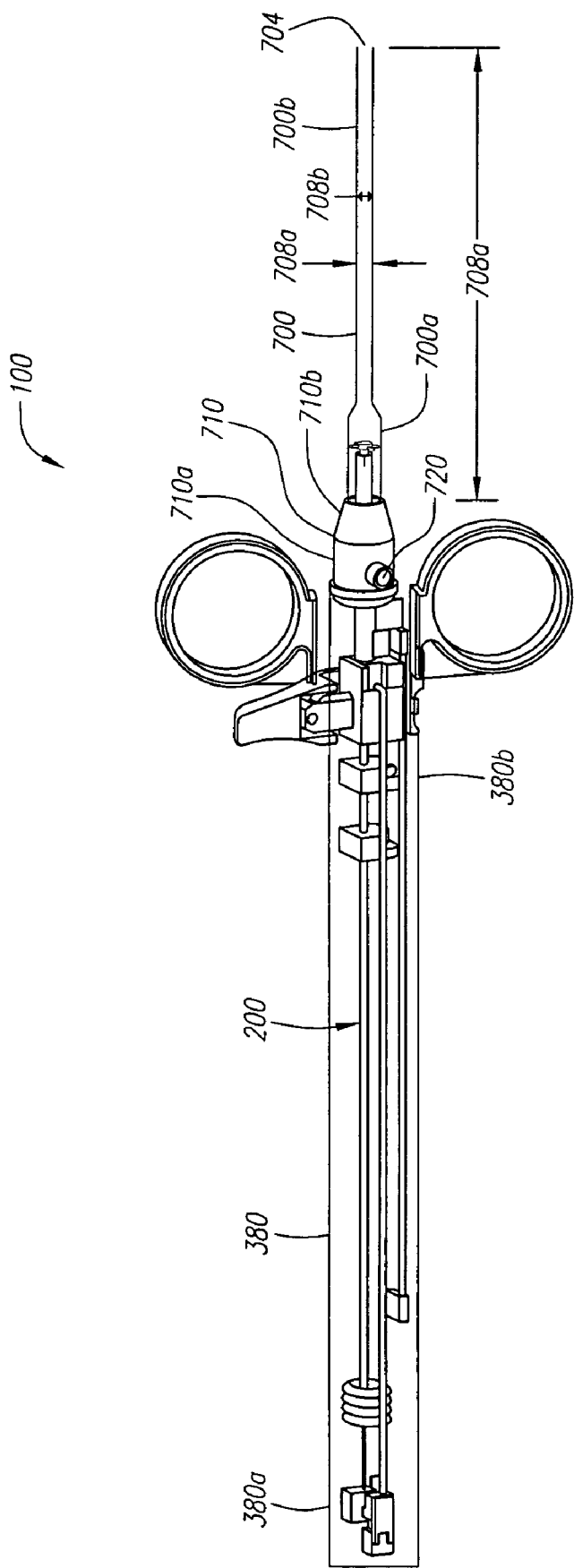
FIG. 9 illustrates one embodiment of an introducer sheath for the apparatus of FIG. 1.

It will be appreciated that the distal end region 380b of the housing 380 can be configured to couple with an introducer sheath 700 as shown in FIG. 9. Comprising a substantially flexible or semi-rigid tubular member, the introducer sheath 700 has a proximal end region 700a and a distal end region 700b and includes a predetermined length and a predetermined cross-section, both of which can be of any suitable dimension. The distal end region 700b is configured to facilitate insertion of the introducer sheath 700 through tissue 630 (shown in FIG. 8A) and/or into the opening 610 (shown in FIG. 8A) formed in and/or adjacent to the wall 620 (shown in FIG. 8A) of the blood vessel 600 (shown in FIG. 8A) or other body lumen. For example, the distal end region 430b can have a tapered tip (not shown) for facilitating substantially atraumatic introduction of the introducer sheath 700 through a passage formed in the tissue 630 and/or at least partially into the blood vessel wall 620, which is accessible via the passage. The introducer sheath 700 has an external cross-section 708b. The external cross-section 708b of introducer sheath 700 can be of any suitable dimension, and, as desired can be sized such that the introducer sheath 700 can be slidably received and advanced within the lumen 644 (shown in FIG. 8A) of the sheath 640.

The introducer sheath 700 also forms a lumen 704 that extends along a longitudinal axis of the introducer sheath 700 and substantially between the proximal and distal end regions 700a, 700b. The lumen 704 can have any suitable length 708a and internal cross-section 708b and is configured to slidably receive the tubular body 210 of the locator assembly 200 (shown in FIG. 4A) and/or the tube set 305 of the carrier assembly 300 (shown in FIG. 4A). Since the internal cross-section 708b of the introducer sheath 700 typically is less than or substantially equal to the predetermined cross-section 338b of the cover member 330, the introducer sheath 700 may be configured to radially expand, such as by stretching, to receive the tube set 305. Alternatively, or in addition, the introducer sheath 700 can be advantageously configured to split as the tube set 305 is received by, and advances within, the lumen 704 of the introducer sheath 700 in the manner described in more detail above with reference to the sheath 640 (shown in FIG. 8A). To facilitate the splitting, the introducer sheath 700 can include one or more splits (not shown), such as longitudinal splits, each split being provided in the manner known in the art. Each split is configured to split the introducer sheath 700 in accordance with a predetermined pattern, such as in a spiral pattern. It will be appreciated that, when the internal cross-section 708b of the introducer sheath 700 is greater than the predetermined cross-section 338b of the cover member 330, it may not be necessary for the introducer sheath 700 to be configured to radially expand and/or split.

The introducer sheath 700 can be coupled with the housing 380 via one or more cooperating connectors (not shown) such that the lumen 704 is substantially axially aligned with the tubular body 210 of the locator assembly 200 and/or the tube set 305 of the carrier assembly 300 and, as desired, may be removably and/or substantially permanently coupled with the housing 380. For example, a hub assembly 710 can be provided on the distal end region of the housing 380b and configured to couple with the proximal end region 700a of the introducer sheath 700. The proximal end region 430a of the introducer sheath 700 is coupled with, or otherwise provided on, a distal end region 710b of the hub assembly 710, such as via an adhesive, one or more cooperating connectors, and/or a thermo-mechanical joint.

The hub assembly 710 also includes a proximal end region 710a, which provides the one or more mating connectors for coupling the introducer sheath 700 with the housing 380 and forms a lumen (not shown), which extends substantially between the proximal end region 710a and the distal end region 710b. The lumen of the hub assembly 710 preferably has an internal cross-section or size that is greater than the internal cross-section or size of the lumen 704 of the introducer sheath 700. When the proximal end region 710a of the lumen 704 is properly connected with the hub assembly 710, the lumen of the hub assembly 710 is configured to communicate with the lumen 704 of the introducer sheath 700. As desired, the proximal end region 700a of the introducer sheath 700 may be flared to facilitate the connection between the introducer sheath 700 and the hub assembly 710.

When properly assembled, the hub assembly 710 preferably is substantially fluid tight such that the one or more devices can be inserted into the lumen 704 of the introducer sheath 700 without fluid passing proximally through the lumen 704. The hub assembly 710 can be made to be watertight, such as via one or more seals (not shown) and/or valves (not shown) in the manner known in the art. For example, the hub assembly 710 can include a thrust washer and/or valve, a guide for directing the devices into the lumen 704 of the introducer sheath 700, and/or a seal (collectively not shown). The various seals and/or guides can be coupled with the hub assembly 710 via, for example, one or more spacers and/or end caps (also collectively not shown).

As desired, the hub assembly 710 further can include one or more side ports 720. The side ports 720 can communicate with the lumen of the hub assembly 710 and/or the lumen 704 of the introducer sheath 700. At least one of the side ports 720 can be configured to be connected with, and to communicate with, tubing (not shown) to, for example, infuse fluids into the lumen 704 and through the introducer sheath 700. Alternatively, or in addition, at least one of the side ports 720 can provide a "bleed back" indicator, such as in the manner disclosed in the co-pending application Ser. No. 09/680,837. The disclosures of this reference and any others cited therein are expressly incorporated herein by reference.

An alternative embodiment of the apparatus is shown in FIGS. 10-15. The embodiment of FIGS. 10-15 has many identical or similar structures that perform identical or similar functions to the embodiment described above and in reference to the preceding Figures. In the description of the alternative embodiment below, and in FIGS. 10-15, components of the apparatus that are identical or substantially correspond to those previously described will bear the same reference numerals identified above with the addition of the prime (')identifier.

Turning to FIGS. 10 and 11, the locator assembly 200' is substantially similar to the structure described above in reference to FIGS. 2A-D, including a flexible or semi-rigid tubular body 210' (such as an elongate rail) with a longitudinal axis 216'. The tubular body 210' has a proximal end region 210a' and a distal end region 210b' and includes a predetermined length 218a' and a predetermined outer cross-section 218b', both of which can be of any suitable dimension. The distal end region 210b' of the locator assembly 200' preferably includes a substantially rounded, soft, and/or flexible distal end or tip 220' to facilitate atraumatic advancement and/or retraction of the distal end region 210b' into the blood vessel 600. As desired, a pigtail (not shown) may be provided on the distal end 220' to further aid atraumatic advancement of the distal end region 210b'.

The distal end region 210b' of the locator assembly 200' further is selectably controllable between an unexpanded state and an expanded state, in the manner described above in relation to FIGS. 2A-D. In the alternative embodiment shown in FIGS. 10A-B, the distal end region is shown in its expanded state, wherein the substantially flexible members 230' of the expansion elements 230' are flexed outward.

A control member 250', such as a rod, wire, or other elongate member, can be moveably disposed within a lumen (not shown) formed by the tubular body 210' and extending substantially between the proximal end region 210a' and the distal end region 210b'. The control member 250' has a proximal end region 250a' that is coupled with a control block 260', and a distal end region that is coupled with the distal end region 210b' of the locator assembly 200', the expansion elements 230', and/or the movable end regions 230c' of the substantially flexible members 230'. The control block 260' is preferably of a tubular shape and formed of a metal or rigid plastic, and is adapted to be retained in a control block cavity 265' (see FIG. 10B) formed on the internal surface of the housing bottom half 380b', to thereby maintain the control block 260' in a substantially fixed position relative to the housing 380'. The locator control system 240' can selectively transition the distal end region 210b', the expansion elements 230', and/or the substantially flexible members 230' between the unexpanded and expanded states by moving the tubular body 210' axially relative to the control member 250'.

Formed on the proximal end 210a' of the tubular body 210' is a tubular body block 270' having a proximal groove 271'. The tubular body block 270' is formed of metal, rigid plastic, or other substantially rigid material and is preferably formed integrally with or attached securely to the tubular body 210'. The proximal groove 271' and the proximal end of the tubular body block 270' have a shape adapted to cooperate with a pair of tabs 281a'-b' formed on a locator assembly block 280' whereby the tubular body block 270' is maintained in a fixed axial relationship with the locator assembly block 280'. In this way, the tubular body block 270' and tubular body 210' are advanced distally by distal advancement of the locator assembly block 280'.

A locator assembly spring 290' is located coaxially with and substantially surrounds a portion of the tubular body block 270'. The locator assembly spring 290' is located between and contacts the distal side of two of the tabs 281a formed on the locator assembly block 280', and the proximal side of a locator assembly spring stop 381' formed on the inner surface of the housing bottom half 380d' (see FIG. 10B). The locator assembly spring 290' so located provides a force biasing the locator assembly block 280' in the proximal direction relative to the housing 380'.

The locator assembly block 280' is preferably formed of metal, plastic, or other rigid material. A function of the locator assembly block 280' is to allow the user to apply a force causing distal movement of the tubular body 210' relative to the control member 250' to cause the locator assembly 200' to transition from the unexpanded state to the expanded state. The proximal end of the locator assembly block 280' has a slot 281' formed therein, the slot 281' preferably having a size sufficient to accommodate the control block 260' and the control block cavity 265', and to allow the locator assembly block 280' to travel axially relative to the housing 380'. The distal end of the locator assembly block 280' has a pair of distally extending forks 282a-b, with each of the forks 282a-b having a ramp 283a-b on its inward facing surface. Finally, the locator assembly block 280' has a pair of distally extending release tabs 284a-b, with each of the release tabs 284a-b having a detent 285a-b.

As shown in FIGS. 11A-B, the locator assembly block 280' is slidably received and retained within grooves formed in the proximal end of the housing 380', with the proximal end of the locator assembly block extending from the proximal end of the housing. The control block 260' and control block cavity 265 are located in the slot 281' formed in the proximal end of the locator assembly block 280'.

Figure 10A:
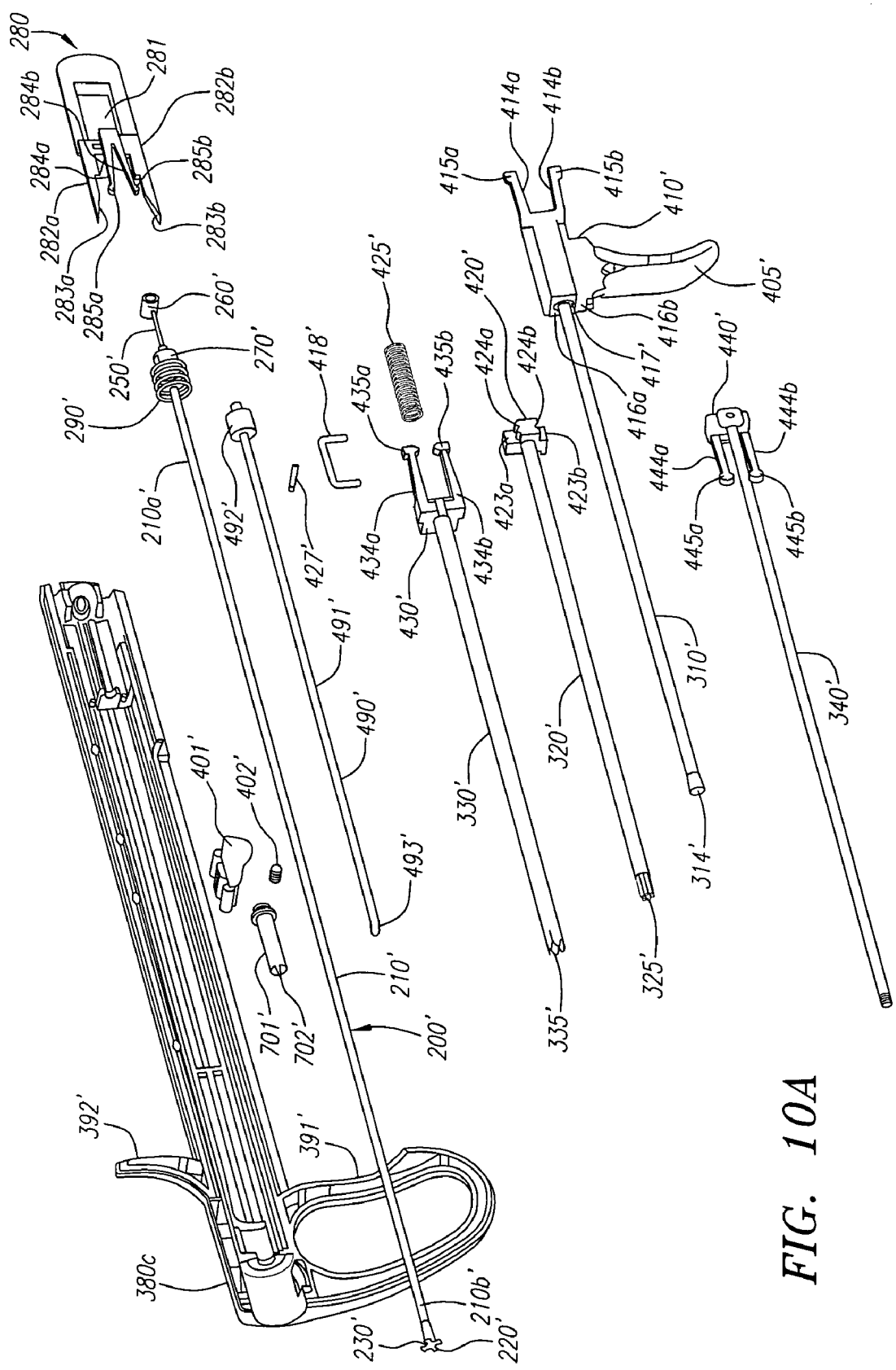
FIG. 10A illustrates an assembly view of the components included in an alternative embodiment of the apparatus for closing openings formed in blood vessel walls.
Figure 10B:
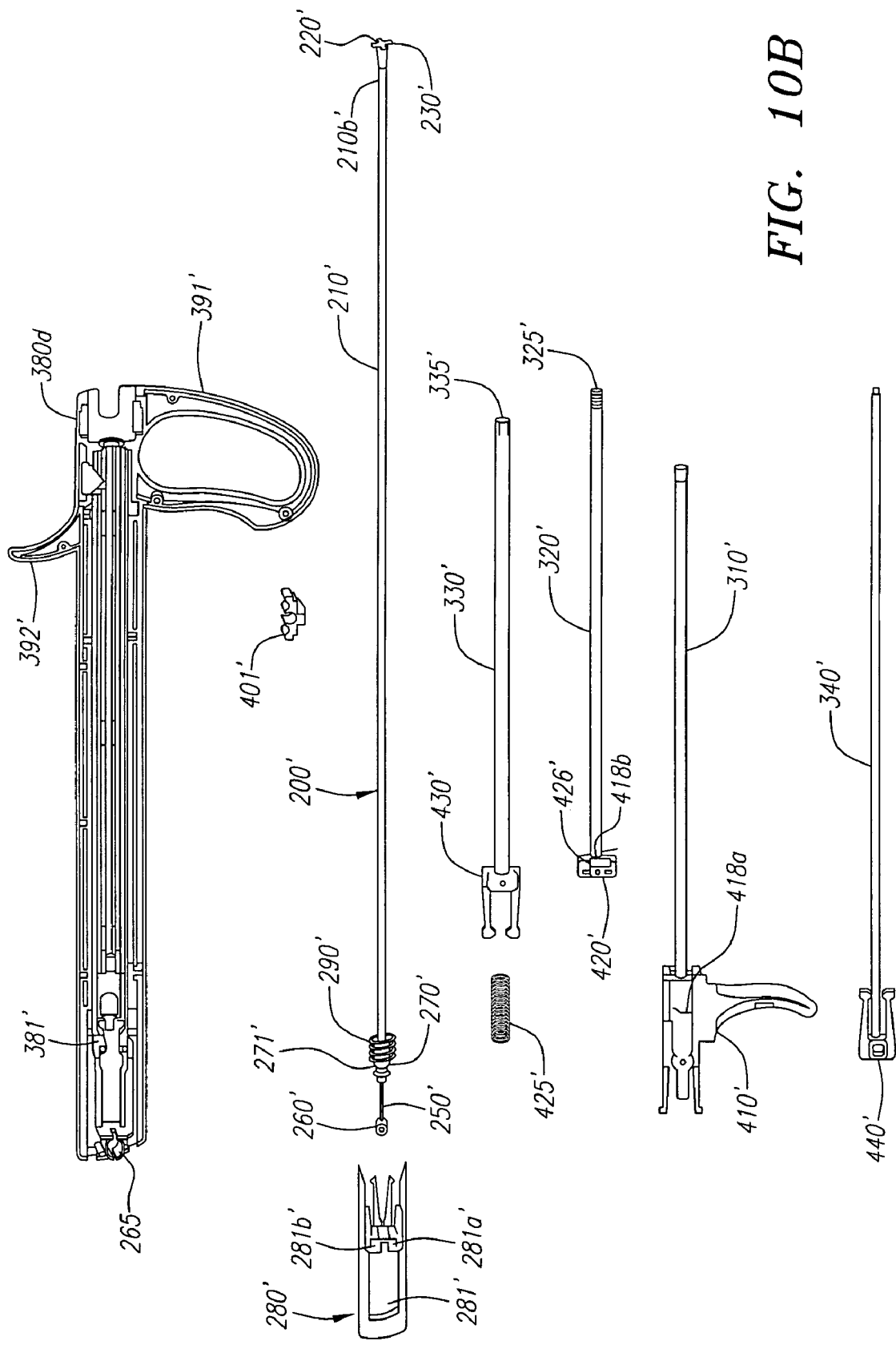
FIG. 10B illustrates an assembly view of the components shown in FIG. 10A, showing the reverse view of that shown in FIG. 10A.
Figure 15:
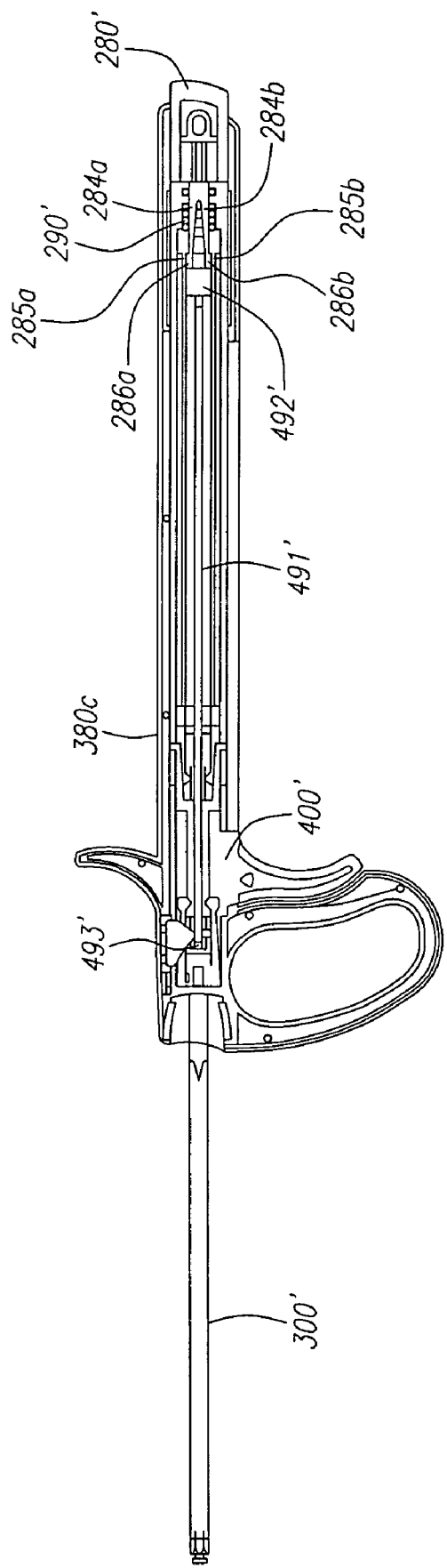
FIG. 15 illustrates a reverse view of the apparatus of FIGS. 11-14, showing the locator release system.

The locator release system 490' performs the function of releasing the locator assembly 200', thereby allowing the locator assembly 200' to transition from its expanded state to its unexpanded state. Turning to FIGS. 10A-B and FIG. 15, the locator release system 490' of the alternative embodiment of the apparatus includes a locator release rod 491' having a release tab spacer block 492' formed on its proximal end. The locator release rod 491' and release tab spacer block 492' are received and retained in a groove formed on the interior surface of the housing bottom half 380b. The release tab spacer block 492' is preferably integrally formed with or attached to the proximal end of the locator release rod 491', and is formed of metal, plastic, or other rigid material. As shown in FIG. 15, the release tab spacer block 492' has a shape and size adapted to fit between the release tabs 284a-b formed on the locator assembly block 280', thereby biasing the release tabs 284a-b outward and causing the outward facing detents 285a-b to engage a pair of retaining grooves 286a-b formed on the interior of the housing 380'. As long as the detents 285a-b are thus engaged with the retaining grooves 286a-b of the housing 380', the locator assembly block 280' is held in its axial position against the spring force imparted in the proximal direction by the locator assembly spring 290'. The distal end of the locator release rod 491' has an engagement member 493' that, in the preferred embodiment, comprises an inward bend on the distal end of the locator release rod. As described more fully below, the engagement member 493' on the locator release rod 491' is preferably positioned within the apparatus such that, when the closure element 500 is delivered, the engagement member 493' is engaged and caused to move axially in the distal direction, thereby disengaging the release tab spacer block 492' from the locator assembly block 280' and causing the locator assembly simultaneously to transition from its expanded state to the unexpanded state.

The alternative embodiment of the apparatus 100' includes a carrier assembly 300' that is coupled with, and slidable relative to, the locator assembly 200'. The carrier assembly 300' is configured to receive and retain the closure element 500 (shown in FIGS. 6A-B), which preferably is disposed substantially within the carrier assembly 300'. When the locator assembly 200' engages the inner surface 620b (shown in FIG. 8A) of the blood vessel wall 620 (shown in FIG. 8A), the carrier assembly 300' is further configured to position the closure element 500 substantially adjacent to the opening 610 and to deploy the closure element 500, as described elsewhere herein.

Turning to FIGS. 10A-B, the carrier assembly 300' includes a tube set comprising a carrier member 310', a pusher member 320', a cover member 330', and a support member 340'. The carrier member 310', pusher member 320', cover member 330', and support member 340' are preferably provided as a plurality of nested, telescoping members with a common longitudinal axis. The carrier member 310' is configured to receive and support the closure element 500. While being disposed on the carrier member 310', the closure element 500 preferably is deformed from the natural, planar configuration to form the substantially tubular closure element 500" (shown in FIGS. 6F-G) as described herein.

The carrier member 310' includes a proximal end region 310a' and a distal end region 310b'. The carrier member 310' can also define a lumen 314' that extends substantially between the proximal end region 310a' and the distal end region 310b' and that is configured to slidably receive at least a portion of the tubular body 210' of the locator assembly 200' and/or the support member 340'. Although the exterior cross-section of the carrier member 310' is substantially uniform, the distal end region 310b' of the carrier member 310' preferably has a cross-section that increases distally, as illustrated in FIGS. 10A-B, for substantially uniformly expanding the substantially tubular closure element 500" beyond the natural cross-section 530 of the closure element 500 when the substantially tubular closure element 500" is deployed. Alternatively, the distal end region 310b' can be formed with a uniform cross-section to deploy the closure element 500 without cross-sectional expansion.

The pusher member 320' has a proximal end region 320a' and a distal end region 320b' and is coupled with, and slidable relative to, the carrier member 310'. The pusher member 320' includes a predetermined length and a predetermined cross-section, both of which can be of any suitable dimension and can be configured to slidably receive the carrier member 310' such that the distal end region 320b' of the pusher member 320' is offset proximally from the distal end region 310b' of the carrier member 310'. As desired, the predetermined length of the pusher member 320' can be greater than or substantially equal to the predetermined length of the carrier member 310'. The predetermined length of the pusher member 320' preferably is less than the predetermined length of the carrier member 310' such that the carrier member 310' and the pusher member 320' at least partially define a space 360' distal to the distal end region 320b' of the pusher member 320' and along the periphery of the carrier member 310'.

The pusher member 320' preferably is substantially tubular and can define a lumen 324' that extends substantially between the proximal end region 320a' and the distal end region 320b' and that is configured to slidably receive at least a portion of the carrier member 310'. The cross-section of the pusher member 320' preferably is substantially uniform, and the distal end region 320b' of the pusher member 320' can comprise one or more longitudinal extensions 325', which extend distally from the pusher member 320' and along the periphery of the carrier member 310'. The longitudinal extensions 325' preferably are biased such that the longitudinal extensions 325' extend generally in parallel with the common longitudinal axis of the carrier assembly tube set. The longitudinal extensions 325' are sufficiently flexible to expand radially, and yet sufficiently rigid to inhibit buckling, as the distal end region 320b' is directed distally along the carrier member 310' and engage the distally-increasing cross-section of the distal end region 310b' of the carrier member 310' to deploy the substantially tubular closure element 500".

The cover member 330' is configured to retain the substantially tubular closure element 500" substantially within the carrier assembly 300' prior to deployment. Being coupled with, and slidable relative to, the pusher member 320', the cover member 330' has a proximal end region 330a' and a distal end region 330b' and includes a predetermined length and a predetermined cross-section, both of which can be of any suitable dimension. Preferably being formed as a substantially rigid, semi-rigid, or flexible tubular member, the cover member 330' has an inner periphery and an outer periphery and can define a lumen 334'. The lumen 334' extends substantially between the proximal and distal end regions 330a', 330b' of the cover member 330' and can be configured to slidably receive at least a portion of the pusher member 320'. When the cover member 330' is properly positioned within the carrier assembly 300', the distal end region 330b' is configured to extend over the space 360', thereby defining an annular cavity 370' for receiving and retaining the substantially tubular closure element 500".

The cross-section of the cover member 330' preferably is substantially uniform, and the distal end region 330b' of the cover member 330' preferably comprises one or more longitudinal extensions 335', which extend distally from the cover member 330' and along an outer periphery of the pusher member 320' (see FIG. 3D). Although the longitudinal extensions 335' can extend generally in parallel with common longitudinal axis 350', the longitudinal extensions 335' preferably are biased such that the plurality of longitudinal extensions 335' extend substantially radially inwardly as illustrated in FIGS. 3A and 3D. Thereby, the longitudinal extensions 335' can at least partially close the lumen 334' substantially adjacent to the distal end region 330b' of the cover member 330'. To permit the substantially tubular closure element 500" to be deployed from the annular cavity 370', the longitudinal extensions 335' preferably are sufficiently flexible to expand radially to permit the distal end region 310b' of the carrier member 310' to move distally past the cover member 330' to open the annular cavity 370' such that the distal end region 330b' no longer extends over the space 360'.

If the carrier assembly 300' is assembled as the plurality of nested, telescoping members as shown in FIG. 3A, the carrier member 310' is at least partially disposed within, and slidable relative to, the lumen 324' of the pusher member 320'. The pusher member 320', in turn, is at least partially disposed within, and slidable relative to, the lumen 334' of the cover member 330'. To couple the carrier assembly 300' with the locator assembly 200', the tubular body 210' of the locator assembly 200' is at least partially disposed within, and slidable relative to, the lumen 314' of the carrier member 310'. The longitudinal axis of the locator assembly 200' preferably is substantially in axial alignment with the common longitudinal axis of the carrier member 310', the pusher member 320', and the cover member 330'.

The tube set 305 preferably also includes a support member 340' as shown in FIGS. 10A-B. The support member 340' is configured to slidably receive the tubular body 210' of the locator assembly 200' and to provide radial support for the distal end region 210b' of the tubular body 210' when the locator assembly 200' is coupled with the carrier assembly 300'. The carrier assembly 300' can advantageously include the support member 340', for example, if the tubular body 210' is not sufficiently rigid or under other circumstances in which support for the tubular body 210' might be desirable. It also will be appreciated that the support member 340' also can be configured to inhibit the plurality of longitudinal extensions 335', which extend from the distal end region 330b' of the cover member 330', from expanding prematurely when the closure element 500 is deployed. If the longitudinal extensions 335' were to expand prematurely, they may become hung up on the introducer sheath 640 or other delivery member (in an introducer sheath or delivery member is used), the tissue 630, or the wall 620 of the blood vessel. This may interfere with the proper advancement or other movement of the cover member 330' and the carrier assembly 300'.

Preferably being formed as a substantially rigid, semi-rigid, or flexible tubular member, the support member 340' includes a proximal end region 340a' and a distal end region 340b'. Having an outer periphery, the support member 340' can define a lumen 344' that extends substantially between the proximal end region 340a' and the distal end region 340b' and that is configured to slidably receive and support at least a portion of the tubular body 210' of the locator assembly 200'. The support member 340', in turn, can be at least partially slidably disposed within the lumen 314' of the carrier member 310' such that the tubular body 210' of the locator assembly 200' is coupled with, and slidable relative to, the carrier member 310' in the manner described in more detail above. The support member 340' has a predetermined length and a predetermined cross-section, both of which can be of any suitable dimension, and the cross-section preferably is substantially uniform. Although shown and described as being substantially separate for purposes of illustration, it will be appreciated that the carrier member 310', the pusher member 320', the cover member 330', and/or the support member 340' can be provided, in whole or in part, as one or more integrated assemblies.

The carrier assembly 300' also can include a housing 380', the top half 380c of which is illustrated in FIG. 10A, and the bottom half 380b of which is shown in FIG. 10B. Preferably being formed as an elongate member with a longitudinal axis, the housing 380' has an outer periphery and includes a proximal end region 380a' and a distal end region 380b'. Thereby, when the apparatus 100' is properly assembled, the tubular body 210' of the locator assembly 200' is at least partially disposed within, and slidable relative to, the tube set 305 such that the distal end region 210b' of the tubular body 210' extends beyond the distal end regions 310b', 320b', 330b', and/or 340b'. The tubular body 210', the carrier member 310', the pusher member 320', the cover member 330', and, if provided, the support member 340' are at least partially disposed within, and slidable relative to, the housing 380', and the respective distal end regions 210b', 310b', 320b', 330b', and 340b' extend from the distal end region 380b' of the housing 380' such that the common longitudinal axis 350' of the tube set 305 is substantially axially aligned with the longitudinal axis 386' of the housing 380'. Being configured to slidably retain the respective proximal end regions 210a', 310a', 320a', 330a', and 340a', the housing 380' supports the tube set 305 and can have one or more handles 391', 392' to facilitate use of the apparatus 100'. The handles 391', 392' extend substantially radially from the outer periphery of the housing 380' and can be provided in the manner known in the art.

When the apparatus 100' is properly assembled, the tubular body 210' of the locator assembly 200' is at least partially disposed within, and slidable relative to, the tube set 305 of the carrier assembly 300' such that the distal end region 210b' of the tubular body 210' extends beyond the distal end regions 310b', 320b', 330b', and/or 340b'. Further, the proximal end region 210a' of the tubular body 210' and the proximal end regions 310a', 320a', 330a', and/or 340a' of the tube set 305 are at least partially disposed within, and slidable relative to, the housing 380'. The switching system of the locator assembly 200' and a switching system 450' of the triggering system 400' preferably are accessible external to the housing 380' as shown in FIGS. 11-15.

As shown in FIGS. 11-15, the triggering system 400' of the alternative embodiment of the apparatus 100' can be disposed substantially within the housing 380'. The triggering system 400' is configured to control the relative axial movement and/or positioning of the respective distal end regions 310b', 320b', 330b', and 340b' of the tube set 305 and/or the distal end region 210b' of the locator assembly 200'. Axial motion of one or more of the carrier member 310', the pusher member 320', the cover member 330', and the support member 340' and/or the tubular body 210' can be attained, for example, by applying an axial force to the switching system 450'.

The triggering system 400' includes a set of block members—a carrier block 410', a pusher block 420', a cover block 430', and a support block 440'—each of which is formed integrally with or securely attached to its respective member of the carrier assembly 300'. The block members are adapted to selectably couple and decouple the carrier member 310', the pusher member 320', the cover member 330', and the support member 340' relative to one another in order to provide axial movement of those components in a predetermined manner intended to deliver the closure element 500 in the manner described herein. For example, when the carrier assembly 300' reaches a first predetermined distal position, the support member 340' can be decoupled from the carrier member 310', the pusher member 320', and the cover member 330' and is thereafter substantially inhibited from further axial movement. Thereby, the carrier member 310', the pusher member 320', and the cover member 330' may be directed distally as the support member 340' remain substantially stationary. Subsequently, the carrier member 310' and the cover member 330' can be decoupled from the pusher member 320' and thereafter inhibited from further axial movement. Thereby, the pusher member 320' may be directed distally as the support member 340', carrier member 310', and cover member 330' remain substantially stationary, as described more fully herein.

The carrier block 410' is disposed on the proximal end region 310a' of the carrier member 310' and includes a trigger extension 405' that extends through a slot in the housing 380' to the exterior of the housing 380' to be accessible to the user. The carrier block 410' includes a pair of grooves 413a-b formed on a peripheral surface of the carrier block 410', the grooves 413a-b being adapted to receive and retain a pair of tabs 445a-b formed on a pair of forks 444a-b extending distally from the support block 440', thereby selectably coupling the support block 440' to the carrier block 410'. The carrier block 410' also includes a pair of distal tabs 416a-b extending from the distal end of the carrier block 410', and adapted to engage a pair of slots 423a-b formed on the proximal end of the pusher block 420'.

The carrier block 410' also includes a pair of forks 414a-b extending in the proximal direction from the proximal end of the carrier block, each of the forks having an outward directed tab 415a-b at its proximal end. The tabs 415a-b are adapted to selectably engage a pair of slots 387a-b formed on the interior surface of the housing 380' near its proximal end and, when so engaged, to fix the axial position of the carrier block 410'—and, with it, the carrier assembly 300'—relative to the housing 380'. The tabs 415a-b are disengaged from the slots in the housing when the locator assembly block 280' is moved axially in the distal direction in the following manner (see FIG. 11B). As the locator assembly block 280' is advanced distally, the interior surfaces of the ramps 283a-b on the locator assembly block forks 282a-b engage the exterior surfaces of the tabs 415a-b and cause the carrier block forks 414a-b to flex inward, releasing the tabs 415a-b from the slots in the housing, thereby freeing the carrier block 410'— and the carrier assembly 300'—to move axially. Thus, axial movement of the carrier block 410' within the apparatus is inhibited until the locator assembly block 280' is advanced to transition the locator assembly 200' to the expanded condition, simultaneously releasing the tabs 415a-b on the carrier block 410'.

The pusher block 420' is disposed on the proximal end region 320a' of the pusher member 320'. As described above, the pusher block 420' includes a pair of slots 423a-b formed on its proximal end that are adapted to selectably engage the pair of distal tabs 416a-b extending from the distal end of the carrier block 410'. The pusher block 420' also includes a pair of grooves 424a-b formed on its peripheral surface, the grooves 424a-b being adapted to engage a pair of tabs 435a-b formed on a pair of forks 424a-b extending from the proximal side of the cover block 430' to selectably couple the cover block 430' to the pusher block 420'.

The cover block 430' is disposed on the proximal end region 330a' of the cover member 330'. As described above, the cover block 430' includes a pair of forks 424a-b extending from the proximal end of the cover block 430', each of the forks having an inward directed tab 435a-b that are adapted to engage the grooves 424a-b on the peripheral surface of the pusher block 420' to selectably couple the cover block 430' to the pusher block 420'.

The support block 440' is disposed on the proximal end region 340a' of the support member 340'. As described above, the support block includes a pair of forks 444a-b extending from the distal end of the support block 440', each of the forks having an inward directed tab 445a-b that are adapted to engage the grooves 413a-b formed on the surface of the carrier block 410' to selectably couple the support block 440' to the carrier block 410'.

Figure 12:
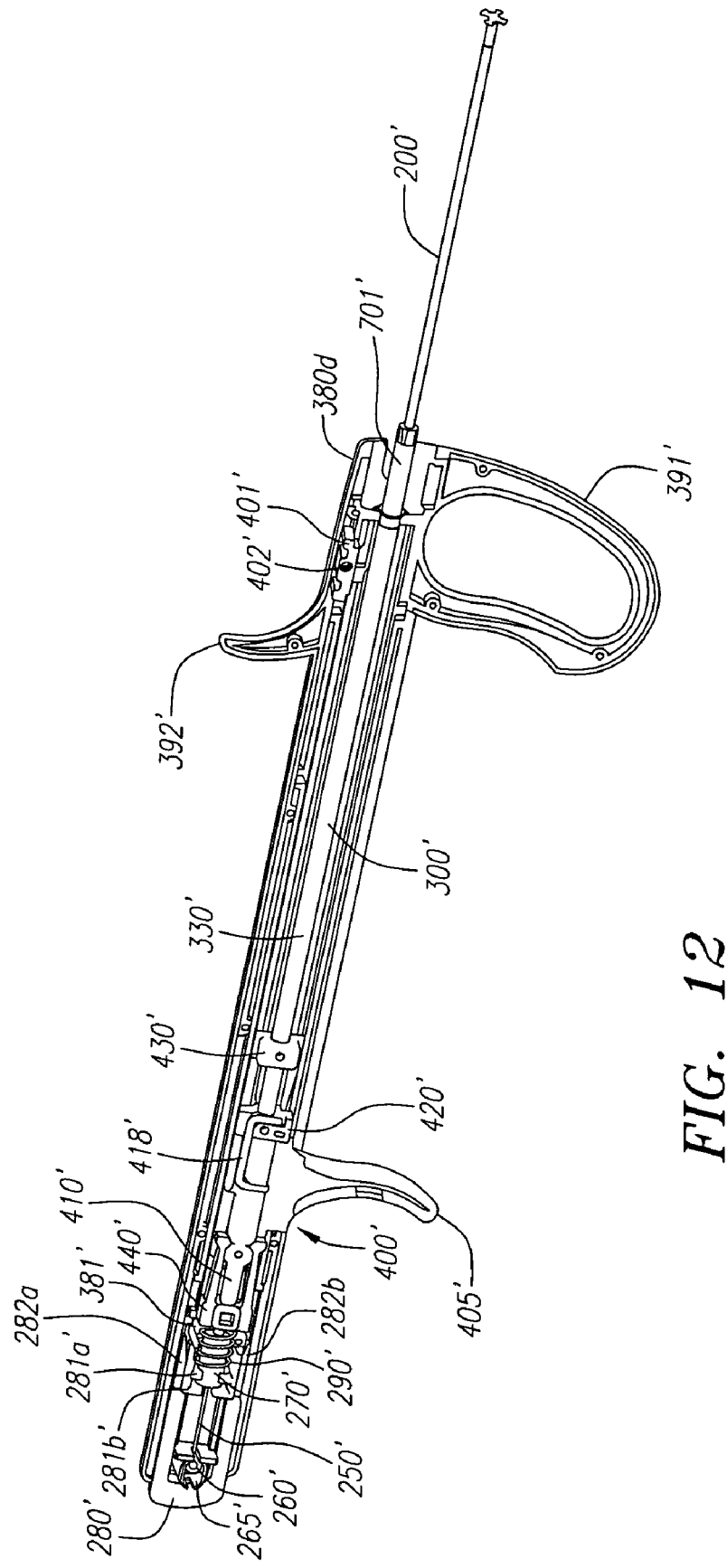
FIG. 12 illustrates the apparatus of FIG. 11A after advancement of the locator assembly block.
Figure 13A:
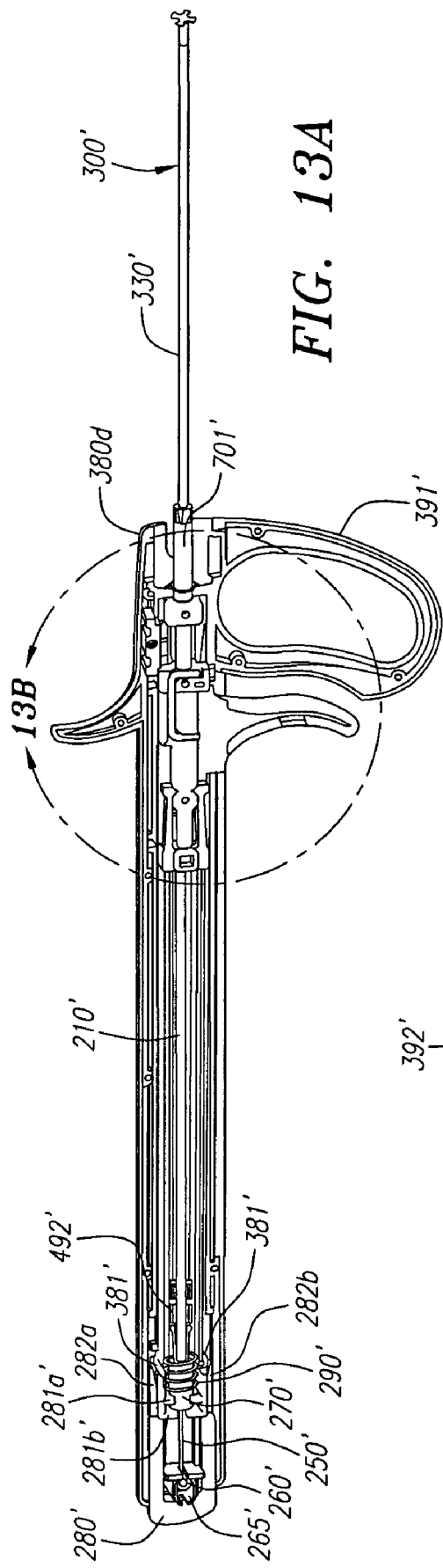
FIG. 13A illustrates the apparatus of FIG. 12 after distal advancement of the triggering system and carrier assembly.
Figure 13B:
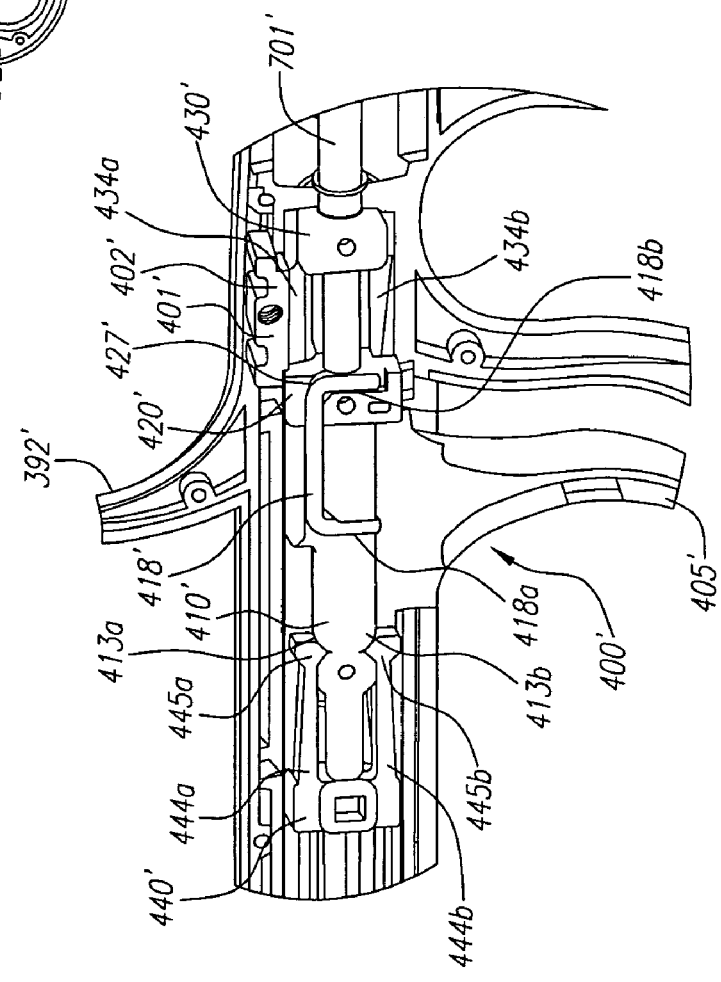
FIG. 13B illustrates a close-up view of the distal end of the housing and internal components of the apparatus shown in FIG. 13A.

The carrier block 410', pusher block 420', cover block 430', and support block 440' are shown in FIGS. 11-13 in their fully coupled state, with the support block 440' coupled to the carrier block 410', the pusher block 420' coupled to the carrier block 410', and the cover block 430' coupled to the pusher block 420'. In this arrangement, the carrier assembly 300' comprises a coaxial set of tubes (as shown, for example, in FIG. 3A), with the support member 340' slidably retained substantially within the carrier member 310', which is in turn slidably retained substantially within the pusher member 320', which is in turn slidably retained substantially within the cover member 330'.

The triggering system 400' of the-alternative embodiment of the apparatus includes an energy storing element that is used in the final stage of the closure element 500 delivery process. The energy storing element, preferably a spring such as the pusher spring 425' shown in FIGS. 10A-B and 14A-B, is substantially retained in a spring cavity 417' formed in the carrier block 410' and coaxially surrounds a proximal portion 310*a*' of the carrier member 310'. The pusher spring 425' is capable of expanding and contracting, storing potential energy as it is contracted and releasing energy as it expands. In its fully expanded state, the pusher spring 425' has a length that is greater than the length of the spring cavity 417'. The cross-sectional dimension of the pusher spring 425' is such that it backs up against and contacts the proximal end of the pusher block 420'. Thus, when the pusher spring 425' is in place between the carrier block 410' and the pusher block 420', the pusher spring 425' is capable of imparting a force biasing the carrier block 410' away from the pusher block 420'.

Prior to delivery of the closure element 500, the distal end of the carrier block 410' is in physical contact with the proximal end of the pusher block 420'. In this pre-delivery condition, the pusher spring 425' is in a contracted state and is maintained fully within the spring cavity 417' formed in the carrier block 410'. A catch member 418' serves the function of maintaining the carrier block 410' and pusher block 420' in the pre-delivery condition against the spring force of the pusher spring 425', the force of which would otherwise force apart the carrier block 410' from the pusher block 420'. The catch member 418' is a U-shaped piece of metal, plastic, or other rigid material that engages a first groove 418*a* formed on the surface of the carrier block 410' and a second groove 418*b* formed on the surface of the pusher block 420'. The pusher block 420' includes a hole 426' extending through a portion thereof, with one end of the hole 426' opening into the groove 418*b*. The hole 426' is adapted to receive a trip pin 427'. During the closure element deployment process, the trip pin 427' is advanced through the hole 426', where it encounters the catch member 418' that is retained in the groove 418*b*. Further advancement of the trip pin 427' causes the catch member 418' to become disengaged from the groove 418*b*, thereby releasing the restraining force on the pusher spring 425'.

The operation of the triggering system 400' of the alternative embodiment of the apparatus 100' is illustrated in FIGS. 11-14 with the closure element 500 (shown in FIGS. 6A-B) disposed substantially within the apparatus 100'. As shown in FIGS. 11A-B, the apparatus has an initial position in which the locator assembly block 280' is extended proximally and the triggering system 400' is in its most proximal position. Accordingly, the locator control system 200' is in its unexpanded state, as shown. At a point in time that the distal end region 210*b*' of the locator assembly 200' has been positioned as desired (for example, within the blood vessel 600), the locator assembly block 280 is depressed distally, as shown in FIG. 12, thereby transitioning the locator assembly to the expanded state and, simultaneously, releasing the triggering system 400' from the initial position (in the manner described above) such that the triggering system can be advanced distally within the housing 380'.

The triggering system 400' is then advanced distally within the housing 380', thereby advancing the tube set 305 into position adjacent the blood vessel. At a first predetermined position, shown in FIG. 13, the support block 440' encounters a support stop (not shown) on the interior surface of the housing bottom half 380*d* that inhibits the support block 440' from advancing further distally. As a result, an application of additional distal force to the triggering system 400' causes the support block 440' to decouple from the carrier block 410', as shown in FIG. 13. More specifically, the tabs 445*a-b* on the forks 444*a-b* of the support block 440' disengage from the grooves 413*a-b* on the carrier block 410'. Thus, the support block 440' remains in the position shown in FIG. 13, while the carrier block 410' is able to advance further distally upon application of force to the triggering system 400'.

Figure 14B:
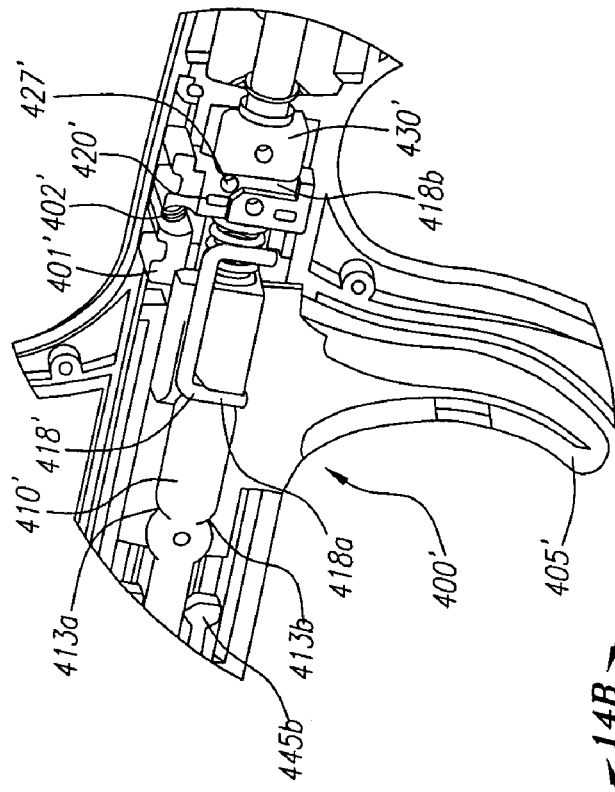
FIG. 14B illustrates a close-up view of the distal end of the housing and internal components of the apparatus shown in FIG. 14A.
Figure 14A:
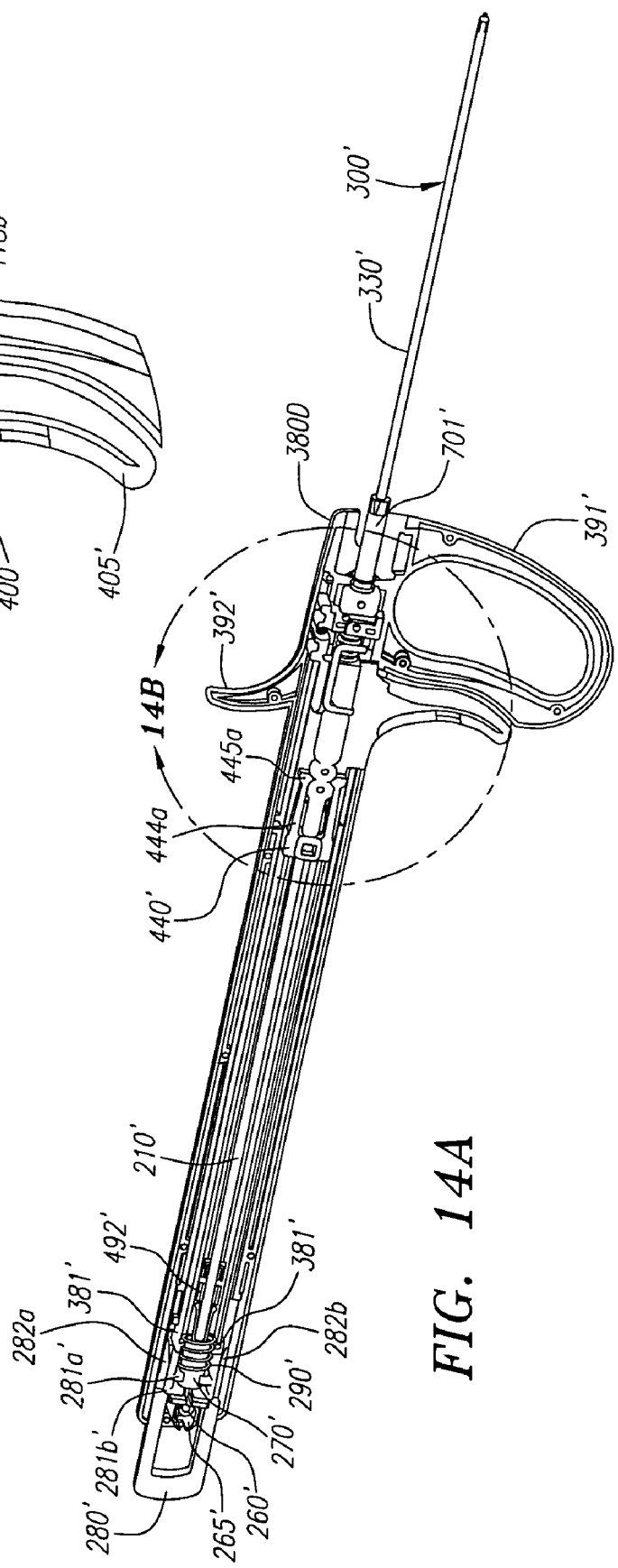
FIG. 14A illustrates the apparatus of FIG. 13 after further distal advancement of the triggering system and carrier assembly.

Turning to FIGS. 14A-B, as the triggering system 400' is advanced further distally, the cover block 430' engages a cover stop on the interior surface near the distal end of the housing 380', thereby inhibiting additional distal advancement of the cover block 430'. In addition, the trigger extension 405' engages the handle 391' on the exterior of the apparatus, thereby inhibiting additional distal advancement of the carrier block 410'. At this point, the distal end of the tube set corresponds generally to the state illustrated in FIG. 8G, prior to deployment of the closure element 500.

The closure element 500 is next deployed by releasing the pusher spring 425', which causes the pusher block 420' (and, thus, the pusher member 320') to advance distally, deploying the closure element in the manner described above. The pusher spring 425' is released by disengaging the catch member 418' from the groove 418*b* on the pusher block 420', thereby releasing the pusher spring 425' to force the pusher block 420'—and, thus, the pusher member 320'—distally relative to the carrier block 410'. This action causes the pusher member 320' to deploy the closure element 500, as shown, for example, in FIGS. 8H-L. The catch member 418' is disengaged from the groove 418*b* by applying a force to the trigger 401', which, in the deployment position, is aligned with the trip pin 427' retained in the pusher block 420'. A trigger spring 402' biases the trigger outward relative to the housing 380'. The user applies an inward directed force to the trigger 401' to counteract the biasing force of the trigger spring 402' and force the trigger 401' against the trip pin 427'.

In addition to deploying the closure element 500, the distal advancement of the pusher block 420' also causes the locator release system 490' to activate, thereby transitioning the locator control system 200' from the expanded state to the unexpanded state. As the pusher block 420' advances distally to deploy the closure element 500' in the manner described above, the pusher block 420' also engages the engagement member 493' of the locator release system 490' and advances the locator release rod 491' distally. This action causes the release tab spacer block 492' to disengage from the release tabs 284*a-b* on the locator assembly block 280' (see FIG. 15), thereby releasing the locator assembly block 280', which returns to its proximal position, causing the locator assembly 200' to return to the unexpanded state. The closure element 500 deployment and locator release actions occur nearly simultaneously, as illustrated in FIGS. 8I-K.

As described previously, the apparatus 100 is preferably brought into contact with the blood vessel 600 by inserting and advancing the distal end of the apparatus through an introducer sheath 640 to the blood vessel location. Although preferred, the use of an introducer sheath 640 is not necessary, as the apparatus can be used to deploy the closure element 500 without the use of an introducer sheath 640. Furthermore, as describe above, when an introducer sheath 640 is used, the locator assembly 200, 200' and the carrier assembly 300, 300' may have cross-sectional dimensions that allow them to be received within the introducer sheath 640 either without causing radial expansion or splitting of the sheath, or with causing radial expansion or splitting of the sheath. If the relative cross-sectional dimensions of the introducer sheath 640 and carrier assembly 300, 300' are such that the introducer sheath 640 is intended to be split during advancement of the carrier assembly 300, 200', a sheath cutter 701' having a pointed tip 702' may be utilized to initiate a split at the proximal end of the introducer sheath 640. The sheath cutter 701' is advantageously placed coaxially over the cover member 330' and is attached to the distal end of the housing 380' (see FIGS. 11A-B), whereby it will initiate a split in the introducer sheath 640. Distal advancement of the carrier assembly 300, 300' causes the initial split at the proximal end of the sheath to advance as the carrier assembly 300, 300' advances, as will be understood by those skilled in the art.

The invention is susceptible to various modifications and alternative forms, and specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the claims.

What is claimed is:

1. An apparatus for delivering a closure element to an opening formed in a wall of a body lumen or body tissue, comprising:
    a locator assembly having a distal end region and a locator control system coupled to a proximal end region of said locator assembly, said locator control system being configured to selectively control said distal end region of said locator assembly between an unexpanded state and an expanded state for engaging said wall of said body lumen or said body tissue adjacent to said opening;
    a carrier assembly coupled with said locator assembly, said carrier assembly comprising a carrier member for retaining said closure element in a substantially tubular configuration within said carrier assembly, and a pusher member adapted to deploy said closure element;
    a cover member configured to retain said closure element, said cover member having a distal end region and a proximal end region, said distal end region of said cover member including one or more longitudinal extensions extending distally and substantially radially inwardly with respect to said proximal end region and being configured to expand radially;
    an energy storing member associated with said carrier assembly and said locator control system, said energy storing member configured to cause a proximal end of said pusher member to move distally from a proximal end of said carrier member and to move a portion of said proximal end region of the locator control system proximally to disengage the distal end region of the locator assembly from engaging said wall of said body lumen or said body tissue.

2. The apparatus of claim 1, wherein said energy storing member comprises a spring.

3. The apparatus of claim 2, wherein said spring is disposed substantially between said carrier member and said pusher member.

4. The apparatus of claim 3, wherein said spring is substantially disposed in a cavity located on one of said carrier member or said pusher member.

5. The apparatus of claim 3, further comprising a catch member adapted to selectably maintain said carrier member in proximity to said pusher member against a spring force imparted by said spring.

6. The apparatus of claim 5, further comprising a trigger selectably engageable with said catch member, said trigger adapted to cause said catch member to release said spring.

7. The apparatus of claim 6, wherein said distal end region of said locator assembly includes an expansion element configured to expand substantially transversely with respect to a longitudinal axis of the locator assembly.

8. The apparatus of claim 7, wherein said expansion element comprises a plurality of substantially flexible members each having a substantially fixed end region fixedly coupled with said distal end region of said locator assembly, an intermediate region, and a movable end region movable coupled with said distal end region of said locator assembly such that said intermediate regions are configured to expand transversely outwardly when said movable end regions are axially moved toward said substantially fixed end regions.

9. The apparatus of claim 3, wherein said carrier assembly comprises a carrier member for receiving and supporting said closure element in said substantially tubular configuration and a pusher member for distally deploying said closure element, said carrier member, said pusher member, and said cover member being slidably coupled.

10. The apparatus of claim 9, wherein said carrier member, said pusher member, and said cover member are provided as a plurality of nested, telescoping members with a common longitudinal axis.

11. The apparatus of claim 10, wherein said carrier member defines a lumen, said distal end region of said locator assembly being substantially axially aligned with, and at least partially slidably disposable within, said lumen of said carrier member.

12. The apparatus of claim 11, wherein said distal end region of said carrier member has a cross-section that increases distally for expanding said closure element to a cross-section that is greater than a natural cross-section of said closure element.

13. The apparatus of claim 12, wherein said distal end region of said pusher member includes one or more longitudinal extensions extending distally and being configured to expand radially as said distal end region of said pusher member moves distally and engages said distally-increasing cross-section of said distal end region of said carrier member.

14. The apparatus of claim 9, wherein said carrier assembly further includes a support member being slidably coupled with said carrier member, said pusher member, and said cover member and being configured to provide radial support for said distal end region of said cover member.

15. The apparatus of claim 14, wherein said carrier member, said pusher member, said cover member, and said support member are provided as a plurality of nested, telescoping members with a common longitudinal axis.

16. An apparatus for delivering a closure element to an opening formed in a wall of a body lumen or body tissue, comprising:
    a locator assembly having a distal end region and a locator control system coupled to a proximal end region of said locator assembly, said locator control system being configured to selectively control said distal end region of said locator assembly between an unexpanded state and an expanded state for engaging said wall of said body lumen or said body tissue adjacent to said opening;

a carrier assembly coupled with and receiving at least a portion of said locator assembly, said carrier assembly comprising a carrier member configured for retaining said closure element in a substantially tubular configuration within said carrier assembly, and a pusher member adapted to deploy said closure element;

a cover member configured to retain said closure element, said cover member having a distal end region and a proximal end region, said distal end region of said cover member including one or more longitudinal extensions extending distally and substantially radially inwardly with respect to said proximal end region and being configured to expand radially;

means associated with said locator assembly and carrier assembly for causing a proximal end of said pusher member to move distally from a proximal end of said carrier member and to move a proximal portion of the locator assembly to disengage said distal end region of said locator assembly from said wall of said body lumen or body tissue.

17. The apparatus of claim 16, wherein said distal end region of said locator assembly includes an expansion element configured to expand substantially transversely with respect to a longitudinal axis of the locator assembly.

18. The apparatus of claim 17, wherein said expansion element comprises a plurality of substantially flexible members each having a substantially fixed end region fixedly coupled with said distal end region of said locator assembly, an intermediate region, and a movable end region movable coupled with said distal end region of said locator assembly such that said intermediate regions are configured to expand transversely outwardly when said movable end regions are axially moved toward said substantially fixed end regions.

19. The apparatus of claim 16, wherein said carrier assembly comprises a carrier member for receiving and supporting said closure element in said substantially tubular configuration and a pusher member for distally deploying said closure element, said carrier member, said pusher member, and said cover member being slidably coupled.

20. The apparatus of claim 19, wherein said carrier member, said pusher member, and said cover member are provided as a plurality of nested, telescoping members with a common longitudinal axis.

21. The apparatus of claim 20, wherein said carrier member defines a lumen, said distal end region of said locator assembly being substantially axially aligned with, and at least partially slidably disposable within, said lumen of said carrier member.

22. The apparatus of claim 21, wherein said distal end region of said carrier member has a cross-section that increases distally for expanding said closure element to a cross-section that is greater than a natural cross-section of said closure element.

23. The apparatus of claim 22, wherein said distal end region of said pusher member includes one or more longitudinal extensions extending distally and being configured to expand radially as said distal end region of said pusher member moves distally and engages said distally-increasing cross-section of said distal end region of said carrier member.

24. The apparatus of claim 19, wherein said carrier assembly further includes a support member being slidably coupled with said carrier member, said pusher member, and said cover member and being configured to provide radial support for said distal end region of said cover member.

25. The apparatus of claim 24, wherein said carrier member, said pusher member, said cover member, and said support member are provided as a plurality of nested, telescoping members with a common longitudinal axis.

26. An apparatus for delivering a closure element to an opening formed in a wall of a body lumen or body tissue, comprising:

a locator assembly having a distal end region configured to extend into said opening and to selectably engage said wall of said body lumen or said body tissue adjacent to said opening and a proximal end region;

a carrier assembly coupled with said locator assembly, said carrier assembly comprising a carrier member for retaining said closure element in a substantially tubular configuration within said carrier assembly, and a pusher member adapted to deploy said closure element, said distal end region of said carrier member having a cross-section that increases distally for expanding said closure element to a cross-section that is greater than a natural cross-section of said closure element, said distal end region of said pusher member including one or more longitudinal extensions extending distally and being configured to expand radially as said distal end region of said pusher member moves distally and engages said distally-increasing cross-section of said distal end region of said carrier member;

a cover member for retaining said closure element, said carrier member, said pusher member, and said cover member being slidably coupled, said carrier member, said pusher member, and said cover member being provided as a plurality of nested, telescoping members with a common longitudinal axis, said cover member having a distal end region and a proximal end region, said distal end region of said cover member including one or more longitudinal extensions extending distally and substantially radially inwardly with respect to said proximal end region and being configured to expand radially;

an energy storing member associated with said carrier assembly, said energy storing member configured to cause a proximal end of said pusher member to move distally from a proximal end of said carrier member and to move a portion of the proximal end region of the locator assembly proximally to disengage the distal end region of the locator assembly from engaging said wall of said body lumen or said body tissue;

wherein a portion of said locator assembly is substantially axially aligned with, and at least partially slidably disposable within, said lumen of said carrier member wherein said closure element is configured to engage at least a portion of said wall of said body lumen or said body tissue whereby said opening is drawn substantially closed.

* * * * *